(12) United States Patent
Ji et al.

(10) Patent No.: US 11,628,162 B2
(45) Date of Patent: Apr. 18, 2023

(54) METHODS OF TREATING CANCER WITH AN FGFR INHIBITOR

(71) Applicant: Incyte Corporation, Wilmington, DE (US)

(72) Inventors: Tao Ji, Basking Ridge, NJ (US); Krishnaswamy Yeleswaram, Landenberg, PA (US)

(73) Assignee: Incyte Corporation, Wilmington, DE (US)

( * ) Notice: Subject to any disclaimer, the term of this patent is extended or adjusted under 35 U.S.C. 154(b) by 177 days.

(21) Appl. No.: 16/811,640

(22) Filed: Mar. 6, 2020

(65) Prior Publication Data
US 2020/0281907 A1  Sep. 10, 2020

Related U.S. Application Data

(60) Provisional application No. 62/815,772, filed on Mar. 8, 2019.

(51) Int. Cl.
| | | |
|---|---|---|
| *A61K 31/4375* | (2006.01) | |
| *A61K 31/5375* | (2006.01) | |
| *A61K 31/5377* | (2006.01) | |
| *A61P 35/00* | (2006.01) | |

(52) U.S. Cl.
CPC ...... *A61K 31/4375* (2013.01); *A61K 31/5375* (2013.01); *A61K 31/5377* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 850,370 | A | 4/1907 | Hynes |
| 3,894,021 | A | 7/1975 | Denzel et al. |
| 4,271,074 | A | 6/1981 | Lohmann et al. |
| 4,339,267 | A | 7/1982 | Levitt |
| 4,347,348 | A | 8/1982 | Chernikhov et al. |
| 4,402,878 | A | 9/1983 | D'Alelio et al. |
| 4,405,519 | A | 9/1983 | D'Alelio et al. |
| 4,405,520 | A | 9/1983 | D'Alelio et al. |
| 4,405,786 | A | 9/1983 | D'Alelio et al. |
| 4,460,773 | A | 7/1984 | Suzuki et al. |
| 4,874,803 | A | 10/1989 | Baron et al. |
| 4,940,705 | A | 7/1990 | Boshagen et al. |
| 5,159,054 | A | 10/1992 | Keller |
| 5,240,941 | A | 8/1993 | Bruneau |
| 5,480,887 | A | 1/1996 | Hornback et al. |
| 5,521,184 | A | 5/1996 | Zimmermann et al. |
| 5,536,725 | A | 7/1996 | Cullen et al. |
| 5,541,324 | A | 7/1996 | TenBrink et al. |
| 5,760,068 | A | 6/1998 | Talley et al. |
| 5,783,577 | A | 7/1998 | Houghten et al. |
| 5,845,025 | A | 12/1998 | Garito et al. |
| 5,994,364 | A | 11/1999 | Njoroge et al. |
| 6,465,484 | B1 | 10/2002 | Bilodeau et al. |
| 6,998,408 | B2 | 2/2006 | Pinto |
| 7,074,801 | B1 | 7/2006 | Yoshida et al. |
| 7,125,880 | B1 | 10/2006 | Chen |
| 7,488,802 | B2 | 2/2009 | Collins et al. |
| 7,618,975 | B2 | 11/2009 | Cai et al. |
| 7,642,255 | B2 | 1/2010 | Sim |
| 7,648,973 | B2 | 1/2010 | DeLuca et al. |
| 7,943,743 | B2 | 5/2011 | Korman et al. |
| 8,008,449 | B2 | 8/2011 | Korman et al. |
| 8,168,757 | B2 | 5/2012 | Finnefrock et al. |
| 8,217,149 | B2 | 7/2012 | Irving et al. |
| 8,759,398 | B2 | 1/2014 | Nelson |
| 8,754,114 | B2 | 6/2014 | Yao et al. |
| 8,889,711 | B2 | 11/2014 | Bedjeguelal |
| 9,266,892 | B2 | 2/2016 | Zhuo et al. |
| 9,388,185 | B2 | 7/2016 | Lu et al. |
| 9,533,954 | B2 | 1/2017 | Yao et al. |
| 9,533,984 | B2 | 1/2017 | Sun et al. |
| 9,580,423 | B2 | 2/2017 | Lu et al. |
| 9,611,267 | B2 | 4/2017 | Wu et al. |
| 9,708,318 | B2 | 7/2017 | Lu et al. |
| 9,745,311 | B2 | 8/2017 | Lu et al. |
| 9,801,889 | B2 | 10/2017 | Lu et al. |
| 9,890,156 | B2 | 2/2018 | Lu et al. |
| 10,016,348 | B2 | 7/2018 | Lu et al. |
| 10,040,790 | B2 | 8/2018 | Sun et al. |
| 10,131,667 | B2 | 11/2018 | Wu et al. |
| 10,208,024 | B2 | 2/2019 | Andrews et al. |
| 10,213,427 | B2 | 2/2019 | Yao et al. |
| 10,214,528 | B2 | 2/2019 | Lu et al. |
| 10,251,892 | B2 | 4/2019 | Sokolsky et al. |
| 10,308,644 | B2 | 6/2019 | Wu et al. |
| 10,350,240 | B2 | 6/2019 | Gore et al. |

(Continued)

FOREIGN PATENT DOCUMENTS

| | | |
|---|---|---|
| CL | 2014003355 | 6/2015 |
| CL | 2015002628 | 8/2016 |

(Continued)

OTHER PUBLICATIONS

Australian Office Action in Australian Application No. 2018272013, dated Sep. 2, 2021, 4 pages.
Australian Office Action in Australian Application No. 2020250211, dated Sep. 13, 2021, 4 pages.
Casey et al., "Translating in vivo metabolomic analysis of succinate dehydrogenase deficient tumours into clinical utility," JCO Precis Oncol., Mar. 29, 2018, 2:1-12.
Cherukupalli et al., "An insight on synthetic and medicinal aspects of pyrazolo[1,5-a]pyrimidine scaffold," European Journal of Medicinal Chemistiy, Nov. 10, 2016, 126:298-352.
Chinese Office Action in Chinese Application No. 201910023729.3, dated Sep. 8, 2021, 11 pages.

(Continued)

*Primary Examiner* — Brian J Davis
(74) *Attorney, Agent, or Firm* — Fish & Richardson P.C.

(57) ABSTRACT

This application relates to methods of treating cancer in a patient in need thereof, comprising administering a Fibroblast Growth Factor Receptors (FGFR) inhibitor to the patient.

11 Claims, 10 Drawing Sheets

(56) References Cited

U.S. PATENT DOCUMENTS

| | | |
|---|---|---|
| 10,357,431 B2 | 7/2019 | Staric et al. |
| 10,450,313 B2 | 10/2019 | Lu et al. |
| 10,611,762 B2 | 4/2020 | Jia et al. |
| 10,632,126 B2 | 4/2020 | Lu et al. |
| 10,738,048 B2 | 8/2020 | Lu et al. |
| 10,813,930 B2 | 10/2020 | Yao et al. |
| 10,851,105 B2 | 12/2020 | Wu et al. |
| 10,947,230 B2 | 3/2021 | Sun et al. |
| 11,014,923 B2 | 5/2021 | Lu et al. |
| 11,053,246 B2 | 7/2021 | Wu et al. |
| 11,173,162 B2 | 11/2021 | Sokolsky et al. |
| 11,174,257 B2 | 11/2021 | Jia et al. |
| 11,407,750 B2 | 8/2022 | Tao et al. |
| 11,466,004 B2 | 10/2022 | Burn |
| 11,472,801 B2 | 10/2022 | Pan et al. |
| 2003/0078255 A1 | 4/2003 | Pinto |
| 2003/0078277 A1 | 4/2003 | Hibi et al. |
| 2003/0181622 A1 | 9/2003 | Chiu et al. |
| 2004/0044012 A1 | 3/2004 | Dobrusin et al. |
| 2004/0067948 A1 | 4/2004 | Hallett |
| 2004/0097493 A1 | 5/2004 | Chen et al. |
| 2004/0122029 A1 | 6/2004 | Liu et al. |
| 2004/0127538 A1 | 7/2004 | Oinuma et al. |
| 2004/0204427 A1 | 10/2004 | Chen et al. |
| 2005/0009876 A1 | 1/2005 | Bhagwat et al. |
| 2005/0070542 A1 | 3/2005 | Hodgetts et al. |
| 2005/0148603 A1 | 7/2005 | Jimenez et al. |
| 2005/0197340 A1 | 9/2005 | Arora et al. |
| 2005/0222171 A1 | 10/2005 | Bold et al. |
| 2006/0222637 A1 | 10/2006 | Bamdad |
| 2006/0270849 A1 | 11/2006 | Nishino et al. |
| 2007/0116984 A1 | 5/2007 | Park et al. |
| 2007/0197510 A1 | 8/2007 | Ohmoto et al. |
| 2007/0225286 A1 | 9/2007 | Ren et al. |
| 2007/0280943 A1 | 12/2007 | Friedman et al. |
| 2008/0249301 A1 | 10/2008 | Hornberger et al. |
| 2009/0098086 A1 | 4/2009 | Zask et al. |
| 2009/0099165 A1 | 4/2009 | Hurley et al. |
| 2009/0099190 A1 | 4/2009 | Flynn et al. |
| 2009/0105233 A1 | 4/2009 | Chua et al. |
| 2009/0131467 A1 | 5/2009 | Kanazawa et al. |
| 2009/0163545 A1 | 6/2009 | Goldfarb |
| 2009/0246198 A1 | 10/2009 | Dong et al. |
| 2010/0032626 A1 | 2/2010 | Akino |
| 2010/0099684 A1 | 4/2010 | Cook, II et al. |
| 2010/0105661 A1 | 4/2010 | Shirakami et al. |
| 2010/0143547 A1 | 6/2010 | Kriegel et al. |
| 2010/0204235 A1 | 8/2010 | Lizos |
| 2010/0210636 A1 | 8/2010 | Ishikawa et al. |
| 2010/0216798 A1 | 8/2010 | Nakai et al. |
| 2010/0239496 A1 | 9/2010 | Gangadharmath et al. |
| 2011/0045511 A1 | 2/2011 | Graus Porta et al. |
| 2011/0159604 A1 | 6/2011 | Fan et al. |
| 2011/0160203 A1 | 6/2011 | Liu et al. |
| 2011/0195968 A1 | 8/2011 | Greul et al. |
| 2011/0212077 A1 | 9/2011 | Noronha et al. |
| 2011/0224155 A1 | 9/2011 | Tachdjian et al. |
| 2011/0262525 A1 | 10/2011 | Wang et al. |
| 2011/0313003 A1 | 12/2011 | Shi et al. |
| 2012/0035153 A1 | 2/2012 | Saxty et al. |
| 2012/0135997 A1 | 5/2012 | Kato et al. |
| 2012/0165305 A1 | 6/2012 | Yao et al. |
| 2012/0295881 A1 | 11/2012 | Lange et al. |
| 2012/0319095 A1 | 12/2012 | Tada et al. |
| 2013/0078731 A1 | 3/2013 | George et al. |
| 2013/0200356 A1 | 8/2013 | Jung et al. |
| 2013/0210825 A1 | 8/2013 | Rehwinkel et al. |
| 2013/0338134 A1 | 12/2013 | Wu et al. |
| 2014/0045814 A1 | 2/2014 | Lu et al. |
| 2014/0054564 A1 | 2/2014 | Kim et al. |
| 2014/0080892 A1 | 3/2014 | Bhanot et al. |
| 2014/0088100 A1 | 3/2014 | Bifulco, Jr. et al. |
| 2014/0103325 A1 | 4/2014 | Shin et al. |
| 2014/0117318 A1 | 5/2014 | Choi et al. |
| 2014/0148548 A1 | 5/2014 | Yamanaka et al. |
| 2014/0171405 A1 | 6/2014 | Zhuo et al. |
| 2014/0187559 A1 | 7/2014 | Miduturu |
| 2014/0194430 A1 | 7/2014 | Eis et al. |
| 2014/0228370 A1 | 8/2014 | Eis et al. |
| 2014/0243308 A1 | 8/2014 | Yao et al. |
| 2014/0288069 A1 | 9/2014 | Eis et al. |
| 2014/0296233 A1 | 10/2014 | D'Agostino et al. |
| 2014/0315902 A1 | 10/2014 | Sun et al. |
| 2014/0374722 A1 | 12/2014 | Kim et al. |
| 2014/0378468 A1 | 12/2014 | Aichholz et al. |
| 2014/0378481 A1 | 12/2014 | Bifulco, Jr. et al. |
| 2014/0378483 A1 | 12/2014 | Benazet et al. |
| 2015/0011548 A1 | 1/2015 | Linnanen et al. |
| 2015/0011560 A1 | 1/2015 | Legeai-Mallet |
| 2015/0011579 A1 | 1/2015 | Clary-Ceccato et al. |
| 2015/0038485 A1 | 2/2015 | Eis et al. |
| 2015/0197519 A1 | 7/2015 | Bifulco |
| 2016/0115164 A1 | 4/2016 | Wu et al. |
| 2016/0244448 A1 | 8/2016 | Lu et al. |
| 2016/0244449 A1 | 8/2016 | Lu et al. |
| 2016/0244450 A1 | 8/2016 | Lu et al. |
| 2016/0280713 A1 | 9/2016 | Lu et al. |
| 2017/0107216 A1 | 4/2017 | Wu et al. |
| 2017/0119782 A1 | 5/2017 | Lu et al. |
| 2017/0137424 A1 | 5/2017 | Wu et al. |
| 2017/0145025 A1 | 5/2017 | Li et al. |
| 2017/0165263 A1 | 6/2017 | Yao et al. |
| 2017/0166564 A1 | 6/2017 | Sun et al. |
| 2017/0174671 A1 | 6/2017 | Wu et al. |
| 2017/0174679 A1 | 6/2017 | Lajkiewicz et al. |
| 2017/0260168 A1 | 9/2017 | Andrews et al. |
| 2017/0290839 A1 | 10/2017 | Lu et al. |
| 2017/0320875 A1 | 11/2017 | Li et al. |
| 2017/0320877 A1 | 11/2017 | Wu et al. |
| 2017/0342060 A1 | 11/2017 | Lu et al. |
| 2017/0362253 A1 | 12/2017 | Xiao et al. |
| 2018/0008610 A1 | 1/2018 | Lu et al. |
| 2018/0016260 A1 | 1/2018 | Yu et al. |
| 2018/0057486 A1 | 3/2018 | Wu et al. |
| 2018/0072718 A1 | 3/2018 | Liu et al. |
| 2018/0177784 A1 | 6/2018 | Wu et al. |
| 2018/0177870 A1 | 6/2018 | Liu et al. |
| 2018/0179179 A1 | 6/2018 | Wu et al. |
| 2018/0179197 A1 | 6/2018 | Wu et al. |
| 2018/0179201 A1 | 6/2018 | Wu et al. |
| 2018/0179202 A1 | 6/2018 | Wu et al. |
| 2018/0244672 A1 | 8/2018 | Lu et al. |
| 2018/0273519 A1 | 9/2018 | Wu et al. |
| 2019/0040082 A1 | 2/2019 | Xiao et al. |
| 2019/0055237 A1 | 2/2019 | Pan et al. |
| 2019/0062327 A1 | 2/2019 | Sun et al. |
| 2019/0062345 A1 | 2/2019 | Xiao et al. |
| 2019/0071439 A1 | 3/2019 | Li et al. |
| 2019/0092767 A1 | 3/2019 | Li et al. |
| 2019/0127376 A1 | 5/2019 | Wu et al. |
| 2019/0127467 A1 | 5/2019 | Shah et al. |
| 2019/0144439 A1 | 5/2019 | Wu et al. |
| 2019/0202824 A1 | 7/2019 | Wu et al. |
| 2019/0225601 A1 | 7/2019 | Wu et al. |
| 2019/0240220 A1 | 8/2019 | Yao et al. |
| 2019/0241560 A1 | 8/2019 | Lu et al. |
| 2019/0269693 A1 | 9/2019 | Lu et al. |
| 2019/0284187 A1 | 9/2019 | Wu et al. |
| 2019/0300524 A1 | 10/2019 | Wu et al. |
| 2019/0337948 A1 | 11/2019 | Frietze et al. |
| 2019/0345170 A1 | 11/2019 | Wu et al. |
| 2020/0002338 A1 | 1/2020 | Jia et al. |
| 2020/0055853 A1 | 2/2020 | Ellies et al. |
| 2020/0095244 A1 | 3/2020 | Sun et al. |
| 2020/0255424 A1 | 8/2020 | Wu et al. |
| 2020/0270245 A1 | 8/2020 | Pan et al. |
| 2020/0277309 A1 | 9/2020 | Wu et al. |
| 2020/0306256 A1 | 10/2020 | Lu et al. |
| 2020/0377504 A1 | 12/2020 | Wu et al. |
| 2020/0399267 A1 | 12/2020 | Lu et al. |
| 2021/0009582 A1 | 1/2021 | Vechorkin et al. |
| 2021/0094935 A1 | 4/2021 | Vechorkin |
| 2021/0106588 A1 | 4/2021 | Vechorkin et al. |
| 2021/0115053 A1 | 4/2021 | Shvartsbart et al. |

(56) References Cited

U.S. PATENT DOCUMENTS

| | | |
|---|---|---|
| 2021/0171522 A1 | 6/2021 | Tao et al. |
| 2021/0171535 A1 | 6/2021 | McCammant et al. |
| 2021/0214366 A1 | 7/2021 | Roach et al. |
| 2021/0380587 A1 | 12/2021 | Wu et al. |
| 2021/0395246 A1 | 12/2021 | Sun et al. |
| 2022/0009921 A1 | 1/2022 | Lu et al. |
| 2022/0153740 A1 | 5/2022 | Jia et al. |

FOREIGN PATENT DOCUMENTS

| | | |
|---|---|---|
| CL | 2017000654 | 12/2017 |
| CL | 2017001984 | 3/2018 |
| CL | 2018000089 | 5/2018 |
| CL | 2018000124 | 5/2018 |
| CL | 2017002117 | 6/2018 |
| CL | 2018000036 | 6/2018 |
| CL | 2018000128 | 6/2018 |
| CL | 2018003322 | 1/2019 |
| CN | 1863774 | 11/2006 |
| CN | 101007778 | 8/2007 |
| CN | 101679408 | 3/2010 |
| CN | 101715451 | 5/2010 |
| CN | 102399220 | 4/2012 |
| CN | 102399233 | 4/2012 |
| CN | 102666536 | 9/2012 |
| CN | 103571502 | 2/2014 |
| CN | 103588771 | 2/2014 |
| CN | 104262330 | 1/2015 |
| DE | 2156720 | 5/1973 |
| DE | 2934578 | 3/1981 |
| DE | 3432983 | 4/1985 |
| DE | 280853 | 7/1990 |
| DE | 3937633 | 5/1991 |
| DE | 4119767 | 12/1992 |
| DE | 19912638 | 9/2000 |
| EP | 0466452 | 1/1992 |
| EP | 0995751 | 4/2000 |
| EP | 1199070 | 4/2002 |
| EP | 1217000 | 6/2002 |
| EP | 1388541 | 2/2004 |
| EP | 2651404 | 10/2015 |
| EP | 3184521 | 6/2017 |
| FR | 2428654 | 1/1980 |
| FR | 2876582 | 4/2006 |
| FR | 2983196 | 5/2013 |
| FR | 2983199 | 5/2013 |
| FR | 2983200 | 5/2013 |
| JP | 62273979 | 11/1987 |
| JP | 63017882 | 1/1988 |
| JP | S 6310630 | 1/1988 |
| JP | 02009895 | 1/1990 |
| JP | H 0348656 | 3/1991 |
| JP | H 03275669 | 12/1991 |
| JP | 04179576 | 6/1992 |
| JP | H 04158084 | 6/1992 |
| JP | H 04328121 | 11/1992 |
| JP | H 05320173 | 12/1993 |
| JP | H 05320515 | 12/1993 |
| JP | H 09188812 | 7/1997 |
| JP | H 1060426 | 3/1998 |
| JP | H 11171865 | 6/1999 |
| JP | 2000123973 | 4/2000 |
| JP | 2001035664 | 2/2001 |
| JP | 2001265031 | 9/2001 |
| JP | 2002516327 | 6/2002 |
| JP | 2002296731 | 10/2002 |
| JP | 2003335788 | 11/2003 |
| JP | 2004203749 | 7/2004 |
| JP | 2004346145 | 12/2004 |
| JP | 2005015395 | 1/2005 |
| JP | 2005320288 | 11/2005 |
| JP | 2006028027 | 2/2006 |
| JP | 2006514624 | 5/2006 |
| JP | 2006284843 | 10/2006 |
| JP | 2006522756 | 10/2006 |
| JP | 2006316054 | 11/2006 |
| JP | 2007500725 | 1/2007 |
| JP | 2008198769 | 8/2008 |
| JP | 2009537520 | 10/2009 |
| JP | 2010180147 | 8/2010 |
| JP | 2010248429 | 11/2010 |
| JP | 2010267847 | 11/2010 |
| JP | 2010270245 | 12/2010 |
| JP | 2010272618 | 12/2010 |
| JP | 2010272727 | 12/2010 |
| JP | 2010278114 | 12/2010 |
| JP | 2011009348 | 1/2011 |
| JP | 2011044637 | 3/2011 |
| JP | 2011116840 | 6/2011 |
| JP | 2011222650 | 11/2011 |
| JP | 2012116825 | 6/2012 |
| JP | 2012136476 | 7/2012 |
| JP | 5120580 | 1/2013 |
| JP | 2013049251 | 3/2013 |
| JP | 2013179181 | 9/2013 |
| JP | 2015517376 | 6/2015 |
| JP | 20155017376 | 6/2015 |
| JP | 2018507214 | 3/2018 |
| JP | 2018511573 | 4/2018 |
| JP | 6336665 | 6/2018 |
| KR | 20010043829 | 5/2001 |
| KR | 20080045536 | 5/2008 |
| KR | 20110023190 | 3/2011 |
| KR | 20110043270 | 4/2011 |
| KR | 20120052034 | 5/2012 |
| KR | 20120078303 | 7/2012 |
| KR | 20130043460 | 4/2013 |
| KR | 20140090411 | 7/2014 |
| KR | 20140099105 | 8/2014 |
| WO | WO 1988/03025 | 5/1988 |
| WO | WO 1991/09835 | 7/1991 |
| WO | WO 1991/10172 | 7/1991 |
| WO | WO 1992/06078 | 4/1992 |
| WO | WO 1992/22552 | 12/1992 |
| WO | WO 1993/24488 | 12/1993 |
| WO | WO 1994/13669 | 6/1994 |
| WO | WO 1994/15995 | 7/1994 |
| WO | WO 1994/25438 | 11/1994 |
| WO | WO 1995/20965 | 8/1995 |
| WO | WO 1996/15128 | 5/1996 |
| WO | WO 1996/40707 | 12/1996 |
| WO | WO 1997/47601 | 12/1997 |
| WO | WO 1998/05661 | 2/1998 |
| WO | WO 1998/06703 | 2/1998 |
| WO | WO 1998/11438 | 3/1998 |
| WO | WO 1998/18781 | 5/1998 |
| WO | WO 1998/28281 | 7/1998 |
| WO | WO 1998/33798 | 8/1998 |
| WO | WO 1998/46609 | 10/1998 |
| WO | WO 1998/54156 | 12/1998 |
| WO | WO 1999/06422 | 2/1999 |
| WO | WO 1999/07732 | 2/1999 |
| WO | WO 1999/09030 | 2/1999 |
| WO | WO 1999/42442 | 8/1999 |
| WO | WO 1999/59975 | 11/1999 |
| WO | WO 1999/61444 | 12/1999 |
| WO | WO 1999/64400 | 12/1999 |
| WO | WO 2000/09495 | 2/2000 |
| WO | WO 2002/000196 | 2/2000 |
| WO | WO 2000/24744 | 5/2000 |
| WO | WO 2000/053595 | 9/2000 |
| WO | WO 2000/68186 | 11/2000 |
| WO | WO 2001/02369 | 1/2001 |
| WO | WO 2001/014402 | 3/2001 |
| WO | WO 2001/22938 | 4/2001 |
| WO | WO 2001/23386 | 4/2001 |
| WO | WO 2001/29041 | 4/2001 |
| WO | WO 2001/29042 | 4/2001 |
| WO | WO 2001/42247 | 6/2001 |
| WO | WO 2001/47892 | 7/2001 |
| WO | WO 2001/53273 | 7/2001 |
| WO | WO 2001/55148 | 8/2001 |
| WO | WO 2001/57037 | 8/2001 |
| WO | WO 2001/57038 | 8/2001 |

(56) References Cited

FOREIGN PATENT DOCUMENTS

| | | |
|---|---|---|
| WO | WO 2001/58899 | 8/2001 |
| WO | WO 2001/64655 | 9/2001 |
| WO | WO 2001/66099 | 9/2001 |
| WO | WO 2001/68647 | 9/2001 |
| WO | WO 2001/83472 | 11/2001 |
| WO | WO 2001/85722 | 11/2001 |
| WO | WO 2002/00655 | 1/2002 |
| WO | WO 2002/12442 | 2/2002 |
| WO | WO 2002/14315 | 2/2002 |
| WO | WO 2002/20011 | 3/2002 |
| WO | WO 2002/051831 | 7/2002 |
| WO | WO 2002/055082 | 7/2002 |
| WO | WO 2002/066481 | 8/2002 |
| WO | WO 2002/74754 | 9/2002 |
| WO | WO 2002/076953 | 10/2002 |
| WO | WO 2002/083648 | 10/2002 |
| WO | WO 2002/088095 | 11/2002 |
| WO | WO 2002/094825 | 11/2002 |
| WO | WO 2002/096873 | 12/2002 |
| WO | WO 2002/102793 | 12/2002 |
| WO | WO 2003/000187 | 1/2003 |
| WO | WO 2003/000688 | 1/2003 |
| WO | WO 2003/000690 | 1/2003 |
| WO | WO 2003/009852 | 2/2003 |
| WO | WO 2003/014083 | 2/2003 |
| WO | WO 2003/024967 | 3/2003 |
| WO | WO 2003/037347 | 5/2003 |
| WO | WO 2003/037891 | 5/2003 |
| WO | WO 2003/040131 | 5/2003 |
| WO | WO 2003/042402 | 5/2003 |
| WO | WO 2003/049542 | 6/2003 |
| WO | WO 2003/062236 | 7/2003 |
| WO | WO 2003/075836 | 9/2003 |
| WO | WO 2003/082871 | 10/2003 |
| WO | WO 2003/097609 | 11/2003 |
| WO | WO 2003/099771 | 12/2003 |
| WO | WO 2003/099818 | 12/2003 |
| WO | WO 2003/101985 | 12/2003 |
| WO | WO 2004/002986 | 1/2004 |
| WO | WO 2004/005281 | 1/2004 |
| WO | WO 2004/011465 | 2/2004 |
| WO | WO 2004/014382 | 2/2004 |
| WO | WO 2004/014907 | 2/2004 |
| WO | WO 2004/018472 | 3/2004 |
| WO | WO 2004/020441 | 3/2004 |
| WO | WO 2004/041821 | 5/2004 |
| WO | WO 2004/041822 | 5/2004 |
| WO | WO 2004/041823 | 5/2004 |
| WO | WO 2004/043367 | 5/2004 |
| WO | WO 2004/046120 | 6/2004 |
| WO | WO 2004/046152 | 6/2004 |
| WO | WO 2004/048343 | 6/2004 |
| WO | WO 2004/052291 | 6/2004 |
| WO | WO 2004/052862 | 6/2004 |
| WO | WO 2004/056786 | 7/2004 |
| WO | WO 2004/056822 | 7/2004 |
| WO | WO 2004/056830 | 7/2004 |
| WO | WO 2004/065378 | 8/2004 |
| WO | WO 2004/080980 | 9/2004 |
| WO | WO 2004/083177 | 9/2004 |
| WO | WO 2004/087053 | 10/2004 |
| WO | WO 2004/089955 | 10/2004 |
| WO | WO 2004/094420 | 11/2004 |
| WO | WO 2004/099209 | 11/2004 |
| WO | WO 2004/108139 | 11/2004 |
| WO | WO 2004/110487 | 12/2004 |
| WO | WO 2004/112793 | 12/2004 |
| WO | WO 2004/113307 | 12/2004 |
| WO | WO 2005/007653 | 1/2005 |
| WO | WO 2005/011597 | 2/2005 |
| WO | WO 2005/021533 | 3/2005 |
| WO | WO 2005/028434 | 3/2005 |
| WO | WO 2005/028478 | 3/2005 |
| WO | WO 2005/028480 | 3/2005 |
| WO | WO 2005/028444 | 5/2005 |
| WO | WO 2005/040119 | 5/2005 |
| WO | WO 2005/047289 | 5/2005 |
| WO | WO 2005/056524 | 6/2005 |
| WO | WO 2005/063768 | 6/2005 |
| WO | WO 2005/066162 | 7/2005 |
| WO | WO 2005/070430 | 8/2005 |
| WO | WO 2005/070929 | 8/2005 |
| WO | WO 2005/072412 | 8/2005 |
| WO | WO 2005/073232 | 8/2005 |
| WO | WO 2005/080393 | 9/2005 |
| WO | WO 2005/082903 | 9/2005 |
| WO | WO 2005/085210 | 9/2005 |
| WO | WO 2005/085248 | 9/2005 |
| WO | WO 2005/085249 | 9/2005 |
| WO | WO 2005/087765 | 9/2005 |
| WO | WO 2005/092901 | 10/2005 |
| WO | WO 2005/105097 | 11/2005 |
| WO | WO 2005/113536 | 12/2005 |
| WO | WO 2005/116035 | 12/2005 |
| WO | WO 2005/121130 | 12/2005 |
| WO | WO 2005/121142 | 12/2005 |
| WO | WO 2006/000420 | 1/2006 |
| WO | WO 2006/024486 | 3/2006 |
| WO | WO 2006/024487 | 3/2006 |
| WO | WO 2006/024834 | 3/2006 |
| WO | WO 2006/028289 | 3/2006 |
| WO | WO 2006/030031 | 3/2006 |
| WO | WO 2006/038112 | 4/2006 |
| WO | WO 2006/050076 | 5/2006 |
| WO | WO 2006/050162 | 5/2006 |
| WO | WO 2006/052712 | 5/2006 |
| WO | WO 2006/055752 | 5/2006 |
| WO | WO 2006/024524 | 6/2006 |
| WO | WO 2006/056399 | 6/2006 |
| WO | WO 2006/058120 | 6/2006 |
| WO | WO 2006/062465 | 6/2006 |
| WO | WO 2006/065703 | 6/2006 |
| WO | WO 2006/074293 | 7/2006 |
| WO | WO 2006/087230 | 8/2006 |
| WO | WO 2006/092691 | 9/2006 |
| WO | WO 2006/102588 | 9/2006 |
| WO | WO 2006/102610 | 9/2006 |
| WO | WO 2006/105448 | 10/2006 |
| WO | WO 2006/107644 | 10/2006 |
| WO | WO 2006/112666 | 10/2006 |
| WO | WO 2006/119504 | 11/2006 |
| WO | WO 2006/124462 | 11/2006 |
| WO | WO 2006/124731 | 11/2006 |
| WO | WO 2006/135821 | 12/2006 |
| WO | WO 2006/136442 | 12/2006 |
| WO | WO 2007/013964 | 2/2007 |
| WO | WO 2007/017096 | 2/2007 |
| WO | WO 2007/021795 | 2/2007 |
| WO | WO 2007/022268 | 2/2007 |
| WO | WO 2007/023105 | 3/2007 |
| WO | WO 2007/025949 | 3/2007 |
| WO | WO 2007/030366 | 3/2007 |
| WO | WO 2007/032466 | 3/2007 |
| WO | WO 2007/033780 | 3/2007 |
| WO | WO 2007/038209 | 4/2007 |
| WO | WO 2007/044698 | 4/2007 |
| WO | WO 2007/044729 | 4/2007 |
| WO | WO 2007/048802 | 5/2007 |
| WO | WO 2007/053135 | 5/2007 |
| WO | WO 2007/053452 | 5/2007 |
| WO | WO 2007/053498 | 5/2007 |
| WO | WO 2007/055418 | 5/2007 |
| WO | WO 2007/056023 | 5/2007 |
| WO | WO 2007/056075 | 5/2007 |
| WO | WO 2007/056170 | 5/2007 |
| WO | WO 2007/058392 | 5/2007 |
| WO | WO 2007/058626 | 5/2007 |
| WO | WO 2007/059108 | 5/2007 |
| WO | WO 2007/061554 | 5/2007 |
| WO | WO 2007/064883 | 6/2007 |
| WO | WO 2007/064931 | 6/2007 |
| WO | WO 2007/066189 | 6/2007 |
| WO | WO 2007/067444 | 6/2007 |
| WO | WO 2007/071752 | 6/2007 |

(56) References Cited

FOREIGN PATENT DOCUMENTS

| | | |
|---|---|---|
| WO | WO 2007/084314 | 7/2007 |
| WO | WO 2007/088999 | 8/2007 |
| WO | WO 2007/092879 | 8/2007 |
| WO | WO 2007/093901 | 8/2007 |
| WO | WO 2007/109334 | 9/2007 |
| WO | WO 2007/110868 | 10/2007 |
| WO | WO 2007/112347 | 10/2007 |
| WO | WO 2007/120097 | 10/2007 |
| WO | WO 2007/120339 | 10/2007 |
| WO | WO 2007/125351 | 11/2007 |
| WO | WO 2007/125405 | 11/2007 |
| WO | WO 2007/126841 | 11/2007 |
| WO | WO 2007/134259 | 11/2007 |
| WO | WO 2007/136465 | 11/2007 |
| WO | WO 2007/140957 | 12/2007 |
| WO | WO 2007/143600 | 12/2007 |
| WO | WO 2007/147217 | 12/2007 |
| WO | WO 2008/001070 | 1/2008 |
| WO | WO 2008/003766 | 1/2008 |
| WO | WO 2008/005877 | 1/2008 |
| WO | WO 2008/008234 | 1/2008 |
| WO | WO 2008/008747 | 1/2008 |
| WO | WO 2008/012635 | 1/2008 |
| WO | WO 2008/021389 | 2/2008 |
| WO | WO 2008/021851 | 2/2008 |
| WO | WO 2008/025556 | 3/2008 |
| WO | WO 2008/033858 | 3/2008 |
| WO | WO 2008/033999 | 3/2008 |
| WO | WO 2008/034859 | 3/2008 |
| WO | WO 2008/034860 | 3/2008 |
| WO | WO 2008/037459 | 4/2008 |
| WO | WO 2008/042639 | 4/2008 |
| WO | WO 2008/052898 | 5/2008 |
| WO | WO 2008/052934 | 5/2008 |
| WO | WO 2008/060907 | 5/2008 |
| WO | WO 2008/063583 | 5/2008 |
| WO | WO 2008/063609 | 5/2008 |
| WO | WO 2008/071455 | 6/2008 |
| WO | WO 2008/074068 | 6/2008 |
| WO | WO 2008/075068 | 6/2008 |
| WO | WO 2008/076278 | 6/2008 |
| WO | WO 2008/078091 | 7/2008 |
| WO | WO 2008/078100 | 7/2008 |
| WO | WO 2008/079460 | 7/2008 |
| WO | WO 2008/079933 | 7/2008 |
| WO | WO 2008/085942 | 7/2008 |
| WO | WO 2008/089105 | 7/2008 |
| WO | WO 2008/099075 | 8/2008 |
| WO | WO 2008/107436 | 9/2008 |
| WO | WO 2008/107544 | 9/2008 |
| WO | WO 2008/109181 | 9/2008 |
| WO | WO 2008/109943 | 9/2008 |
| WO | WO 2008/115974 | 9/2008 |
| WO | WO 2008/117269 | 10/2008 |
| WO | WO 2008/118454 | 10/2008 |
| WO | WO 2008/123755 | 10/2008 |
| WO | WO 2008/128141 | 10/2008 |
| WO | WO 2008/130584 | 10/2008 |
| WO | WO 2008/131972 | 11/2008 |
| WO | WO 2008/141065 | 11/2008 |
| WO | WO 2008/142720 | 11/2008 |
| WO | WO 2008/144253 | 11/2008 |
| WO | WO 2008/151184 | 12/2008 |
| WO | WO 2008/153207 | 12/2008 |
| WO | WO 2008/153852 | 12/2008 |
| WO | WO 2008/154221 | 12/2008 |
| WO | WO 2008/156712 | 12/2008 |
| WO | WO 2009/013335 | 1/2009 |
| WO | WO 2009/013354 | 1/2009 |
| WO | WO 2009/097446 | 1/2009 |
| WO | WO 2009/016253 | 2/2009 |
| WO | WO 2009/019518 | 2/2009 |
| WO | WO 2009/021083 | 2/2009 |
| WO | WO 2009/029473 | 3/2009 |
| WO | WO 2009/029625 | 3/2009 |
| WO | WO 2009/030871 | 3/2009 |
| WO | WO 2009/032861 | 3/2009 |
| WO | WO 2009/036012 | 3/2009 |
| WO | WO 2009/044788 | 4/2009 |
| WO | WO 2009/046606 | 4/2009 |
| WO | WO 2009/047255 | 4/2009 |
| WO | WO 2009/047506 | 4/2009 |
| WO | WO 2009/047522 | 4/2009 |
| WO | WO 2009/047993 | 4/2009 |
| WO | WO 2009/049018 | 4/2009 |
| WO | WO 2009/050183 | 4/2009 |
| WO | WO 2009/053737 | 4/2009 |
| WO | WO 2009/055828 | 4/2009 |
| WO | WO 2009/056886 | 5/2009 |
| WO | WO 2009/071535 | 6/2009 |
| WO | WO 2009/073153 | 6/2009 |
| WO | WO 2009/085185 | 7/2009 |
| WO | WO 2009/086130 | 7/2009 |
| WO | WO 2009/086509 | 7/2009 |
| WO | WO 2009/087238 | 7/2009 |
| WO | WO 2009/092764 | 7/2009 |
| WO | WO 2009/093209 | 7/2009 |
| WO | WO 2009/093210 | 7/2009 |
| WO | WO 2009/094528 | 7/2009 |
| WO | WO 2009/099982 | 8/2009 |
| WO | WO 2009/103652 | 8/2009 |
| WO | WO 2009/105717 | 8/2009 |
| WO | WO 2009/108332 | 9/2009 |
| WO | WO 2009/108827 | 9/2009 |
| WO | WO 2009/112826 | 9/2009 |
| WO | WO 2009/114870 | 9/2009 |
| WO | WO 2009/114874 | 9/2009 |
| WO | WO 2009/122180 | 10/2009 |
| WO | WO 2009/123967 | 10/2009 |
| WO | WO 2009/124755 | 10/2009 |
| WO | WO 2009/125808 | 10/2009 |
| WO | WO 2009/125809 | 10/2009 |
| WO | WO 2009/126584 | 10/2009 |
| WO | WO 2009/128520 | 10/2009 |
| WO | WO 2009/131687 | 10/2009 |
| WO | WO 2009/131926 | 10/2009 |
| WO | WO 2009/132980 | 11/2009 |
| WO | WO 2009/133127 | 11/2009 |
| WO | WO 2009/141386 | 11/2009 |
| WO | WO 2009/144205 | 12/2009 |
| WO | WO 2009/144302 | 12/2009 |
| WO | WO 2009/146034 | 12/2009 |
| WO | WO 2009/148916 | 12/2009 |
| WO | WO 2009/150150 | 12/2009 |
| WO | WO 2009/150240 | 12/2009 |
| WO | WO 2009/151997 | 12/2009 |
| WO | WO 2009/153592 | 12/2009 |
| WO | WO 2009/157423 | 12/2009 |
| WO | WO 2010/006947 | 1/2010 |
| WO | WO 2010/007099 | 1/2010 |
| WO | WO 2010/007116 | 1/2010 |
| WO | WO 2010/009155 | 1/2010 |
| WO | WO 2010/009195 | 1/2010 |
| WO | WO 2010/009207 | 1/2010 |
| WO | WO 2010/009735 | 1/2010 |
| WO | WO 2010/015643 | 2/2010 |
| WO | WO 2010/017047 | 2/2010 |
| WO | WO 2010/019210 | 2/2010 |
| WO | WO 2010/019899 | 2/2010 |
| WO | WO 2010/030027 | 3/2010 |
| WO | WO 2010/036959 | 4/2010 |
| WO | WO 2010/038081 | 4/2010 |
| WO | WO 2010/045371 | 4/2010 |
| WO | WO 2010/049731 | 5/2010 |
| WO | WO 2010/051043 | 5/2010 |
| WO | WO 2010/052448 | 5/2010 |
| WO | WO 2010/059552 | 5/2010 |
| WO | WO 2010/059658 | 5/2010 |
| WO | WO 2010/062571 | 6/2010 |
| WO | WO 2010/064621 | 6/2010 |
| WO | WO 2010/064875 | 6/2010 |
| WO | WO 2010/067886 | 6/2010 |
| WO | WO 2010/067888 | 6/2010 |
| WO | WO 2010/075074 | 7/2010 |

(56) References Cited

FOREIGN PATENT DOCUMENTS

| | | |
|---|---|---|
| WO | WO 2010/077647 | 7/2010 |
| WO | WO 2010/077680 | 7/2010 |
| WO | WO 2010/078421 | 7/2010 |
| WO | WO 2010/078427 | 7/2010 |
| WO | WO 2010/080503 | 7/2010 |
| WO | WO 2010/080712 | 7/2010 |
| WO | WO 2010/083145 | 7/2010 |
| WO | WO 2010/083283 | 7/2010 |
| WO | WO 2010/086089 | 8/2010 |
| WO | WO 2010/089411 | 8/2010 |
| WO | WO 2010/092181 | 8/2010 |
| WO | WO 2010/099938 | 9/2010 |
| WO | WO 2010/103306 | 9/2010 |
| WO | WO 2010/104047 | 9/2010 |
| WO | WO 2010/107765 | 9/2010 |
| WO | WO 2010/107768 | 9/2010 |
| WO | WO 2010/111303 | 9/2010 |
| WO | WO 2010/111573 | 9/2010 |
| WO | WO 2010/115279 | 10/2010 |
| WO | WO 2010/117425 | 10/2010 |
| WO | WO 2010/119284 | 10/2010 |
| WO | WO 2010/119285 | 10/2010 |
| WO | WO 2010/117323 | 11/2010 |
| WO | WO 2010/125216 | 11/2010 |
| WO | WO 2010/126960 | 11/2010 |
| WO | WO 2010/127212 | 11/2010 |
| WO | WO 2010/129509 | 11/2010 |
| WO | WO 2010/136031 | 12/2010 |
| WO | WO 2010/142801 | 12/2010 |
| WO | WO 2010/151689 | 12/2010 |
| WO | WO 2011/002038 | 1/2011 |
| WO | WO 2011/007819 | 1/2011 |
| WO | WO 2011/011597 | 1/2011 |
| WO | WO 2011/012816 | 2/2011 |
| WO | WO 2011/014535 | 2/2011 |
| WO | WO 2011/015037 | 2/2011 |
| WO | WO 2011/016472 | 2/2011 |
| WO | WO 2011/016528 | 2/2011 |
| WO | WO 2011/018894 | 2/2011 |
| WO | WO 2011/022439 | 2/2011 |
| WO | WO 2011/026579 | 3/2011 |
| WO | WO 2011/028947 | 3/2011 |
| WO | WO 2011/031740 | 3/2011 |
| WO | WO 2011/032050 | 3/2011 |
| WO | WO 2011/039344 | 4/2011 |
| WO | WO 2011/041143 | 4/2011 |
| WO | WO 2011/042389 | 4/2011 |
| WO | WO 2011/042474 | 4/2011 |
| WO | WO 2011/045344 | 4/2011 |
| WO | WO 2011/049825 | 4/2011 |
| WO | WO 2011/049988 | 4/2011 |
| WO | WO 2011/050245 | 4/2011 |
| WO | WO 2011/051425 | 5/2011 |
| WO | WO 2011/053518 | 5/2011 |
| WO | WO 2011/054843 | 5/2011 |
| WO | WO 2011/055911 | 5/2011 |
| WO | WO 2011/057022 | 5/2011 |
| WO | WO 2011/060295 | 5/2011 |
| WO | WO 2011/062253 | 5/2011 |
| WO | WO 2011/062885 | 5/2011 |
| WO | WO 2011/063159 | 5/2011 |
| WO | WO 2011/066342 | 6/2011 |
| WO | WO 2011/068899 | 6/2011 |
| WO | WO 2011/071821 | 6/2011 |
| WO | WO 2011/075515 | 6/2011 |
| WO | WO 2011/075620 | 6/2011 |
| WO | WO 2011/077043 | 6/2011 |
| WO | WO 2011/077044 | 6/2011 |
| WO | WO 2011/079231 | 6/2011 |
| WO | WO 2011/080755 | 7/2011 |
| WO | WO 2011/082234 | 7/2011 |
| WO | WO 2011/082266 | 7/2011 |
| WO | WO 2011/082267 | 7/2011 |
| WO | WO 2011/082400 | 7/2011 |
| WO | WO 2011/082488 | 7/2011 |
| WO | WO 2011/087776 | 7/2011 |
| WO | WO 2011/090666 | 7/2011 |
| WO | WO 2011/090738 | 7/2011 |
| WO | WO 2011/090760 | 7/2011 |
| WO | WO 2011/093672 | 8/2011 |
| WO | WO 2011/094890 | 8/2011 |
| WO | WO 2011/097717 | 8/2011 |
| WO | WO 2011/101409 | 8/2011 |
| WO | WO 2011/101806 | 8/2011 |
| WO | WO 2011/102441 | 8/2011 |
| WO | WO 2011/103196 | 8/2011 |
| WO | WO 2011/103441 | 8/2011 |
| WO | WO 2011/103460 | 8/2011 |
| WO | WO 2011/103557 | 8/2011 |
| WO | WO 2011/105161 | 9/2011 |
| WO | WO 2011/109237 | 9/2011 |
| WO | WO 2011/111880 | 9/2011 |
| WO | WO 2011/112687 | 9/2011 |
| WO | WO 2011/112995 | 9/2011 |
| WO | WO 2011/115725 | 9/2011 |
| WO | WO 2011/119894 | 9/2011 |
| WO | WO 2011/120327 | 10/2011 |
| WO | WO 2011/123493 | 10/2011 |
| WO | WO 2011/128403 | 10/2011 |
| WO | WO 2011/130390 | 10/2011 |
| WO | WO 2011/133722 | 10/2011 |
| WO | WO 2011/133750 | 10/2011 |
| WO | WO 2011/133888 | 10/2011 |
| WO | WO 2011/135376 | 11/2011 |
| WO | WO 2011/137313 | 11/2011 |
| WO | WO 2011/140338 | 11/2011 |
| WO | WO 2011/141756 | 11/2011 |
| WO | WO 2011/141848 | 11/2011 |
| WO | WO 2011/143033 | 11/2011 |
| WO | WO 2011/143318 | 11/2011 |
| WO | WO 2011/143430 | 11/2011 |
| WO | WO 2011/147198 | 12/2011 |
| WO | WO 2011/147199 | 12/2011 |
| WO | WO 2011/151360 | 12/2011 |
| WO | WO 2011/153553 | 12/2011 |
| WO | WO 2011/155983 | 12/2011 |
| WO | WO 2011/156610 | 12/2011 |
| WO | WO 2011/159877 | 12/2011 |
| WO | WO 2011/161699 | 12/2011 |
| WO | WO 2011/163330 | 12/2011 |
| WO | WO 2012/000103 | 1/2012 |
| WO | WO 2012/003544 | 1/2012 |
| WO | WO 2012/004217 | 1/2012 |
| WO | WO 2012/004731 | 1/2012 |
| WO | WO 2012/004732 | 1/2012 |
| WO | WO 2012/008563 | 1/2012 |
| WO | WO 2012/008564 | 1/2012 |
| WO | WO 2012/008999 | 1/2012 |
| WO | WO 2012/009258 | 1/2012 |
| WO | WO 2012/009309 | 1/2012 |
| WO | WO 2012/013619 | 2/2012 |
| WO | WO 2012/015274 | 2/2012 |
| WO | WO 2012/019093 | 2/2012 |
| WO | WO 2012/020133 | 2/2012 |
| WO | WO 2012/027236 | 3/2012 |
| WO | WO 2012/027239 | 3/2012 |
| WO | WO 2012/030990 | 3/2012 |
| WO | WO 2012/031004 | 3/2012 |
| WO | WO 2012/032031 | 3/2012 |
| WO | WO 2012/032065 | 3/2012 |
| WO | WO 2012/032067 | 3/2012 |
| WO | WO 2012/032334 | 3/2012 |
| WO | WO 2012/035996 | 3/2012 |
| WO | WO 2012/036233 | 3/2012 |
| WO | WO 2012/038743 | 3/2012 |
| WO | WO 2012/047699 | 4/2012 |
| WO | WO 2012/054364 | 4/2012 |
| WO | WO 2012/057260 | 5/2012 |
| WO | WO 2012/058211 | 5/2012 |
| WO | WO 2012/061156 | 5/2012 |
| WO | WO 2012/061337 | 5/2012 |
| WO | WO 2012/062462 | 5/2012 |
| WO | WO 2012/063207 | 5/2012 |
| WO | WO 2012/064715 | 5/2012 |

(56) References Cited

FOREIGN PATENT DOCUMENTS

| | | |
|---|---|---|
| WO | WO 2012/065297 | 5/2012 |
| WO | WO 2012/065546 | 5/2012 |
| WO | WO 2012/066578 | 5/2012 |
| WO | WO 2012/068343 | 5/2012 |
| WO | WO 2012/073017 | 6/2012 |
| WO | WO 2012/078777 | 6/2012 |
| WO | WO 2012/080727 | 6/2012 |
| WO | WO 2012/080729 | 6/2012 |
| WO | WO 2012/083866 | 6/2012 |
| WO | WO 2012/083953 | 6/2012 |
| WO | WO 2012/083954 | 6/2012 |
| WO | WO 2012/084704 | 6/2012 |
| WO | WO 2012/087784 | 6/2012 |
| WO | WO 2012/088266 | 6/2012 |
| WO | WO 2012/091240 | 7/2012 |
| WO | WO 2012/093731 | 7/2012 |
| WO | WO 2012/098068 | 7/2012 |
| WO | WO 2012/101239 | 8/2012 |
| WO | WO 2012/106995 | 8/2012 |
| WO | WO 2012/112961 | 8/2012 |
| WO | WO 2012/112965 | 8/2012 |
| WO | WO 2012/116237 | 8/2012 |
| WO | WO 2012/125812 | 9/2012 |
| WO | WO 2012/127012 | 9/2012 |
| WO | WO 2012/129344 | 9/2012 |
| WO | WO 2012/134943 | 10/2012 |
| WO | WO 2012/138975 | 10/2012 |
| WO | WO 2012/140114 | 10/2012 |
| WO | WO 2012/158704 | 11/2012 |
| WO | WO 2012/158795 | 11/2012 |
| WO | WO 2012/158994 | 11/2012 |
| WO | WO 2012/161812 | 11/2012 |
| WO | WO 2012/167247 | 12/2012 |
| WO | WO 2012/173370 | 12/2012 |
| WO | WO 2013/016197 | 1/2013 |
| WO | WO 2013/024002 | 2/2013 |
| WO | WO 2013/024895 | 2/2013 |
| WO | WO 2013/033981 | 3/2013 |
| WO | WO 2013/039854 | 3/2013 |
| WO | WO 2013/041634 | 3/2013 |
| WO | WO 2013/049352 | 4/2013 |
| WO | WO 2013/053051 | 4/2013 |
| WO | WO 2013/063000 | 5/2013 |
| WO | WO 2013/063003 | 5/2013 |
| WO | WO 2013/108809 | 7/2013 |
| WO | WO 2013/109027 | 7/2013 |
| WO | WO 2013/124316 | 8/2013 |
| WO | WO 2013/136249 | 9/2013 |
| WO | WO 2013/144339 | 10/2013 |
| WO | WO 2014/007951 | 1/2014 |
| WO | WO 2014/011284 | 1/2014 |
| WO | WO 2014/011900 | 1/2014 |
| WO | WO 2014/019186 | 2/2014 |
| WO | WO 2014/022528 | 2/2014 |
| WO | WO 2014/026125 | 2/2014 |
| WO | WO 2014/044846 | 3/2014 |
| WO | WO 2014/048878 | 4/2014 |
| WO | WO 2014/062454 | 4/2014 |
| WO | WO 2014/085216 | 5/2014 |
| WO | WO 2014/089913 | 6/2014 |
| WO | WO 2014/105849 | 7/2014 |
| WO | WO 2014/113191 | 7/2014 |
| WO | WO 2014/136972 | 9/2014 |
| WO | WO 2014/138485 | 9/2014 |
| WO | WO 2014/140184 | 9/2014 |
| WO | WO 2014/144737 | 9/2014 |
| WO | WO 2014/160160 | 10/2014 |
| WO | WO 2014/160478 | 10/2014 |
| WO | WO 2014/160521 | 10/2014 |
| WO | WO 2014/162039 | 10/2014 |
| WO | WO 2014/170063 | 10/2014 |
| WO | WO 2014/171755 | 10/2014 |
| WO | WO 2014/172644 | 10/2014 |
| WO | WO 2014/174307 | 10/2014 |
| WO | WO 2014/182829 | 11/2014 |
| WO | WO 2014/198942 | 12/2014 |
| WO | WO 2014/206343 | 12/2014 |
| WO | WO 2014/206344 | 12/2014 |
| WO | WO 2015/000715 | 1/2015 |
| WO | WO 2015/006492 | 1/2015 |
| WO | WO 2015/006754 | 1/2015 |
| WO | WO 2015/030021 | 3/2015 |
| WO | WO 2015/057938 | 4/2015 |
| WO | WO 2015/057963 | 4/2015 |
| WO | WO 2015/059668 | 4/2015 |
| WO | WO 2015/061572 | 4/2015 |
| WO | WO 2015/066452 | 5/2015 |
| WO | WO 2015/108992 | 7/2015 |
| WO | WO 2016/064960 | 4/2016 |
| WO | WO 2016/134314 | 8/2016 |
| WO | WO 2016/192680 | 12/2016 |
| WO | WO 2017/023972 | 2/2017 |
| WO | WO 2017/023988 | 2/2017 |
| WO | WO 2017/023989 | 2/2017 |
| WO | WO 2017/024003 | 2/2017 |
| WO | WO 2017/024004 | 2/2017 |
| WO | WO 2017/024015 | 2/2017 |
| WO | WO 2017/024025 | 2/2017 |
| WO | WO 2017/028314 | 2/2017 |
| WO | WO 2017/223414 | 12/2017 |
| WO | WO 2018/041091 | 3/2018 |
| WO | WO 2018/049214 | 3/2018 |
| WO | WO 2018/067512 | 4/2018 |
| WO | WO 2018/093029 | 5/2018 |
| WO | WO 2018/093215 | 5/2018 |
| WO | WO 2018/105972 | 6/2018 |
| WO | WO 2018/105973 | 6/2018 |
| WO | WO 2018/234354 | 12/2018 |
| WO | WO 2019/037640 | 2/2019 |
| WO | WO 2019/079369 | 4/2019 |
| WO | WO 2019/105886 | 6/2019 |
| WO | WO 2019/213506 | 11/2019 |
| WO | WO 2020/049017 | 3/2020 |
| WO | WO 2020/081898 | 4/2020 |
| WO | WO 2020/131627 | 6/2020 |
| WO | WO 2020/131674 | 6/2020 |

OTHER PUBLICATIONS

Eurasian Office Action in Eurasian Application No. 202091923, dated Jul. 27, 2021, 6 pages (English Translation).
Eurasian Office Action in Eurasian Application No. 201992794, dated Sep. 17, 2021, 7 pages.
Eurasian Office Action in Eurasian Application No. 202190877, dated Oct. 6, 2021, 4 pages.
European Office Action in European Application No. 19724676.2, dated Aug. 26, 2021, 5 pages.
European Office Action in European Application No. 19724670.5, dated Nov. 9, 2021, 4 pages.
Ezzat et al., "Dual Inhibition of RET and FGFR4 Restrains Medullary Thyroid Cancer Cell Growth," Clinical Cancer Research, 2005, 11:1336-1341.
Goyal et al,. "Polyclonal Secondary FGFR2 Mutations Drive Acquired Resistance to FGFR Inhibition in Patients with FGFR2 Fusion-Positive Cholangiocarcinoma," Cancer Discov., 2016, 7(3):252-263.
International Preliminary Report on Patentability in International Application No. PCT/US2020/021313, dated Aug. 25, 2021, 11 pages.
International Search Report and Written Opinion in International Application No. PCT/US2020/055735, dated Dec. 15, 2020, 16 pages.
Japanese Office Action in Japanese Application No. 2020-069604, dated Nov. 15, 2021, 7 pages.
Korean Office Action in Korean Application No. 10-2021-7018897, dated Oct. 1, 2021, 15 pages.
Philippine Office Action in Philippine Application No. 1/2015/502383, dated Nov. 11, 2021, 4 pages.
Staerk et al., "Pan-Src Family Kinase Inhibitors Replace Sox2 during the Direct Reprogramming of Somatic Cells," Angewandte Chem., Jun. 14, 2011, 50(25):5734-5736.

(56) References Cited

OTHER PUBLICATIONS

Taiwan Office Action in Taiwan Application No. 109132389, dated Aug. 23, 2021, 4 pages.
Ukraine Office Action in Ukraine Application No. a201801562, dated Jul. 28, 2021, 9 pages.
Ye et al., "Combination of the FGFR4 inhibitor PD173074 and 5-fluorouracil reduces proliferation and promotes apoptosis in gastric cancer," Oncol Rep., Dec. 2013, 30(6):2777-2784.
"Sabiosciences.com" [online]. "FGF Pathway," 2000-2012, [retrieved on Jun. 23, 2015]. Retrieved from the Internet: URL <http://www.sabiosciences.com/pathway.php?sn=FGF_Signaling>, 3 pages.
"Substance Record for SID 240993001," Feb. 13, 2015, pp. 1-8.
Acevedo et al., "Inducible FGFR-1 Activation Leads to Irreversible Prostate Adenocarcinoma and an Epithelial-to-Mesenchymal Transition," Cancer Cell, Dec. 2007, 12: 559-571.
Ali et al., "Synthesis and structure activity relationship of substituted N,6-diphenyl-5,6-dihydrobenzo[h]quinazolin-2-amine as inhibitors of fibroblast growth factor receptors (FGFR)" Cancer Res, Apr. 15, 2012, 72; 3905.
Angevin et al., "TKI258 (dovitinib lactate) in metastatic renal cell carcinoma (mRCC) patients refractory to approved targeted therapies: A phase I/II dose finding and biomarker study," Journal of Clinical Oncology, May 20, 2009, 27:15S, 1 page.
Antonios-Mccrea et al., "LHMDS mediated tandem acylation-cyclization of 2-aminobenzenecarbonitriles with 2-benzymidazol-2-ylacetates: a short and efficient route to the synthesis of 4-amino-3-benzimidazol-2-ylhydroquinolin-2-ones," Tetrahedron Letters, 2006, 657-660.
Anonymous, "American Society for Clinical Pharmacology and Therapeutics," Clin Pharma and Thera., Feb. 13, 2019, 105(S1):S5-S121.
Anonymous, "In Vitro Metabolism- and Transporter- Mediated Drug-Drug Interaction Studies Guidance for Industry", Clinical Pharmacology, Oct. 2017, 47 pages.
Arai et al., "Characterization of the cell or origin and propagation potential of the fibroblast growth factor 9-induced mouse model of lung adenocarcinoma," J. Pathol., Mar. 2015, 235(4): 593-605.
Arai et al., "Fibroblast growth factor receptor 2 tyrosine kinase fusions define a unique molecular subtype of cholangiocarcinoma," Hepatology, 2014, 59(4):1427-1434.
Argentina Office Action in Argentina Application No. 20130102068, dated Jul. 17, 2020, 10 pages.
Argentina Office Action in Argentina Application No. 20140101651, dated Nov. 21, 2019, 5 pages.
Argentina Office Action in Argentina Application No. 20140101651, dated Jul. 29, 2021, 9 pages.
Atzrodt et al., "The Renaissance of H/D Exchange," Angew Chem Int Ed., 2007, 7744-7765.
Australian Office Action in Australian Application No. 2013287176, dated Sep. 12, 2017, 4 pages.
Australian Office Action in Australian Application No. 2014253798, dated Jul. 31, 2017, 4 pages.
Australian Office Action in Australian Application No. 2016219816, dated Aug. 26, 2019, 3 pages.
Australian Office Action in Australian Application No. 2016219822, dated Jul. 8, 2019, 4 pages.
Australian Office Action in Australian Application No. 2018208772, dated Jul. 1, 2018, 5 pages.
Australian Office Action in Australian Application No. 2019200066, dated Aug. 27, 2019, 6 pages.
Avet-Loiseau et al., "Impact of high-risk cytogenetics and prior therapy on outcomes in patients with advanced relapsed or refractory multiple myeloma treated with lenalidomide plus dexamethasone," Leukemia, 2010, 623-628.
Bai et al., "GP369, an FGFR2-IIIb specific antibody, exhibits potent antitumor activity against human cancers driven by activated FGFR2 signaling," Am. Assoc. for Cancer Research, Aug. 17, 2010, 30 pages.
Bansal et al., "Specific inhibitor of FGF receptor signaling: FGF-2-mediated effects on proliferation, differentiation, and MAPK activation are inhibited by PD 173074 in oligodendrocyte-lineage cells," J. Neurosci. Res., 2003, 74: 486.
Bavin, "Polymorphism in Process Development," Chemistry & Industry, Society of Chemical Industry, Aug. 1989, 527-529.
Bazyl et al., "The selective ortho-methoxylation of pentafluorobenzoic acid—a new way to tetrafluorosalicylic acid and its derivatives," J Flour Chem., Feb. 11, 1999, 94(1):11-13.
Beekman et al., "New Molecular Targets and Novel Agents in the Treatment of Advanced Urothelial Cancer," Semin Oncol, 2007, 34: 154-164.
Bello et al., "E-3810 is a potent dual inhibitor of VEGFR and FGFR that exerts antitumor activity in multiple preclinical models," Cancer Res, 2011.
Bello et al., "E-3810 is a potent dual inhibitor of VEGFR and FGFR that exerts antitumor activity in multiple preclinical models," Cancer Res, 2011, Supplemental figures, 4 pages.
Bello et al., "E-3810 is a potent dual inhibitor of VEGFR and FGFR that exerts antitumor activity in multiple preclinical models," Cancer Res, 2011, Supplemental table, 3 pages.
Bello et al., "E-3810 is a potent dual inhibitor of VEGFR and FGFR that exerts antitumor activity in multiple preclinical models," Cancer Res, 2011, Supplementary data, 4 pages.
Benet-Pages et al., "An FGF23 missense mutation causes familial tumoral calcinosis with hyperphosphatemia," Human Molecular Genetics, 2005, 14(3):385-390.
Berge et al., "Pharmaceutical Salts", Journal of Pharmaceutical Science, 1977, 66(2):1-19.
Bergwitz and Juppner, "Regulation of Phosphate Homeostasis by PTH, Vitamin D, and FGF23," Annu. Rev. Med., 2010, 61:91-104.
Bhide et al., "Discovery and Preclinical Studies of (R )-1-(4-(4-Fluoro-2-methyl-1H-indol-5-yloxy)-5-methylpyrrolo[2,1-fl[1,2,4]triazin-6-yloxy)propan-2-ol (BMS-540215), an In Vivo Active Potent VEGFR-2 Inhibitor," Journal of Medicinal Chemistiy, 2006, 49(7): 2143-2146.
Billerey et al., "Frequent FGFR3 Mutations in Papillary Non-Invasive Bladder (pTa) Tumors," American Journal of Pathology, Jun. 2001, 158(6): 1955-1959.
Billottet et al., "Targets of Fibroblast Growth Factor 1 (FGF-1) and FGF-2 Signaling Involved in the Invasive and Tumorigenic Behavior of Carchinoma Cells," Molecular Biology of the Cell, Oct. 2004, 15: 4725-4734.
Biocentury, Week of Nov. 10, 2014, 52 pages.
Bisping et al., "Bortezomib, Dexamethasone, and Fibroblast Growth Factor Receptor 3-Specific Tyrosine Kinase Inhibitor in t(4;14) Myeloma," Clin Cancer Res, Jan. 2009, 15(2):520-531.
Black et al., "Targeted therapies in bladder cancer—an update," Urologic Oncology: Seminars and Original Investigations, 2007, 433-438.
Blom et al., "Optimizing Preparative LC-MS Configurations and Methods for Parallel Synthesis Purification", J Combi Chem., 2003, 5:670.
Blom et al., Preparative LC-MS Purification: Improved Compound Specific Method Optimization, J Combi Chem. 2004, 6(6):874-883.
Blom, K., "Two-Pump at Column Dilution Configuration for Preparative LC-MS", J Combi Chem., 2002, 4:295.
Bonaventure et al., "Common Mutations in the Fibroblast Growth Factor Receptor 3 (FRFR3) Gene Account for Achondroplasia, Hypochondroplasia and Thanatophoric Dwarfism," Clin Pediatr Endocrinol, 1997, 105-113.
Bono et al., "Inhibition of Tumor Angiogenesis and Growth by a Small-Molecule Multi-FGF Receptor Blocker with Allosteric Properties," Cancer Cell, Apr. 2013, 477-488.
Borad et al., "Fibroblast growth factor receptor 2 fusions as a target for treating cholangiocarcinoma," Currrent opinion in Gastroenterology, May 2015, 31(3):264-268.
Brooks et al., "Fibroblast growth factor signaling: a new therapeutic opportunity in cancer," Clinical Cancer Research, 2012, 1-23.
Caira, "Crystalline Polymorphism of Organic Compounds," Topics in Current Chemistry, Jan. 1, 1998, 198:163-208.
Cancer [online], [retrieved on Jul. 6, 2007] Retrieved from the Internet, URL: http://www.nlm.nih.gov/medlineplus/cancer.html.
Capelletti et al., "Identification of Recurrent FGFR3-TACC3 Fusion Oncogenes from Lung Adenocarcinoma," AACR Journals, 2014, 6551-6558.

(56) References Cited

OTHER PUBLICATIONS

Cappellen et al., "Frequent activating mutations of FGFR3 in human bladder and cervix carcinomas," Nature Genetics, Sep. 1999, 23: 18-20.

Carmichael et al., "Familial Tumoral Calcinosis: A Forty-Year Follow-up on One Family," The Journal of Bone & Joint Surgery, 2009, 664-671.

Cha et al., "Aberrant Receptor Internalization and Enhanced FRS2-dependent Signaling Contribute to the Transforming Activity of the Fibroblast Growth Factor Receptor 2 IIIb C3 Isoform," The Journal of Biological Chemistry, Mar. 2009, 284(10): 6227-6240.

Chandrani et al., "Drug-sensitive FGFR3 mutations in lung adenocarcinoma," Annals of Oncology, 2017, 28: 597-603.

Chase et al., "Activity of TKI258 against primary cells and cell lines with FGFR1 fusion genes associated with the 8p11 myeloproliferative syndryome," Blood, 2007, 110:3729-3734.

Chefetz and Sprecher, "Familial tumoral calcinosis and the role of O-glycosylation in the maintenance of phosphate homeostasis," Biochimica et Biophysica Acta, 2009, 847-852.

Chefetz et al., "A novel homozygous missense mutation in FGF23 causes Familial Tumoral Calcinosis associated with disseminated visceral calcification," Hum Genet, 2005, 118:261-266.

Chell et al., "Tumour cell responses to new fibroblast growth factor receptor tyrosine kinase inhibitors and identification of a gatekeeper mutation in FGFR3 as a mechanism of acquired resistance," Oncogene, 2012, 1-12.

Chen et al., "Acenaphtho[1,2-b]pyrrole-Based Selective Fibroblast Growth Factor Receptors 1 (FRGR1) Inhibitors: Design, Synthesis, and Biological Activity," Jounal of Medicinal Chemistry, 2011, 54: 3732-3745.

Chen et al., "FGFR3 as a therapeutic target of the small molecule inhibitor PKC412 in hematopoietic malignancies," Oncogene, 2005, 24: 8259-8267.

Chen et al., "Genome-Wide Loss of Heterozygosity and DNA Copy Number Aberration in HPV-Negative Oral Squamous Cell Carcinoma and Their Associations with Disease-Specific Survival," PLoS One, Aug. 2015, 23 pages.

Chesi et al., "Activated fibroblast growth factor receptor 3 is an oncogene that contributes to tumor progression in multiple myeloma," Blood, 2001, 97:729-736.

Chesi et al., "Frequent translocation t(4;14)(p16.3;q32.3) in multiple myeloma is associated with increased expression and activating mutations of fibroblast growth factor receptor 3," Nature Genetics, 1997, 260-264.

Chilean Office Action in Chilean Application No. 1984-2017, dated Sep. 12, 2019, 9 pages.

Chilean Office Action in Chilean Application No. 2015-003089, dated Apr. 24, 2017, 13 pages (English Summary).

Chilean Office Action in Chilean Application No. 2015-003089, dated Jan. 23, 2018, 8 pages.

Chilean Office Action in Chilean Application No. 2122-2017, dated Apr. 22, 2019, 25 pages.

Chilean Office Action in Chilean Application No. 2122-2017, dated Nov. 15, 2019, 15 pages.

Chilean Office Action in Chilean Application No. 3355-2014, dated Jan. 18, 2017, 17 pages (with English translation).

Chilean Office Action in Chilean Application No. 3439-2019, dated Feb. 10, 2021, 26 pages.

Chilean Opposition in Chilean Application No. 3355-2014, 3 pages (English translation only).

Chinese Office Action in Chinese Application No. 10874686.0, dated Oct. 8, 2019, 10 pages.

Chinese Office Action in Chinese Application No. 201380041027.9, dated Feb. 13, 2017, 10 pages (with English translation).

Chinese Office Action in Chinese Application No. 201380041027.9, dated Jul. 12, 2016, 11 pages (with English translation).

Chinese Office Action in Chinese Application No. 201380041027.9, dated Oct. 28, 2015, 17 pages (with English translation).

Chinese Office Action in Chinese Application No. 201480028858.7, dated Apr. 4, 2018, 10 pages (English Translation).

Chinese Office Action in Chinese Application No. 201480028858.7, dated Aug. 19, 2016, 18 pages (English Translation).

Chinese Office Action in Chinese Application No. 201480028858.7, dated Jul. 12, 2017, 10 pages (English Translation).

Chinese Office Action in Chinese Application No. 201680011332.7, dated Aug. 5, 2019, 14 pages.

Chinese Office Action in Chinese Application No. 201680011348.8, dated Aug. 2, 2019, 14 pages.

Chinese Office Action in Chinese Application No. 201710395346.X, dated Jan. 22, 2019, 17 pages.

Chinese Office Action in Chinese Application No. 201710395346.X, dated Sep. 9, 2019, 10 pages.

Chinese Office Action in Chinese Application No. 201710874686.0, dated Feb. 25, 2019, 17 pages.

Chinese Office Action in Chinese Application No. 201910023729.3, dated Mar. 3, 2021, 15 pages.

Chng et al., "Translocation t(4;14) retains prognostic significance even in the setting of high-risk molecular signature," Leukemia, 2008, 2: 459-461.

Chuaqui et al., "Interaction Profiles of Protein Kinase—Inhibitor Complexes and Their Application to Virtual Screening," J. Med. Chem., 2005, 48: 121-133.

Ciappetti and Geithlen "Molecular Variations Based on Isosteric Replacements," The Practice of Medicinal Chemistry, 2008, Chapter 15, pp. 290-341.

ClinicalTrials.gov, "A Study to Evaluate the Efficacy and Safety of Pemigatinib Versus Cherrotherapy in Unresectable or Metastatic Chol (FIGHT-302)," NCT03656536, Mar. 6, 2019, retrieved from URL <https://www.clinicaltrials.gov/ct2/history/NCT03656536?V_5=View#StudyPageTop,>, 4 pages.

Cole et al., "Inhibition of FGFR2 and FGFR1 increases cisplatin sensitivity in ovarian cancer," Cancer Biol. Therapy, Sep. 1, 2010, 10(5):495-504.

Coleman, "Positive and negative regulation of cellular sensitivity to anti-cancer drugs by FGF-2," Drug Resistance Updates, 2003, 85-94.

Colombian Office Action in Colombian Application No. 14-275934-6, dated May 31, 2016, 3 pages (English translation only).

Colombian Office Action in Colombian Application No. 14-275934-6, dated Nov. 17, 2015, 12 pages (English translation only).

Colombian Office Action in Colombian Application No. 16100866, dated Aug. 10, 2017, 9 pages.

Colombian Office Action in Colombian Application No. NC2017/0008795, dated Nov. 29, 2018, 8 pages.

Colombian Office Action in Colombian Application No. NC2017/0008795, dated Aug. 16, 2019, 6 pages.

Colombian Office Action in Colombian Application No. NC2017/0008795, dated Aug. 29, 2017, 2 pages.

Colombian Office Action in Colombian Application No. NC2017/0008824, dated Aug. 31, 2017, 3 pages.

Colombian Office Action in Colombian Application No. NC2017/0008824, dated Nov. 29, 2018, 8 pages.

Colombian Office Action in Colombian Application No. NC2019/0009690, dated Jan. 22, 2020, 20 pages.

Colombian Opposition in Colombian Application No. NC 2021/0004568, dated Apr. 15, 2021, 21 pages.

Cordovilla et al., "The Stille Reaction, 38 Years Later," ACS Catal., Apr. 17, 2015, 5(5):3040-3053.

Corre et al., "Synthesis and biological evaluation of a triazole-based library of pyrido[2,3-d/pyrimidines as FGFR3 tyrosine kinase inhibitors," Organic & Biomolecular Chemistry, 2010, 8:2164-2173.

Costa Rican Office Action in Costa Rican Application No. 2014-0577, dated Apr. 15, 2020, 18 pages.

Costa Rican Office Action in Costa Rican Application No. 2014-0577, dated Jun. 13, 2019, 17 pages.

Costa Rican Office Action in Costa Rican Application No. 2015-0578, dated Jun. 11, 2020, 15 pages.

Costa Rican Opposition in Costa Rican Application No. PCT/US2013/045309, dated Jun. 29, 2015, 14 pages (English Translation).

Covic et al., "Vascular calcification in chronic kidney disease," Clinical Science, 2010, 119: 111-121.

(56) References Cited

OTHER PUBLICATIONS

Crose et al., "FGFR4 Blockade Exerts Distinct Antitumorigenic Effects in Human Embryonal versus Alveolar Rhabdomyosarcoma," Clin Cancer Res., 2012, 18:3780-3790.
Dailey et al., "Mechanisms underlying differential responses to FGF signaling," Cytokine & Growth Factor Reviews, 2005, 233-247.
Dash et al., "A Role for Neoadjuvant Gemcitabine Plus Cisplatin in Muscle-Invasive Urothelial Carcinoma o the Bladder: A Retrospective Experience," Cancer, 2008, 113(9): 2471-2477.
Desnoyers et al., "Targeting FGF19 inhibits tumor growth in colon cancer xenograft and FGF19 transgenic hepatocellular carcinoma models," Oncogene, 2008, 27:85-97.
Dey et al., "Targeting Fibroblast Growth Factor Receptors Blocks PI3K/AKT Signaling, Induces Apoptosis, and Impairs Mammary Tumor Outgrowth and Metastasis," Cancer Research, 2010, 4151-4162.
Dieci et al., "Fibroblast Growth Factor Receptor Inhibitors as a Cancer Treatment: From a Biologic Rationale to Medical Perspectives," Cancer Discovery, 2013, 1-16.
Dienstmann et al., "Genomic aberrations in the FGFR pathway: opportunities for targeted therapies in solid tumors," Annals of Oncology, 2013, 1-12.
Diller and Li, "Kinases, Homology Models, and High Throughput Docking," J. Med. Chem., 2003, 46: 4638-4647.
Dimopoulos et al., "Lenalidomide plus Dexamethasone for Relapsed or Refractory Multiple Myeloma," The New England Journal of Medicine, 2007, 357:2123-2132.
Ding et al., "Somatic mutations affect key pathways in lung adenocarcinoma," Nature., Oct. 23, 2008, 455:1069-1075.
Dovedi and Davies, "Emerging targeted therapies forbladder cancer: a disease waiting for a drug," Cancer Metastasis Rev, 2009, 28:355-367.
Dring et al., "A Global Expression-based Analysis of the Consequences of the t(4;14) Translocation in Myeloma," Clinical Cancer Research, Sep. 2004, 10: 5692-5701.
Drueke et al., "Phosphate binders in CKD: bad news or good news?," Journal of the American Society of Nephrology, Aug. 2012, 23(8):1277-1280.
Dutt et al., "Drug-sensitive FGFR2 mutations in endometrial carcinoma," PNAS, Jun. 24, 2008, 105(25):8713-8717.
Dutt et al., "Drug-sensitive FGFR2 mutations in endometrial carcinoma," Supporting Information, Jun. 2008, 8 pages.
Edmondson et al., "Aminopiperidine-fused imidazoles as dipeptidyl peptidase-IV inhibitors," Bioorg & Med Chem Lett., 2009, 19(15):4097-4101.
Eissa, "Synthesis and evaluation of some surface active agents from long chain fatty amine," Spanish National Research Council, Jan. 2007, 58(4):379-389.
Elsheikh et al., "FGFR1 amplification in breast carcinomas: a chromogenic in situ hybridisation analysis," Breast Cancer Research, Mar. 2007, 9(2): 1-12.
Erian at al., "2-Aryl-1,1-dicyano-3-phenylsulfonylpropenes in heterocyclic synthesis. A synthetic strategy towards heterocyclic sulfones," Monatshefte fuer Chemie, 1998, 129(10):1049-1056.
Eskens and Verweij, "The clinical toxicity profile of vascular endothelial growth factor (VEGF) and vascular endothelial growth factor receptor (VEGFR) targeting angiogenesis inhibitors; A review," European Journal of Cancer, 2006, 3127-3139.
Eswarakumar and Schlessinger, "Cellular signaling by fibroblast growth factor receptors," Cytokine & Growth Factor Reviews, 2005, 139-149.
Eurasian Office Action in Eurasian Application No. 201590005, dated Oct. 21, 2015, 6 pages.
Eurasian Office Action in Eurasian Application No. 201590005, Mar. 28, 2018, 6 pages.
Eurasian Office Action in Eurasian Application No. 201791866, dated Feb. 19, 2018, 10 pages (English Translation).
Eurasian Office Action in Eurasian Application No. 201791867, dated Apr. 4, 2018, 4 pages (English Translation).
European Communication pursuant to Article 94(3) EPC in European Application No. 13783125.1, dated Jan. 26, 2016, 4 pages.
European Office Action in European Application No. 18733045.1, dated Jan. 11, 2021, 5 pages.
European Office Action in European Application No. 20192679.7, dated Feb. 11, 2021, 7 pages.
European Office Action in European Application No. 16715139.8, dated May 18, 2021, 9 pages.
European search report in European Application No. 16203866.5, dated Mar. 1, 2017, 7 pages.
European Search Report in European Application No. 17199421.3, dated Jul. 12, 2018, 15 pages.
European Search Report in European Application No. 17199421.3, dated Mar. 12, 2018, 14 pages.
Faul et al., "FGF23 induces left ventricular hypertrophy," The Journal of Clinical Investigation, 2010, 1-16.
FDA.Gov, "FDA grants accelerated approval to pemigatinib for cholangiocarcinoma with an FGFR2 rearrangement or fusion," Apr. 20, 2020, [Retrieved on Apr. 27, 2021], retrieved from URL <https://www.fda.gov/drugs/resources-information-approved-drugs/fda-grants-accelerated-approval-pemigatinib-cholangiocarcinoma-fgfr2-rearrangement-or-fusion>, 2 pages.
Feng et al., "Guidance to rational use of pharmaceuticals in gallbladder sarcomatoid carcinoma using patient-derived cancer cells and whole exome sequencing," Oncotarget, 2017, 8(3): 5349-5360.
Feng et al., "Targeting Fibroblast Growth Factor Receptor Signaling Inhibits Prostate Cancer Progression," Clinical Cancer Research, 2012, 1-9.
Ferrera et al., "Bevacizumab (Avastin), a humanized anti-VEGF monoclonal antibody for cancer therapy," Biochemical and Biophysical Research Communications, 2005, 328-335.
Fillmore et al., "Estrogen expands breast cancer stem-like cells through paracrine FGF/Tbx3 signaling," PNAS, 2010, 1-6.
Fischer et al., "Fibroblast growth factor receptor-mediated signals contribute to the malignant phenotype of non-small cell lung cancer cells: therapeutic implications and synergism with epidermal growth factor receptor inhibition," Mol Cancer Therapy, 2008, 3408-3419.
French et al., Targeting FGFR4 inhibits hepatocellular carcinoma in preclinical mouse models, PLoS One 2012;7:e36713.
Fricker, "Metal based drugs: from serendipity to design," Dalton Transactions, 2007, 43:4903-4917.
Fricker, "The therapeutic application of lanthanides," Chemical Society Reviews, 2006, 35(6):524-533.
Frishberg et al., "Hypertosis-Hyperphosphatemia Syndrome: A Congenital Disorder of O-Glycosylation Associated With Augmented Processing of Fibroblast Growth Factor 23," Journal of Bone and Mineral Research, 2007, 22(2): 235-242.
Frishberg et al., "Identification of a recurrent mutation in GALNT3 demonstrates that hyperostosis-hyperphosphatemia syndrome and familial tumoral calcinosis are allelic disorders," J Mol Med, 2005, 83:33-38.
Fu et al., "Intratumoral inorganic phosphate deprivation: A new anticancer strategy," Medical Hypotheses, Febmary 2020, 135:109497.
Fukumoto and Yamashita, "FGF23 is a hormone-regulating phophate metabolism—Unique biological characteristics of FGF23," Bone, 2007, 1190-1195.
Fun et al., "2-7(7,8-Diphenyl-1H-imidazo[4,5-f]-quinoxalin-2-yl)phenol methanol disolvate," Acta Crystallographica Section E Structure Reports Online, 2008, 64(9):o1741-o1742.
Furniss "Acidic/Basic characteristics for purification," Vogel's Textbook of Practical Organic Chemistiy, 5th edition, 1989, 131-133, 135-143.
Galdemard et al., "Regulation of FGF-3 Gene Expression in Tumorigenic and Non-tumorigenic Clones of a Human Colon Carcinoma Cell Line," The Journal of Biological Chemistry, 2000, 275(23): 17364-17373.
Gallo et al., "Functions of Fibroblast Growth Factor Receptors in cancer defined by novel translocations and mutations," Cytokine & Growth Factor Reviews, 2015, 26(4):425-449.
Garringer et al., "Molecular genetic and biochemical analyses of FGF23 mutations in familial tumoral calcinosis," Am J Physiol Endocrinol Metab, 2008, 929-937.

(56) References Cited

OTHER PUBLICATIONS

Gattineni et al., "FGF23 decreases renal NaPi-2a and NaPi-2c expression and induces hypophosphatemia in vivo predominantly via FGF receptor 1," Am J Physiol Renal Physiol, 2009, 297: 282-291.
Gavine et al., "AZD4547: An Orally Bioavailable, Potent, and Selective Inhibitor of the Fibroblast Growth Factor Receptor Tyrosine Kinase Family," American Association for Cancer Research, Apr. 2012, 72(8): 2045-2056.
Gennaro et al., "Pharmaceutical Sciences," Remington's Pharmaceutical Sciences 17th Ed., Jan. 1985, 14-18 and 1409-1423.
Gerby et al., "2-Arylidenedihydroindole-3-ones: Design, synthesis, and biological activity on bladder carcinoma cell lines," Bioorganic & Medicinal Chemistiy Letters, 2007, 208-213.
Ghorab et al., "Synthesis of some sulfur containing Tetrahydrobenzoabuthieno[b] Thieno(Pyridines, Quinolines, Oxazines and Pyrimidines) as possible radioprotective and Antineoplastic agents," Phosphorus, Sulfur and Silicon, Jan. 1998, 134/135:57-76.
Gibson, "Pharmaceutical Preformulation and Formulation," CRC Press LLC, 2009, 2nd ed, 559 pages.
Goetz et al., "Isolated C-terminal tail of FGF23 alleviates hypophosphatemia by inhibiting FGF23-FGFR-Klotho complex formation," PNAS, Januaiy 2010, 107(1): 407-412.
Golub et al., "Molecular Classification of Cancer: Class Discovery and Class Prediction by Gene Expression Monitoring," Science, 1999, 286: 531-537.
Gomez-Rivera et al., "The Tyrosine Kinase Inhibitor, AZD2171, Inhibits Vascular Endothelial Growth Factor Receptor Signaling and Growth of Anaplastic Thyroid Cancer in an Orthotopic Nude Mouse Model," Clin Cancer Res, Aug. 2007, 4519-4527.
Govindan, "Summary of Presentations from the Ninth Annual Targeted Therapies in Lung Cancer Symposium," Journal of Thoracic Oncology, Nov. 2009, 4(11): 1045-1089.
Gozgit et al., "Ponatinib (AP24534), a Multitargeted Pan-FGFR Inhibitor with Activity in Multiple FGFR-Amplified or Mutated Cancer Models," Mol Cancer Ther, 2012, 11: 690-699.
Granberg et al., "Strong FGFR3 staining is a marker for FGFR3 fusions in diffuse gliomas," Neuro-Oncology, 2017, 19(9): 1206-1216.
Grand et al., "Targeting FGFR3 in multiple myeloma: inhibition of t(4;14)-positive cells by SU5402 and PD173074," Leukemia, 2004, 18: 962-966.
Greene, T. W. and Wuts, P. G. M., "Protective Groups in Organic Synthesis", 3rd Ed., Wiley & Sons, Inc., New York (1999), 799 pages.
Greulich and Pollock, "Targeting mutant fibroblast growth factor receptors in cancer," Cell Press, May 2011, 17(5): 283-292.
Grose and Dickson, "Fibroblast growth factor signaling in tumorigenesis," Cytokine & Growth Factor Reviews, 2005, 179-186.
Gu et al., "Phosphotyrosine profiling identifies the KG-1 cell line as a model for the study of FGFR1 fusions in acute myeloid leukemia," Blood, Dec. 15, 2006, 108(13):4202-42040.
Guagnano et al., "Discovery of 3-(2,6-Dichloro-3,5-dimethoxyphenyl)-1-{6-[4-(4-ethyl-piperazin-1-yl)-phenylamino]-pyrimidin-4-yl}-1-methyl-urea (NVP-BGJ398), a Potent and Selective Inhibitor of the Fibroblast Growth Factor Receptor Family of Receptor Tyrosine Kinase," J. Med. Chem., 2011, 54: 7066-7083.
Guan et al., "Design and synthesis of aminopropyl tetrahydroindole-based indolin-2-ones as selective and potent inhibitors of Src and Yes tyrosine kinase," Bioorganic & Medicinal Chemistry Letters, 2004, 187-190.
Gust et al., "Fibroblast Growth Factor Receptor 3 is a Rational Therapeutic Target in Bladder Cancer," Molecular Cancer Therapeutics, Jul. 2013, 12(7): 1245-1254.
Haas et al., "Recent Developments in Negishi Cross-Coupling Reactions," ACS Catal., 2016, 6(3):1540-1552.
Hackam et al. "Translation of Research Evidence From Animals to Humans," JAMA, 296(14), 2006, 296(14):1731-1732.
Hafner et al., "High Frequency of FGFR3 Mutations in Adenoid Seborrheic Keratoses," Journal of Investigative Dermatology, 2006, 126: 2404-2407.
Hafner, "Seborrheic keratoses and epidermal nevi: new pathogenetic insights and therapeutic implications," Expert Rev Dermatol, 2006, 1(6): 759-761.
Hagel et al., "First Selective Small Molecule Inhibitor of FGFR4 for the Treatment of Hepatocellular Carcinomas with an Activated FGFR4 Signaling Pathway," Cancer Discovery, Apr. 2015, 1-14.
Hara and Saito, "CARD9 versus CARMA1 in innate and adaptive immunity," Cell Press, 2009, 234-242.
Heinrich et al., "Fragment-based discovery of new highly substituted 1H-pyrrolo[2,3-b]- and 3H-imidazolo[4,5-b]-pyridines as focal adhesion kinase inhibitors," J of Med Chem., Jan. 8, 2013, 56(3): 1160-1170.
Heinzle C, et al., "Differential Effects of Polymorphic Alleles of FGF Receptor 4 on Colon Cancer Growth and Metastasis," Cancer Research, Nov. 2012, 72(22):5767-5777.
Heinzle et al., "Is fibroblast growth factor receptor 4 a suitable target of cancer therapy?," Cur. Pharm. Des., 2014, 20:2881-2898.
Heinzle et al., "Targeting fibroblast-growth-factor-receptor-dependent signaling for cancer therapy," Expert Opinion, 2011, 1-18.
Helsten et al., "The FGFR Landscape in Cancer: Analysis of 4,853 Tumors by Next-Generation Sequencing," Clin. Cancer Res., Jan. 2016, 22:259-267.
Hideshima and Anderson, "Preclinical Studies of Novel Targeted Therapies," Hematol Oncol Clin N Am, 2007, 1071-1091.
Ho et al., "Fibroblast growth factor receptor 4 regulates proliferation, anti apoptosis and alpha-fetoprotein secretion during hepatocellular carcinoma progression and represents a potential target for therapeutic intervention," J Hepatol, 2009, 50:118-127.
Honigberg et al., "The Bruton tyrosine kinase inhibitor PCI-32765 blocks B-cell activation and is efficacious in models of autoimmune disease and B-cell malignancy," Supporting Information, PNAS, Jul. 20, 2010, 107:29.
Hruska et al., "The Pathogenesis of Vascular Calcification in the Chronic Kidney Disease Mineral Bone Disorder (CKD-MBD): The Links Between Bone and Vasculature," Semin Nephrol, Mar. 2009, 29(2): 156-165.
Hu and Cong, "Fibroblast growth factor 19 is correlated with an unfavorable prognosis and promotes progression by activating fibroblast growth factor receptor 4 in advanced-stage serous ovarian cancer," Oncol Rep., Aug. 20, 2015, 34(5):2683-2691.
Huynh, "Tyrosine kinase inhibitors to treat liver cancer," Expert Opinion, 2010, 13-26.
Hynes and Dey, "Potential for Targeting the Fibroblast Growth Factor Receptors in Breast Cancer," Cancer Res, 2010, 70:5199-5202.
ICH Harmonised Tripartite Guideline, "Specifications:Test Procedures and Acceptance Criteria for New Drug Substances and New Drug Products Chemical Substances," ICHTRRPHU, Oct. 6, 1999, 35 pages.
Ichikawa et al., "A homozygous missense mutation in human KLOTHO causes severe tumoral calcinosis," The Journal of Clinical Investigation, Sep. 2007, 117(9): 2684-2691.
Ichikawa et al., "A Novel GALNT3 Mutation in a Pseudoautosomal Dominant Form of Tumoral Calcinosis: Evidence That the Disorder is Autosomal Recessive," J. Clin. Endocrinol. Metab., 2005, 90:2420-2423.
Ichikawa et al., "Clinical Variability of Familial Tumoral Calcinosis Caused by Novel GALNT3 Mutations," American Journal of Medical Genetics, 2009, 896-903.
Ichikawa et al., "Novel GALNT3 Mutations Causing Hyperostosis-Hyperphosphatemia Syndrome Result in Low Intact Fibroblast Growth Factor 23 Concentrations," J. Clin. Endocrinol. Metab., 2007, 92:1943-1947.
Ichikawa et al., "Tumoral Calcinosis Presenting with Eyelid Calcifications due to Novel Missense Mutations in the Glycosyl Transferase Domain of the GALNT3 Gene," J. Clin. Endocrinol. Metab., 2006, 91: 4472-4475.
Indian Office Action in Indian Application No. 10665/DELNP/2014, dated Jun. 25, 2018, 8 pages.

(56) References Cited

OTHER PUBLICATIONS

Indian Office Action in Indian Application No. 201717030265, dated Dec. 12, 2019, 5 pages.
Indian Office Action in Indian Application No. 201717030267, dated Dec. 3, 2019, 7 pages.
Indian Office Action in Indian Application No. 9781/DELNP/2015, dated Jan. 18, 2019, 6 pages.
Indonesian Office Action in Indonesian Application No. P00201507153, dated Apr. 27, 2018, 5 pages (English Translation).
Indonesian Office Action in Indonesian Application No. PID201705977, dated Jun. 5, 2020, 5 pages.
Inokuchi et al., "Therapeutic targeting of fibroblast growth factor receptors in gastric cancer," Gastroenterol Res Pract., Apr. 27, 2015, 2015:796380, 8 pages.
International Invitation to Pay Fees in International Appln. No. PCT/US2019/030633, dated Aug. 12, 2019, 5 pages.
International Preliminary Report on Patentability and Written Opinion in International Application No. PCT/US2011/066473, dated Jun. 25, 2013, 10 pages.
International Preliminary Report on Patentability in International Application No. PCT/US2013/045309, dated Dec. 24, 2014, 11 pages.
International Preliminary Report on Patentability in International Application No. PCT/US2013/054361, dated Feb. 19, 2015, 7 pages.
International Preliminary Report on Patentability in International Application No. PCT/US2014/034662, dated Oct. 29, 2015, 12 pages.
International Preliminary Report on Patentability in International Application No. PCT/US2015/056583, dated Apr. 25, 2017, 7 pages.
International Preliminary Report on Patentability in International Application No. PCT/US2016/018737, dated Aug. 31, 2017, 8 pages.
International Preliminary Report on Patentability in International Application No. PCT/US2016/018770, dated Aug. 22, 2017, 10 pages.
International Preliminary Report on Patentability in International Application No. PCT/US2016/018787, dated Aug. 22, 2017, 7 pages.
International Preliminary Report on Patentability in International Application No. PCT/US2018/034559, dated Nov. 26, 2019, 8 pages.
International Preliminary Report on Patentability in International Application No. PCT/US2019/030578, dated Nov. 10, 2020, 14 pages.
International Preliminary Report on Patentability in International Application No. PCT/US2019/030633, dated Nov. 10, 2020, 10 pages.
International Search Report and Written Opinion for International Application No. PCT/US2015/056583, dated Dec. 15, 2015, 10 pages.
International Search Report and Written Opinion in International Application No. PCT/US2013/045309, dated Jan. 22, 2014, 19 pages.
International Search Report and Written Opinion in International Application No. PCT/US2013/054361, dated Oct. 16, 2013, 12 pages.
International Search Report and Written Opinion in International Application No. PCT/US2014/034662, dated Oct. 24, 2014, 18 pages.
International Search Report and Written Opinion in International Application No. PCT/US2016/018737, dated Jun. 2, 2016, 12 pages.
International Search Report and Written Opinion in International Application No. PCT/US2016/018770, dated Jun. 2, 2016, 14 pages.
International Search Report and Written Opinion in International Application No. PCT/US2016/018787, dated Jun. 2, 2016, 12 pages.
International Search Report and Written Opinion in International Application No. PCT/US2018/034559, dated Mar. 8, 2019, 14 pages.
International Search Report and Written Opinion in International Application No. PCT/US2019/030578, dated Jul. 11, 2019, 26 pages.
International Search Report and Written Opinion in International Application No. PCT/US2019/030633, dated Nov. 28, 2019, 21 pages.
International Search Report and Written Opinion in International Application No. PCT/US2020/021313, dated Jun. 26, 2020, 19 pages.
International Search Report and Written Opinion in International Application No. PCT/US2020/041104, dated Sep. 4, 2020, 14 pages.
International Search Report and Written Opinion in International Application. No. PCT/US2011/066473, dated Jun. 19, 2012, 15 pages.
International Search Report and Written Opinion in International Appln. No. PCT/US2020/063038, dated Mar. 15, 2021, 16 pages.
International Search Report and Written Opinion in International Appln. No. PCT/US2020/063064, dated Feb. 12, 2021, 13 pages.
International Search Report in International Application No. PCT/US2020/053436, dated Dec. 4, 2020, 15 pages.
International Search Report in Written Opinion in International Application No. PCT/US2020/055547, dated Jan. 11, 2021, 13 pages.
International Search Report in Written Opinion in International Application No. PCT/US2021/013438, dated Apr. 20, 2021, 16 pages.
Invitation to Pay Additional Fees and, Where Applicable, Protest Fee in International Application No. PCT/US2013/045309, dated Nov. 25, 2013, 5 pages.
Isakova et al., "Fibroblast Growth Factor 23 and Risks of Mortality and End-Stage Renal Disease in Patients With Chronic Kidney Disease," JAMA, Jun. 15, 2011, 305:23, 2432-2439.
Ishikawa et al., "Accelerated proliferation of myeloma cells by interleukin-6 cooperating with fibroblast growth factor receptor 3-mediated signals," Oncogene, 2005, 24:6328-6332.
Israeli Office Action in Israeli Application No. 236,078 dated Mar. 21, 2017, 10 pages (English Translation).
Jackson et al., "8p11 Myeloproliferative syndrome: a review," Human Pathology, Apr. 1, 2010, 41:461-476.
Jan de Bern, "Tumoral Calcinosis: A Look into the Metabolic Mirror of Phosphate Homeostasis," The Journal of Clinical Endocrinology & Metabolism, 2005, 90: 2469-2471.
Japanese Office Action in Japanese Application No. 2015-517376, dated Feb. 21, 2017, 5 pages (with English translation).
Japanese Office Action in Japanese Application No. 2016-509131, dated Feb. 20, 2018, 5 pages (English Translation).
Japanese Office Action in Japanese Application No. 2017-543981, dated Dec. 3, 2019, 4 pages.
Japanese Office Action in Japanese Application No. 2017-544021, dated Nov. 26, 2019, 6 pages.
Japanese Office Action in Japanese Application No. 2018-228352, dated Aug. 20, 2019, 6 pages.
Javidi-Sharifi et al., "Crosstalk between KIT and FGFR3 Promotes Gastrointestinal Stromal Tumor Cell Growth and Drug Resistance," Cancer Research, Mar. 2015, 75(5): 880-892.
Jebar et al., "FGFR3 and Ras gene mutations are mutually exclusive genetic events in urothelial cell carcinoma," Oncogene, 2005, 24: 5218-5225.
Jiang et al., "miR-99a promotes proliferation targeting FGFR3 in human epithelial ovarian cancer cells," Biomedicine & Pharmacotherapy, 2014, 68: 163-169.
Ji et al., "Embase abstract: Modeling and simulation as gating for clinical pharmacology studies of INCB054828," 119th Annual Meeting of the American Society for Clinical Pharmacology and Therapeutics, Mar. 1, 2018, 2 pages.
Johnson et al., "Pharmacological and Functional Comparison of the Polo-like Kinase Family: Insight into Inhibitor and Substrate Specificity," Biochemistry, 2007, 46: 9551-9563.

(56) References Cited

OTHER PUBLICATIONS

Jonker et al., "A phase I study to determine the safety, pharmacokinetics and pharmacodynamics of a dual VEGFR and FGFR inhibitor, brivanib, in patients with advanced or metastatic solid tumors," Annals of Oncology, 2010, 1-7.
Jordan, "Tamoxifen: A Most Unlikely Pioneering Medicine," Nature Reviews: Drug Discovery, Mar. 2003, 2:205-213.
Kang et al., FGFR3 Activates RSK2 to Mediate Hematopoietic Transformation through Tyrosine Phosphorylation of RSK2 and Activation of the MEK/ERK Pathway, Cancer Cell, Sep. 2007, 12:201-214.
Kassack et al., "Structure-activity relationships of analogues of NF449 confirm NF449 as the most potent and selective known $P2X_1$ receptor antagonist," European Journal of Medicinal Chemisty, 2004, 345-357.
Katoh and Katoh, "FGF signaling network in the gastrointestinal tract (Review)," International Journal of Oncology, 2006, 29: 163-168.
Keats et al., "Ten years and counting: so what do we know about t(4;14) (p16;q32) multiple myeloma," Leukemia & Lymphoma, Nov. 2006, 47(11): 2289-2300.
Keer et al., "Enrolling a Rare Patient Population: Establishing Proof of Concept for FP-1039, an FGF "Trap," in Endometrial Cancer Patients with the S252W FGFR2 Mutation," Journal of Clinical Oncology, 2010 ASCO Annual Meeting Abstracts, 28:15, May 20 Supplement, 1 page.
Kerekes et. al., "Aurora kinase inhibitors based on the imidazo[1,2-a]pyrazine core: fluorine and deuterium incorporation improve oral absorption and exposure," J Med Chem., 2011, 54(1):201-210.
Khojasteh et al., "Chemical inhibitors of cytochrome P450 isoforms in human liver microsomes: a re-evaluation of P450 isoform selectivity," Eur J Drug Metab Pharmacokinet., Mar. 2011, 36:1-16.
Kim et al., "Phase I/II and Pharmacodynamic Study of Dovitinib (TKI258), an Inhibitor of Fibroblast Growth Factor Receptors and VEGF Receptors, in Patients with Advanced Melanoma," Clin Cancer Res, 2011, 17: 7451-7461.
Kim et al., "The design, synthesis, and biological evaluation of potent receptor tyrosine kinase inhibitors," Bioorganic & Medicinal Chemistry Letters, 2012, 4979-4985.
Klein et al., "FGFR1 Kinase Inhibitors: Close Regioisomers Adopt Divergent Binding Modes and Display Distinct Biophysical Signatures," American Chemical Society, 2014, 166-171.
Knights and Cook, "De-regulated FGF receptors as therapeutic targets in cancer," Pharmacology & Therapeutics, 2010, 125:105-117.
Kompier et al., "Bladder cancer: Novel molecular characteristics, diagnostic, and therapeutic implications," Urologic Oncology: Seminars and Original Investigations, 2010, 91-96.
Kompier et al., "FGFR3, HRAS, KRAS, NRAS and PIK3CA Mutations in Bladder Cancer and Their Potential as Biomarkers for Surveillance and Therapy," PLoS One, Nov. 2010, 5(11): 1-13.
Kono et al., "The fibroblast growth factor receptor signaling pathway as a mediator of intrinsic resistance to EGFR-specific tyrosine kinase inhibitors in non-small cell lung cancer," Drug Resistance Updates, 2009, 95-102.
Korean Office Action in Korean Application No. 10-2015-7000701, dated Aug. 26, 2019, 19 pages.
Korean Office Action in Korean Application No. 10-2015-7032502, dated Sep. 9, 2020, 16 pages.
Korean Office Action in Korean Application No. 10-2020-7021884, dated Oct. 28, 2020, 15 pages.
Kotha et al., "Recent applications of the Suzuki-Miyaura cross-coupling reaction in organic synthesis," Tetrahedron, 2002, 58:9633-9695.
Koziczak and Hynes, "Cooperation between Fibroblast Growth Factor Receptor-4 and ErbB2 in Regulation of Cyclin D1 Translation," The Journal of Biological Chemistry, 2004, 279(48): 50004-50011.
Koziczak et al., "Blocking of FGFR signaling inhibits breast cancer cell proliferation through downregulation of D-type cyclins," Oncogene, 2004, 23:3501-3508.
Krejci et al., "Molecular pathology of the fibroblast growth factor family," Hum Mutat, Sep. 2009, 30(9): 1245-1255.
Krejci et al., "NF449 is a Novel Inhibitor of Fibroblast Growth Factor Receptor 3 (FGFR3) Signaling Active in Chondrocytes and Multiple Myeloma Cells," The Journal of Biological Chemistry, Jul. 2010, 285(27): 20644-20653.
Krejci et al., "NF449 is a novel inhibitor of fibroblast growth factor receptor 3 (FGFR3) signaling active in chondrocytes and multiple myeloma cells," The American Society for Biochemistry and Molecular Biology, 2010, 1-20.
Kunii et al., "FGFR2-Amplified Gastric Cancer Cell Lines Require FGFR2 and Erbb3 Signaling for Growth and Survival," Cancer Res., Apr. 1, 2008, 68(7):2340-2348.
Kunii et al., "FGFR2-Amplified Gastric Cancer Cell Lines Require FGFR2 and Erbb3 Signaling for Growth and Survival," Cancer Res., Apr. 1, 2008, Supplemental figures, 11 pages.
Kuroso et al., "Immunohistochemical Detection of Fibroblast Growth Factor Receptor 3 in Human Breast Cancer: Correlation with Clinicopathological/Molecular Parameteres and Prognosis," Pathobiology, Mar. 2010, 77: 231-240.
Kurosu et al., "Regulation of Fibroblast Growth Factor-23 Signaling by Klotho," The Journal of Biological Chemistiy, Mar. 2006, 281(10): 6120-6123.
Lala et al., "Role of nitric oxide in tumor progression: Lessons from experimental tumors," Cancer and Metastasis Reviews, 1998, 17: 91-106.
Lammoglia and Mericq, "Familial Tumoral Calcinosis Caused by a Novel FGF23 Mutation: Response to Induction of Tubular Renal Acidosis with Acetazolamide and the Non-Calcium Phosphate Binder Sevelamer," Horm Res, 2009, 71:178-184.
Lamont et al., "Small molecule FGF receptor inhibitors block FGFR-dependent urothelial carcinoma growth in vitro and in vivo," Br. J Cancer, 2010, 1-8.
Lamont et al., "Small molecule FGF receptor inhibitors block FGFR-dependent urothelial carcinoma growth in vitro and in vivo," Br. J Cancer, 2011, 104:75-82.
Le Corre et al., "Synthesis and biological evaluation of a triazole-based library of pyrido[2,3-d]pyrimidines as FGFR3 tyrosine kinase inhibitors," Org. Biomol. Chem., 2010, 8, 2164-2173.
Lee et al., "In vivo Target Modulation and Biological Activity of CHIR-258, a Multitargeted Growth Factor Receptor Kinase Inhibitor, in Colon Cancer Models," Clin Cancer Res, May 2005, 3633-3641.
L'Hote and Knowles, "Cell responses to FGFR3 signalling: growth, differentiation and apoptosis," Experimental Cell Research, 2005, 417-431.
Li et al., "Compound deletion of Fgfr3 and Fgfr4 partially rescues the Hyp mouse phenotype," Am. J. Physiology—Endocrinol Metab, Dec. 7, 2010, 300:3, 29 pages.
Liang et al., "Anticancer molecules targeting fibroblast growth factor receptors," Cell Press, 2012, 11 pages.
Liu et al., "Developing Irreversible Inhibitors of the Protein Kinase Cysteinome," Chemistry & Biology, Februaiy 2013, 146-159.
Liu et al., "FRFR3 and FRFR4 Do not Mediate Renal Effects of FGF23," J Am Soc Nephrol, 2008, 19:2342-2350.
Liu et al., "Pathogenic role of Fgf23 in Hyp mice," Am J Physiol Endocrinol Metab 291, Jan. 31, 2006, E38-E49.
Lopes de Menezes et al., "CHIR-258: A Potent Inhibitor of FLT3 Kinase in Experimental Tumor Xenograft Models of Human Acute Myelogenous Leukemia," Clin Cancer Res, Jul. 2005, 5281-5291.
Luo et al., "Deficiency of metabolic regulator FGFR4 delays breast cancer progression through systemic and microenvironmental metabolic alterations," Cancer & Metabolism, 2013, 20 pages.
Maeda et al., "Transforming property of TEL-FGFR3 mediated through PI3-K in a T-cell lymphoma that subsequently progressed to AML," Blood, Mar. 2005, 105(5): 2115-2123.
Malaysian Office Action in Malaysian Application No. 2014003396, dated Dec. 15, 2017, 4 pages.

(56) References Cited

OTHER PUBLICATIONS

Marek et al., "Fibroblast Growth Factor (FGF) and FGF Receptor-Mediated Autocrine Signaling in Non-Small-Cell Lung Cancer Cells," Molecular Pharmacology, 2009, 75:196-207.
Marfe and Stefano, "in vitro Anti-leukaemia Activity of Pyrrolo[1,2-b][1,2,5]benzothiadiaze-pines (PBTDs)," Recent Patents on Anti-Cancer Drug Discoveiy, 2010, 58-68.
Marks et al., "Mutational Analysis of EGFR and Related Signaling Pathway Genes in Lung Adenocarcinomas Identifies a Novel Somatic Kinase Domain Mutation in FGFR4," PLoS One, May 9, 2007, 2:e426.
Marshall et al., "Fibroblast Growth Factor Receptors are Components of Autocrine Signaling Networks in Head and Neck Squamous Cell Carcinoma Cells," Clin Cancer Res., 2011, 17:5016-5025.
Martinez-Torrecuadrada et al., "Targeting the Extracellular Domain of Fibroblast Growth Factor Receptor 3 with Human Single-Chain Fv Antibodies Inhibits Bladder Carcinoma Cell Line Proliferation," Clin Cancer Res, Sep. 2005, 6280-6290.
Martino et al., "Mutant fibroblast growth factor receptor 3 induces intracellular signaling and cellular transformation in a cell type- and mutation-specific manner," Oncogene, 2009, 28: 4306-4316.
Matsuda et al., "Fibroblast Growth Factor Receptor 2 IIIc as a Therapeutic Target for Colorectal Cancer Cells," Mol Cancer Ther., 2012, 52 pages.
McConkey et al., "Molecular genetics of bladder cancer: Emerging mechanisms of tumor initiation and progression," Urologic Oncology: Seminars and Original Investigations, 2010, 429-440.
McMahon, "VEGF Receptor Signaling in Tumor Angiogenesis," Oncologist, 2000, 5(suppl 1):3-10.
Meijer et al., "Fibroblast growth factor receptor 4 predicts failure on tamoxifen therapy in patients with recurrent breast cancer," Endocrine-Related Cancer, 2008, 15:101-111.
Mellor, "Targeted inhibition of the FGF19-FGFR4 pathway in hepatocellular carcinoma; translational safety considerations," Liver International, 2013, 1-9.
Memon et al., "Does Fgf23-klotho activity influence vascular and soft tissue calcification through regulating phosphate homeostasis," Kidney Int., 2008, 74(5): 566-570.
Metzner, "Fibroblast Growth Factor Receptors as Therapeutic Targets in Human Melanoma: Synergism with BRAF Inhibition," J Investigative Dermatol., 2011, 131:2087-2095.
Mexican Office Action in Mexican Application No. MX/a/2014/015192, dated Jan. 24, 2018, 6 pages.
Miyake et al., "1-tert-Butyl-3-[6-(3,5-dimethoxy-phenyl)-2-(4-diethylamino-butylamino)-pyrido[2,3-d]pyrimidin-7-yl]-urea (PD173074), a Selective Tyrosine Kinase Inhibitor of Fibroblast Growth Factor Receptor-3 (FGFR3), Inhibits Cell Proliferation of Bladder Cancer Carrying the FGFR3 Gene Mutation along with Up-Regulation of p27/Kip1 and $G_1/G_0$ Arrest," The Journal of Pharmacology and Experimental Therapeutics, 2010, 332(3):795-802.
Mohammadi et al., "Crystal structure of an angiogenesis inhibitor bound to the FGF receptor tyrosine kinase domain," The EMBO Journal, 1998, 5896-5904.
Mohammadi et al., "Structures of the Tyrosine Kinase Domain of Fibroblast Growth Factor Receptor in Complex with Inhibitors," Science, May 1997, 276:955-960.
Murphy et al., "Evidence for distinct alterations in the FGF axis in prostate cancer progression to an aggressive clinical phenotype," J Pathol., 2010, 220:452-460.
Naito et al., "Progressive tumoral calcinosis as the presenting feature of sarcoidosis in a patient on haemodialysis treatment," Nephrol Dial Transplant, 1999, 14:2716-2719.
Nakatani et al., "In vivo genetic evidence for klotho-dependent, fibroblast growth factor 23 (Fgf23)—mediated regulation of systemic phosphate homeostasis," The FASEB Journal, Feb. 2009, 23:433-441.

Natajaran et al., "p38 MAP kinase inhibitors. Part 3: SAR on 3,4-dihydropyrimido-[4,5-d]pyrimidin-2-ones and 3,4-dihydropyrido[4,3-d]-pyrimidin-2-ones," Bioorgan. Med. Chem. Lett., 2006, 4400-4404.
Neidle et al., "Failure Modes in the Discovery Process," Cancer Drug Design, 2008, pp. 427-431.
New Zealand Examination Report in New Zealand Application No. 743274, dated Jul. 18, 2018, 4 pages.
New Zealand Office Action in New Zealand Application No. 702747, dated Mar. 8, 2019, 2 pages.
New Zealand Office Action in New Zealand Application No. 702747, dated Sep. 16, 2016, 3 pages.
New Zealand Office Action in New Zealand Application No. 713074, dated Feb. 18, 2020, 3 pages.
New Zealand Office Action in New Zealand Application No. 743274, dated Jul. 19, 2018, 5 pages.
New Zealand Office Action in New Zealand Application No. 752422, dated Feb. 18, 2020, 2 pages.
Nitta, "Relationship between Fibroblast Growth Factor-23 and Mineral Metabolism in Chronic Kidney Disease," International Journal of Nephrology, 2010, 1-7.
Nomura et al., "FGF10/FGFR20 signal induces cell migration and invasion in pancreatic cancer," Br. J Cancer, 2008, 99:305-313.
Norman et al., "Protein-Ligand Crystal Structures Can Guide the Design of Selective Inhibitors of the FGFR Tyrosine Kinase," J. Med. Chem., 2012, 55(11):5003-5012.
Novelli, "Fosrenol (TM) reduces damaging high levels of phosphate in end-stage kidney disease patients," EurekAlert!, Nov. 2, 2002 [retrieved on Dec. 1, 2020], retrieved from URL <https://www.eurekalert.org/pub_releases/2002-11/pn-fr110202.php>, 4 pages.
Office Action from the Intellectual Property Office of the Philippines in Application No. 1-2014-502772, dated Mar. 17, 2016, 3 pages.
Ornitz et al., "Receptor Specificity of the Fibroblast Growth Factor Family," The Journal of Biological Chemistiy, 1996, 271(25): 15292-15297.
Pai et al., "Antibody-Mediated Inhibition of Fibroblast Growth Factor 19 Results in Increased Bile Acids Synthesis and Ileal Malabsortion of Bile Acides in Cynomolgus Monkeys," Toxicological Sciences, 2012, 126(2): 446-456.
Pan et al., "MK-2461, a Novel Multitargeted Kinase Inhibitor, Preferentially Inhibits the Activated c-Met Receptor," Cancer Res, Februaiy 2010, 1524-1533.
Pandith et al., "Oncogenic role of fibroblast growth factor receptor 3 in tumorigenesis of urinary bladder cancer," Urologic Oncology: Seminars and Original Investigations, 2010, 1-9.
Pandith et al., "Oncogenic role of fibroblast growth factor receptor 3 in tumorigenesis of urinary bladder cancer," Urologic Oncology: Seminars and Original Investigations, 2013, 31: 398-406.
Pardo et al., "The Fibroblast Growth Factor Receptor Inhibitor PD173074 Blocks Small Cell Lung Cancer Growth In vitro and In vivo," Cancer Res, Nov. 2009, 8645-8651.
Paterson et al., "Preclinical studies of fibroblast growth factor receptor 3 as a therapeutic target in multiple myeloma," British Journal of Haematology, 2004, 124:595-603.
Pemvian Office Action in Peruvian Application No. 1424, dated Mar. 12, 2021, 13 pages.
Pemvian Office Action in Peruvian Application No. 1429, dated Mar. 19, 2021, 12 pages.
Pemvian Office Action in Peruvian Application No. 2433, dated Nov. 27, 2018, 13 pages.
Philippine Office Action in Philippine Application No. 1/2017/501483, dated Dec. 12, 2019, 5 pages.
Philippine Office Action in Philippine Application No. 1-2017-501481, dated Oct. 29, 2019, 4 pages.
Philippine Office Action in Philippine Application No. 1/2015/502383, dated Jul. 8, 2019, 7 pages.
Philippine Office Action in the Philippine Application No. 1/2017/501483, dated Aug. 31, 2020, 4 pages.
Piazza et al., "Towards a new age in the treatment of multiple myeloma," Ann Hematol, 2007, 86:159-172.
Pinedo and Slamon, "Translational Research: The Role of VEGF in Tumor Angiogenesis," Oncologist, 2000, 5(suppl 1):1-2.

(56) References Cited

OTHER PUBLICATIONS

Piro et al., "An FGFR3 Autocrine Loop Sustains Acquired Resistance to Trastuzumab in Gastric Cancer Patients," Clinical Cancer Research, Dec. 2016, 22(24): 6164-6175.
Platt et al., "Spectrum of Phosphatidylinositol 3-Kinase Pathway Gene Alterations in Bladder Cancer," Clin Cancer Res, Oct. 2009, 6008-6017.
Pliarchopoulou et al., "Current chemotherapeutic options for the treatment of advanced bladder cancer: A review," Urologic Oncology: Seminars and Original Investigations, 2010, 1-9.
Plowright et al., "Ectopic expression of fibroblast growth factor receptor 3 promotes myeloma cell proliferation and prevents apoptosis," Blood, Feb. 2000, 95(3): 992-998.
Podar et al., "Emerging therapies for multiple myeloma," Expert Opin. Emerging Drugs, 2009, 14(1):9-127.
Podar et al., "Targeting signalling pathways for the treatment of multiple myeloma," Expert Opin. Ther. Targets, 2005, 359-381.
Pollett et al., "Overexpression of the myeloma-associated oncogene fibroblast growth factor receptor 3 confers dexamethasone resistance," Blood, Nov. 2002, 100(10): 3819-3821.
Pollock et al., "Frequent activating FGFR2 mutations in endometrial carcinomas parallel germline mutations associated with craniosynostosis and skeletal dysplasia syndromes," Oncogene, 2007, 26:7158-7162.
Propper et al., "Phase I and Pharmacokinetic Study of PKC412, an Inhibitor of Protein Kinase C," J Clin Oncol, 2001, 19(5):1485-1492.
Qian et al., "Targeting Tumor Angiogenesis with Histone Deacetylase Inhibitors: the Hydroxamic Acid Derivative LBH589," Clin Cancer Res, Jan. 2006, 634-642.
Qing et al., "Antibody-based targeting of FGFR3 in bladder carcinoma and t(4;14)-positive multiple myeloma in mice," The Journal of Clinical Investigation, May 2009, 119(5): 1216-1229.
Qing et al., "Antibody-based targeting of FGFR3 in bladder carcinoma and t(4;14)-positive multiple myeloma in mice," The Journal of Clinical Investigation, May 2009, Supplemental Table 1: Summary of crystallographic analysis, 21 pages.
Qiu et al., "Over-expression of fibroblast growth factor receptor 3 in human hepatocellular carcinoma," World J Gastroenterol, 2005, 11(34): 5266-5272.
Raab et al., "Multiple myeloma," Lancet, 2009, 374: 324-339.
Ravindranathan et al., "Discovery of Novel Fibroblast Growth Factor Receptor 1 Kinase Inhibitors by Structure-Based Virtual Screening," J. Med. Chem., 2010, 53: 1662-1672.
Razzaque, "FGF23-mediated regulation of systemic phosphate homeostasis: is Klotho an essential player?," Am J Physiol Renal Physiol, 2009, 470-476.
Reimers et al., "NoBP, a Nuclear Fibroblast Growth Factor 3 Binding Protein, is Cell Cycle Regulated and Promotes Cell Growth," Molecular and Cellular Biology, Aug. 2001, 21(15): 4996-5007.
Reis-Filho et al., "FGFR1 Emerges as a Potential Therapeutic Target for Lobular Breast Carcinomas," Clin Cancer Res, Nov. 2006, 6652-6662.
Reiter et al., "Consistent Fusion of ZNF198 to the Fibroblast Growth Factor Receptor-1 in the t(8;13)(p11;q 12) Myeloproliferative Syndrome," Blood, Sep. 1998, 92(5): 1735-1742.
Remington's Pharmaceutical Sciences, 17th ed., Mack Publishing Company, Easton, Pa., 1985, p. 1418*.
Renhowe et al., "Design, Structure—Activity Relationships and in Vivo Characterization of 4-Amino-3-benzimidazol-2-ylhydroquinolin-2-ones: A Novel Class of Receptor Tyrosine Kinase Inhibitors," J. Med. Chem., 2009, 52: 278-292.
Ribatti et al., "The discovery of basic fibroblast growth factor/ Iibroblast growth factor-2 and its role in haematological malignancies," Cytokine & Growth Factor Reviews, 2007, 18: 327-334.
Ribatti, "Tyrosine Kinase Inhibitors as Antiangiogenic Dmgs in Multiple Myeloma," Pharmaceuticals, 2010, 3: 1225-1231.
Roidl et al., "Resistance to Chemotherapy is Associated with Fibroblast Growth Factor Receptor 4 Up-Regulation," Clin Cancer Res, Mar. 2009, 2058-2066.
Ronchetti et al., "Deregulated FGFR3 mutants in multiple myeloma cell lines with t(4;14): comparative analysis of Y373C, K650E and the novel G384D mutations," Oncogene, 2001, 20: 3553-3562.
Roumiantsev et al., "Distinct stem cell myeloproliferative/T lymphoma syndromes induced by ZNF198-FGFR1 and BCR-FGFR1 fusion genes from 8p11 translocations," Cancer Cell, Mar. 2004, 5: 287-298.
Ryan et al., "Toxicologic Pathology of Unique Biotechnology Agents and Biotherapies," Toxicologic Pathology, 1999, 27(1): 78-86.
Sakurai et al., "A novel angiogenesis inhibitor, Ki23057, is useful for preventing the progression of colon cancer and the spreading of cancer cells to the liver," European Journal of Cancer, 2007, 2612-2620.
Sarker et al., "A Phase I Pharmacokinetic and Pharmacodynamic Study of TKI258, an Oral, Multitargeted Receptor Tyrosine Kinase Inhibitor in Patients with Advanced Solid Tumors," Clin Cancer Res, Apr. 2008, 2075-2081.
Saxty et al., "Fragment-based drug discovery of selective inhibitors of fibroblast growth factor receptor (FGFr)," Cancer Res, Apr. 15, 2010, 70, 5778.
Schenone et al., "Small Molecules ATP-Comptetitive Inhibitors of FLT3: A Chemical Overview," Current Medicinal Chemistry, 2008, 15(29): 3113-3132.
Schlapbach et al., "A novel Pd-catalyzed cyclization rection of ureas for the synthesis of dihydroquinazolinone p38 kinase inhibitors," Bioorg. Med. Chem. Lett., 2004, 357-360.
Science IP Order 3032627, Chemical Structure Search, Science IP, Apr. 2012, 78 pages.
Science IP Order 3101926, Chemical Structure Search, Science IP, Jan. 2015, 50 pages.
Science IP Order 3101983, Chemical Structure Search, Science IP, Jan. 2015, 70 pages.
Science IP Order 3104564, Patent Chemical Structure Search, Science IP, Mar. 2015, 90 pages.
Science IP Order 3104565, Patent Chemical Structure Search, Science IP, Mar. 2015, 521 pages.
Segev et al., "Restrained chondrocyte proliferation and maturation with abnormal growth plate vascularization and ossification in human FRFR-3$^{G380R}$ transgenic mice," Human Molecular Genetics, 2000, 9(2): 249-258.
Seitzer et al., "A single nucleotide change in the mouse genome accelerates breast cancer progression," Cancer Res., Jan. 2010, 70(2):802-812.
Shariat et al., "Association of Angiogenesis Related Markers With Bladder Cancer Outcomes and Other Molecular Markers," The Journal of Urology, May 2010, 183: 1744-1750.
Sharkey et al., "PKC412 demonstrates JNK-dependent activity against human multiple myeloma cells," Blood, Feb. 2007, 109(4): 1712-1719.
Shi et al., "High Expression of FGFR4 Enhances Tumor Growth and Metastasis in Nasopharyngeal Carcinoma," Journal of Cancer, 2015, 6(12): 1245-1254.
Shinya et al., "Fgf signalling through MAPK cascade is required for development of the subpallial telencephalon in zebrafish embryos," Development, 2001, 4153-4164.
sigmaaldrich.com, "4-Chloro-1H-pyrrolo[2,3-b]pyridine-5-carbaldehyde," CAS # 958230-19-8, [retrieved on Feb. 4, 2021] retrieved from URL <https://www.sigmaaldrich.com/catalog/product/aldrich/ade000976?lang=en&region=US>, 2 pages.
Singh et al., "Transforming Fusions of FGFR and TACC Genes in Human Glioblastoma," Science, Sep. 2012, 337:1231-1235.
Slavin et al., "Familial Tumoral Calcinosis," The American Journal of Surgican Pathology, 1993, 17(8): 188-802.
Smith et al., "Circulating αKlotho influences phosphate handling by controlling FGF23 production," The Journal of Clinical Investigation, Dec. 2012, 122(12): 4710-4715.
Song et al., "Fibroblast growth factors: An epigenetic mechanism of broad spectrum resistance to anticancer drugs," PNAS, Jul. 2000, 97(15): 8658-8663.
Sonvilla et al., "Fibroblast growth factor receptor 3-111c mediates colorectal cancer growth and migration," British Journal of Cancer, 2010, 1-12.

(56) References Cited

OTHER PUBLICATIONS

Soria, "FGFR inhibition overview of clinical development programs," Presentation, presented at TAT in Washington DC on Mar. 5-7, 2014, 54 pages.
Soverini et al., "Novel mutation and RNA splice variant of fibroblast growth factor receptor 3 in multiple myeloma patients at diagnosis," Haematologica, 2002, 87: 1036-1040.
Specktor et al., "Hyperphosphatemic familial tumoral calcinosis caused by a mutation in GALNT3 in a European kindred," J Hum Genet, 2006, 51:487-490.
Squires et al., "Development of inhibitors of the fibroblast growth factor receptor (FGFR) kinase using a fragment based approach," Cancer Res 70, Apr. 15, 2010, 3626.
Squires et al., "Development of inhibitors of the fibroblast growth factor receptor (FGFR) kinase using a fragment based approach," Cancer Res, 2008, 1 page.
STN International Search Report for CAS RN 2380276-25-3, dated Nov. 20, 2019, 11 pages.
STN Search Report dated Jan. 6, 2020, 88 pages.
STN Search Report, dated Sep. 11, 2019, 31 pages.
Sun et al., "Design, Synthesis, and Evaluations of Substituted 3-[(3- or 4-Carboxyethylpyrrol-2-yl)methylidenyl]indolin-2-ones as Inhibitors of VEGF, FGF, and PDGF Receptor Tyrosine Kinases," J. Med. Chem., 1999, 42: 5120-5130.
Sun et al., "Identification of Substituted 3-[(4,5,6,7-Tetrahydro-1H-indol-2-yl)methylene]-1,3-dihydroindol-2-ones as Growth Factor Receptor Inhibitors for VEGF-R2 (Flk-1/KDR), FGF-R1, and PDGF-Rβ Tyrosine Kinases," J. Med. Chem., 2000, 43: 2655-2663.
Sun et al., "Synthesis and Biological Evaluations of 3-Substituted Indolin-2-ones: A Novel Class of Tyrosine Kinase Inhibitors That Exhibit Selectivity toward Particular Receptor Tyrosine Kinases," J. Med. Chem., 1998, 41: 2588-2603.
Surry et al., "Dialkylbiaryl Phosphines in Pd-Catalyzed Amination: A User's Guide," Chem Sci., 2011, 2(1):27-50.
Taiwan Office Action in Taiwan Application No. 103114284, dated Apr. 9, 2018, 4 pages (English Search Report).
Taiwan Office Action in Taiwan Application No. 105104993, dated Feb. 11, 2020, 9 pages.
Taiwan Office Action in Taiwan Application No. 105105018, dated Oct. 22, 2019, 7 pages.
Taiwan Office Action in Taiwan Application No. 107146498, dated Dec. 19, 2019, 7 pages.
Taiwanese Office Action in Taiwan Application No. 102120946, dated Nov. 9, 2016, 9 pages (with English translation).
Taiwanese Office Action in Taiwanese Application No. 102120946, dated Jul. 13, 2017, 7 pages (English Translation).
Takeda et al., "AZD2171 Shows Potent Antitumor Activity Against Gastric Cancer Over-Expressing Fibroblast Growth Factor Receptor 2/Keratinocyte Growth Factor Receptor," Clin Cancer Res, May 2007, 3051-3057.
Takii et al., "Serotonin Derivative, N-(p-Coumaroyl)serotonin, Isolated from Safflower (*Carthamus tinctorius* L.) Oil Cake Augments the Proliferation of Normal Human and Mouse Fibroblasts in Synergy with Basic Fibroblast Growth Factor (bFGF) or Epidermal Growth Factor (EGF)", J Biochem., 1995, 125(5):910-915.
Tan et al., "Development of covalent inhibitors that can overcome resistance to first-generation FGFR kinase inhibitors," PNAS, Oct. 2014, E4869-E4877.
Tang et al., "Role of fibroblast growth factor receptor 4 in cancer," Cancer Science, Oct. 2018, 109(10):3024-3031.
Taylor et al., "Identification of FGFR4-activating mutations in human rhabdomyasarcomas that promote metastasis in xenotransplanted models," J Clin Invest., Nov. 2009, 119(11):3395-3407.
Taylor, "Inhibitor PD-173074 Bound to the Tyrosine Kinase Domain of FGFR 1," Molecular & Behavioral Neuroscience Institute, Feb. 2006, 1 page.
Taylor, "Inhibitor SU-5402 Bound to the Tyrosine Kinase Domain of FGFR 1," Molecular & Behavioral Neuroscience Institute, Apr. 2006, 1 page.

Terai et al., "Vascular calcification and secondary hyperparathyroidism of severe chronic kidney disease and its relation to serum phosphate and calcium levels," British Journal of Pharmacology, 2009, 156: 1267-1278.
Thai Office Action in Thai Application No. 1401007417, dated Jun. 5, 2016, 7 pages (with English translation).
The Cancer Genome Atlas Research Network, "Comprehensive molecular characterization of urothelial bladder carcinoma," Nature, 2014, 507: 315-22.
Thome and Weil, "Post-translational modifications regulate distinct functions of CARMA1 and BCL10," Trends in Immunology, 2007, 28(6): 281-288.
Thompson et al., "3-(3,5-Dimethoxyphenyl)-1,6-naphthyridine-2,7-diamines and Related 2-Urea Derivatives Are Potent and Selective Inhibitors of the FGF Receptor-1 Tyrosine Kinase," J. Med. Chem., 2000, 43: 4200-4211.
Thompson et al., "Photochemical Preparation of a Pyridone Containing Tetracycle: A Jak Protein Kinase Inhibitor," Bioorganic & Medicinal Chemistiy Letters 12:1219-1223, 2002.
Thompson et al., "Synthesis and Structure—Activity Relationships of Soluble 7-Substituted 3-(3,5-Dimethoxyphenyl)-1,6-naphthyridin-2-amines and Related Ureas as Dual Inhibitors of the Fibroblast Growth Factor Receptor-1 and Vascular Endothelial Growth Factor Receptor-2 Tyrosine Kinases," J. Med. Chem., 2005, 48: 4628-2653.
Thussbas et al., "FGFR4 Arg388 Allele is Associated With Resistance to Adjuvant Therapy in Primary Breast Cancer," J. Clin. Oncol., Aug. 10, 2006, 23:3747-3755.
Tolcher et al., "381 Preliminary results of a dose escalation study of the Fibroblast Growth Factor (FGF) "trap" FP-1039 (FGFR1:Fc) in patients with advanced malignancies," EJC Supplements, Nov. 2010, 8:7, p. 121.
Tomlinson et al., "FGFR3 protein expression and its relationship to mutation status and prognostic variables in bladder cancer," J Pathol, Sep. 2007, 213(1): 91-98.
Tomlinson et al., "Fibroblast Growth Factor Receptor 1 Promotes Proliferation and Survival via Activation of the Mitogen-Activated Protein Kinase Pathway in Bladder Cancer," Cancer Res, 2009, 4613-4620.
Tomlinson et al., "Knockdown by shRNA identifies S249C mutant FGFR3 as a potential therapeutic target in bladder cancer," Oncogene, 2007, 26: 5889-5899.
Topaz et al., "Mutations in GALNT3, encoding a protein involved in O-linked glycosylation, cause familial tumoral calcinosis," Nature Genetics, 2004, 1-3.
Traxler and Furet, "Strategies toward the Design of Novel and Selective Protein Tyrosine Kinase Inhibitors," Pharmacol. Ther., 1999, 82(2-3): 195-206.
Trudel et al., "CHIR-258, a novel, multitargeted tyrosine kinase inhibitor for the potential treatment of t(4;14) multiple myeloma," Blood, Apr. 2005, 105(7): 2941-2948.
Trudel et al., "Inhibition of fibroblast growth factor receptor 3 induces differentiation and apoptosis in t(4;14) myeloma," Blood, May 2004, 103(9):3521-3528.
Trudel et al., "The inhibitory anti-FGFR3 antibody, PRO-001, is cytotoxic to t(4;14) multiple myeloma cells," Blood, May 2006, 107(10): 4039-4046.
Trudel, "CHIR-258, a Novel Multi-targeted Tyrosine KinaseInhibitor, for the Treatment of t(4;14) Multiple Myeloma," Presentation, Presented at International Myeloma Foundation, Apr. 2005, 18 pages.
Turkington et al., "Fibroblast growth factor receptor 4 (FGFR4): a targetable regulator of drug resistance in colorectal cancer," Cell Death Dis., Feb. 6, 2014, 5:e1046.
Turner and Grose, "Fibroblast growth factor signalling: from development to cancer," Nature Reviews Cancer, 2010, 10:116-129.
Turner et al., "FGFR1 Amplification Drives Endocrine Therapy Resistance and is a Therapeutic Target in Breast Cancer," Cancer Res., Mar. 2010, 2085-2094.
Tvorogov et al., "Effective Suppression of Vascular Network Formation by Combination of Antibodies Blocking VEGFR Ligand Binding and Receptor Dimerization," Cancer Cell, Dec. 2010, 18: 630-640.

(56) References Cited

OTHER PUBLICATIONS

Ueno et al., "Enhanced Expression of Fibroblast Growth Factor Receptor 3 IIIc Promotes Human Esophageal Carcinoma Cell Proliferation," Journal of Histochemistry & Cytochemistry, 2016, 64(1): 7-17.
Ukraine Office Action in Ukraine Application No. a201500191, dated Dec. 13, 2016, 10 pages (with English translation).
Ukraine Office Action in Ukraine Application No. a201511370, dated Nov. 12, 2018, 6 pages (with English translation).
Ukraine Office Action in Ukraine Application No. a201709220, dated Dec. 9, 2019, 11 pages.
Urakawa et al., "Klotho converts canonical FGF receptor into a specific receptor for FGF23," Nature, Dec. 2006, 444: 770-774.
Uzawa et al., "Targeting fibroblast growth factor receptor 3 enhances radiosensitivity in human squamous cancer cells," Oncogene, 2011, 1-6.
Van Oers et al., "FGFR3 Mutations Indicate Better Survival in Invasive Upper Urinary Tract and Bladder Tumours," European Urology, 2009, 650-658.
Vätsveen et al., "FGFR3 is expressed and is important for survival in INA-6, a human myeloma cell line without a t(4;14)," Eur. J. Haematol., 83:5, Jul. 6, 2009, 471-476.
Verstovsek et al., "Interim Results from Fight-203, a Phase 2, Open-Label, Multicenter Study Evaluating the Efficacy and Safety of Pemigatinib (INCB054828) in Patients with Myeloid/Lymphoid Neoplasms with Rearrangement of Fibroblast Growth Factor Receptor 1 (FGFR1)," Blood, Nov. 29, 2018, retrieved from URL <https://ashpublications.org/blood/article/132/Supplement%201/690/266605/Interim-Results-from-Fight203-a-Phase-2-0penLabel>, 132(Supplement 1):690.
Vietnamese Office Action in Vietnamese Application No. 1-2015-00102, dated Mar. 18, 2015, 4 pages.
Vogt et al., "FGF23 and phosphate cardiovascular toxins in ckd," Toxins, Nov. 6, 2019, 11(11):647.
Von Massenhausen et al., "Evaluation of FGFR3 as a Therapeutic Target in Head and Neck Squamous Cell Carcinoma," Targ. Oncol., 2016, 11: 631-642.
Walsky and Obach, "Validated assays for human cytochrome P450 activities," Drug Metab Dispos., 2004, 32(6):647-660.
Walsky et al., "Evaluation of 227 drugs for in vitro inhibition of cytochrome P450 2B6," J Clin Pharmacol., Dec. 2006, 46(12):1426-1438.
Wang and Becker, "Antisense targeting of basic fibroblast growth factor and fibroblast growth factor receptor-1 in human melanomas blocks intratumoral angiogenesis and tumor growth," Nature Medicine, Aug. 1997, 887-893.
Wang and Ding, "Fibroblast growth factor receptors in breast cancer," Tumor Biology, May 2017, 1-10.
Wang et al., "The fibroblast growth factor receptor-4 Arg388 allele is associated with prostate cancer initiation and progression," Clin Cancer Res. 2004, 10:6169-6178.
Ware et al., "Rapidly Acquired Resistance to EFGR Tyrosine Kinase Inhibitors in NSCLC Cell Lines through De-Repression of FGFR2 andFGFR3 Expression," PLoS, Nov. 2010, 5(11): 1-9.
Weiss et al., Frequent and Focal FGFR1 Amplification Associates with Therapeutically Tractable FGFR1 Dependency in Squamous Cell Lung Cancer, Sci. Transl. Med., 2010, 2(62):62ra93, pp. 1-7.
Williams et al., "Oncogenic FGFR3 gene fusions in bladder cancer," Hum Mol Genet, 2013, 22:795-803.
Wu, "Urothelial Tumorigenesis: A Tale of Divergent Pathways," Nature Reviews, Sep. 2005, 5: 713-725.
Wuts et al., "Greene's Protective Groups in Organic Synthesis," 4th Ed., 2006, Chapter 7, 696-926.
Wöhrle et al., "FGF Receptors Control Vitamin D and Phosphate Homeostasis by Mediating Renal FGF-23 Signaling and Regulating FGF-23 Expression in Bone," Journal of Bone and Mineral Research, Oct. 2011, 26(10): 2486-2497.
Wöhrle et al., "Pharmacological inhibition of FGFR signaling ameliorates FGF23-mediated hypophosphatemic rickets," Journal of Bone and Mineral Research, 2012, 1-36.
Xian et al., "Pleiotropic effects of FGFR1 on cell proliferation, survival, and migration in a 3D mammary epithelial cell model," JCB, 2005, 171(4): 663-673.
Xin et al., "CHIR-258 is Efficacious in A Newly Developed Fibroblast Growth Factor Receptor 3-Expressing Orthotopic Multiple Myeloma Model in Mice," Clin Cancer Res, Aug. 2006, 4908-4915.
Xu et al., "Fibroblast growth factor receptor 4 promotes progression and correlates to poor prognosis in cholangiocarcinoma," Biochemical and Biophysical Research Communications, 2014, 446: 54-60.
Xu et. al. "Design, synthesis and biological evaluation of deuterated nintedanib for improving pharmacokinetic properties," J Label Compd Radiopharm., 2015, 58(7):308-312.
Ying et al., "Genome-wide screening for genetic alterations in esophageal cancer by aCGH identifies 11q13 amplification oncogenes associated with nodal metastasis," PLoS One, Jun. 25, 2012, 7:e39797.
Yu et al., "Analysis of the Biochemical Mechanisms for the Endocrine Actions of Fibroblast Growth Factor-23," Endocrinology, Nov. 2005, 146(11): 4647-4656.
Yu et al., "FGFR-4 Arg(3)(8)(8) enhances prostate cancer progression via extracellular signal-related kinase and serum response factor signaling," Clin Cancer Res., Jul. 2011, 17:4355-4366.
Zaid et al., "Identification of FGFR4 as a Potential Therapeutic Target for Advanced-Stage, High-Grade Serous Ovarian Cancer," Clin Cancer Res, 2013, 19(4): 809-820.
Zhang et al., "AZD4547, a potent and selective FGF-receptor inhibitor induces tumor regressions in a human primary model of FGF-receptor 2 amplified gastric cancer and is efficacious in combination with chemotherapy," 2012, AstraZeneca, 1 page.
Zhang et al., "Direct Cell Cycle Regulation by the Fibroblast Growth Factor Receptor (FGFR) Kinase through Phosphorylation-dependent Release of Cks1 from FGFR Substrate 2," The Journal of Biological Chemistiy, 2004, 279(53): 55348-55354.
Zhang et al., "Enhanced FGFR signalling predisposes pancreatic cancer to the effect of a potent FGFR inhibitor in preclinical models," British Journal of Cancer, 2014, 110: 320-329.
Zhang et al., "FP-1039 (FGFR1:Fc), A Soluble FGFR1 Receptor Antagonist, Inhibits Tumor Growth and Angiogenesis," Mol Cancer Ther, 6, Nov. 2007, B55.
Zhang et al., "Predicting Drug-Drug Interactions: An FDA Perspective," The AAPS Journal, May 6, 2009, 11(2):300-306.
Zhang et al., "Recent progress in therapeutic and diagnostic applications of lanthanides," Mini-Reviews in Medicinal Chemistiy, 2011, 11(8):678-694.
Zhang et al., "Receptor Specificity of the Fibroblast Growth Factor Family," Journal of Biological Chemistiy, Jun. 2006, 281(23): 15694-15700.
Zhang et al., "Translating the therapeutic potential of AZD4547 in FGFR1-amplified non-small cell lung cancer through the use of patient derived tumor xenograft (PDTX) models," Clin cancer Res, Oct. 18, 2012, 40 pages.
Zhao et al., "A Novel, Selective Inhibitor of Fibroblast Growth Factor Receptors That Shows a Potent Broad Spectrum of Antitumor Activity in Several Tumor Xenograft Models," Mol Cancer Ther, Nov. 2011, 2200-2210.
Zhao et al., "Homozygous Deletions and Chromosome Amplifications in Human Lung Carcinomas Revealed by Single Nucleotide Polymorphism Array Analysis," Cancer Res, Jul. 2005, 5561-5570.
Zhou et al., "A Structure-Guided Approach to Creating Covalent FGFR Inhibitors," Chemistry and Biology, Mar. 2010, 285-295.
Zhu et al., "Fibroblast growth factor receptor 3 inhibition by short hairpin RNAs leads to apoptosis in multiple myeloma," Mol Cancer Ther, May 2005, 787-798.
Zieger et al., "Role of Activating Fibroblast Growth Factor Receptor 3 Mutations in the Development of Bladder Tumors," Clin Cancer Res, Nov. 2005, 7709-7719.
Zingone et al., "Ectopic expression of wild-type FGFR3 cooperates with MYC to accelerate development of B-cell lineage neoplasms," Leukemia, 2010, 1171-1178.
Argentina Office Action in Argentina Application No. 20180101392, dated Mar. 8, 2022, 6 pages.
Ash and Ash, "Handbook of Pharmaceutical Additives," Gower Publishing Company, 2007, 3rd ed, Title page only.

(56) References Cited

OTHER PUBLICATIONS

Australian Office Action in Australian Application No. 2020270520, dated Dec. 16, 2021, 4 pages.
Balek, L., "ARQ 087 inhibits FGFR signaling and rescues aberrant cell proliferation and differentiation in experimental models of craniosynostoses and chondrodysplasias caused by activating mutations in FGFR1, FGFR2 and FGFR3," Bone, Dec. 2017, 105:57-66.
Bauer, "Pharmaceutical Solids—The Amorphous Phase", Journal of Validation Technology, 2009, 15(3):63-68.
Canada Office Action in Canada Application No. 2,976,788, dated Apr. 7, 2022, 4 pages.
Chilean Office Action in Chilean Application No. 3439-2019, dated Jan. 31, 2022, 15 pages.
Chilean Office Action in Chilean Application No. 2848-2020, dated Apr. 3, 2022, 24 pages.
Chilean Office Action in Chilean Application No. 2839-2020, dated Jan. 31, 2022, 42 pages (with English translation).
Chinese Office Action in Chinese Application No. 201910023729.3, dated Mar. 23, 2022, 11 pages.
Ecuador Office Action in Ecuador Application No. IFPI-2015-1225, dated Dec. 30, 2021, 21 pages.
Eurasian Office Action in Eurasian Application No. 202092648, dated Feb. 8, 2022, 7 pages.
Indian Oral Hearing in Indian Application No. 201717030265, dated Jan. 13, 2022, 2 pages.
International Preliminary Report on Patentability in International Application No. PCT/US2020/041104, dated Jan. 11, 2022, 7 pages.
International Preliminary Report on Patentability in International Application No. PCT/US2020/053436, dated Apr. 5, 2022, 8 pages.
Japanese Office Action in Japanese Application No. 2020-093529, dated Mar. 1, 2022, 5 pages.
Korean Office Action in Korean Application No. 10-2020-7021884, dated Oct. 25, 2021, 6 pages.
Mexican Office Action in Mexican Application No. MX/a/2019/014097, dated Mar. 15, 2022, 12 pages.
Philippine Office Action in Philippine Application No. Jan. 2019/502810, dated Dec. 7, 2021, 4 pages.
Rowe et al., "Handbook of Pharmaceutical Excipients," The Pharmaceutical Press and the American Pharmaceutical Association, 2009, 6th Edition, 917 pages.
Ukraine Office Action in Ukraine Application No. a 2019 12195, dated Nov. 11, 2021, 7 pages.
Yu et al., "Amorphous pharmaceutical solids: preparation, characterization and stabilization," Advanced Drug Delivery Reviews, May 16, 2001, 48(1):27-42.
Adib et al., "FGFR2/3 genomic alterations and response to Enfortumab Vedotin in metastatic urothelial carcinoma," BJUI Compass., 2022, 3:169-172.
Alexander et al., "Systemtherapie des Harnblasenkarzinoms," Der Urologe, Jan. 4, 2021, 60(2):247-258 (English Abstract).
Australian Allowance in Australian Application No. 2020250201, dated Jun. 23, 2022, 4 pages.
Byrn et al., "Pharmacautical Solids: A Strategic Approach to Regulatory Considerations," Pharmaceutical Research,, Jul. 1995, 12(7):945-954.
Canada Office Action in Canada Application No. 2,976,790, dated Apr. 25, 2022, 4 pages.
Colombian Office Action in Colombian Application No. NC2019/0014699, dated Jun. 6, 2022, 31 pages.
Costa Rican Office Action in Costa Rican Application No. 2019-573, dated Jul. 12, 2022, 12 pages.
De Luca et al., "FGFR Fusions in Cancer: From Diagnostic Approaches to Therapeutic Intervention," Int J Mol Sci., 2020, 21(8):6856.
Ecuador Office Action in Ecuador Application No. IEPI-2015-1225, dated May 11, 2022, 18 pages.
Ecuador Opposition in Ecuador Application No. SENADI-2020-78226, dated Jun. 2022, 19 pages.
Ecuador Opposition in Ecuador Application No. SENADI-2020-78230, dated Jun. 2022, 21 pages.
Eurasian Office Action in Eurasian Application No. 202091923, dated Apr. 5, 2022, 4 pages.
Eurasian Office Action in Eurasian Application No. 202092649/26, dated Apr. 22, 2022, 6 pages.
European Office Action in European Application No. 19724670, dated Aug. 31, 2022, 3 pages.
Hess et al., "Abstract P245: Synergistic effect of combination of pemigatinib with enfortumab vedotin (EV) in human bladder cancer models," Molecular Cancer Therapeutics, Oct. 1, 2021, 20(12 Supplement) :P245.
Hess et al., "Synergistic effect of combination of pemigatinib with enfortumab vedotin (EV) in human bladder cancer models," Molecular Cancer Therapeutics, Presented at AACR-NCI-EORT Virtual International Conference on Molecular Targets and Cancer Therapeutics, presented Oct. 7-10, 2021, 9 pages.
Indian Office Action in Indian Application No. 202017052609, dated May 23, 2022, 7 pages.
Indian Office Action in Indian Application No. 202017052853, dated May 13, 2022, 6 pages.
International Preliminary Report on Patentability in International Application No. PCT/US2020/055547, dated Apr. 19, 2022, 7 pages.
International Preliminary Report on Patentability in International Application No. PCT/US2020/055735, dated Apr. 19, 2022, 8 pages.
International Preliminary Report on Patentability in International Application No. PCT/US2020/063038, dated Jun. 16, 2022, 8 pages.
International Preliminary Report on Patentability in International Application No. PCT/US2020/063064, dated May 17, 2022, 7 pages.
International Preliminary Report on Patentability in International Application No. PCT/US2021/013438, dated Jul. 28, 2022, 7 pages.
International Search Report and Written Opinion in International Application No. PCT/US2022/024210, dated Jun. 28, 2022, 14 pages.
Israeli Office Action in Israeli Application No. 289834 dated Jul. 14, 2022, 4 pages.
Japanese Office Action in Japanese Application No. 2019-565177, dated May 13, 2022, 11 pages.
Korean Office Action in Korean Application No. 10-2022-7018808, dated Sep. 16, 2022, 5 pages.
Mexican Office Action in Mexican Application No. MX/a/2019/014097, dated Aug. 11, 2022, 13 pages.
Peterson et al., Expanding the Scope of Crystal Form Evaluation in Pharmaceutical Science, J Pharm Pharmaceut Sci., 9(3): 317-326.
Philippine Allowance in Philippine Application No. 1/2015/502383, dated Jun. 6, 2022, 2 pages.
Porta, "FGFR a promising druggable target in cancer: Molecular biology and new drugs." Critical reviews in oncology hematology, 2017, 113:256-267.
Ukraine Office Action in Ukraine Application No. a202007700, dated Sep. 13, 2022, 11 pages.
Vietnamese Office Action in Vietnamese Application No. 1-2022-03016, dated Jul. 8, 2022, 2 pages.

METHODS OF TREATING CANCER WITH AN FGFR INHIBITOR

FIELD OF THE INVENTION

This application relates to methods of treating cancer in a patient in need thereof, comprising administering a Fibroblast Growth Factor Receptors (FGFR) inhibitor to the patient.

BACKGROUND OF THE INVENTION

The Fibroblast Growth Factor Receptors (FGFR) are receptor tyrosine kinases that bind to fibroblast growth factor (FGF) ligands. There are four FGFR proteins (FGFR1-4) that are capable of binding ligands and are involved in the regulation of many physiological processes including tissue development, angiogenesis, wound healing, and metabolic regulation. Upon ligand binding, the receptors undergo dimerization and phosphorylation leading to stimulation of the protein kinase activity and recruitment of many intracellular docking proteins. These interactions facilitate the activation of an array of intracellular signaling pathways including Ras-MAPK, AKT-PI3K, and phospholipase C that are important for cellular growth, proliferation and survival (Reviewed in Eswarakumar et al. Cytokine & Growth Factor Reviews, 2005).

Aberrant activation of this pathway either through overexpression of FGF ligands or FGFR or activating mutations in the FGFRs can lead to tumor development, progression, and resistance to conventional cancer therapies. In human cancer, genetic alterations including gene amplification, chromosomal translocations and somatic mutations that lead to ligand-independent receptor activation have been described. Large scale DNA sequencing of thousands of tumor samples has revealed that components of the FGFR pathway are among the most frequently mutated in human cancer. Many of these activating mutations are identical to germline mutations that lead to skeletal dysplasia syndromes. Mechanisms that lead to aberrant ligand-dependent signaling in human disease include overexpression of FGFs and changes in FGFR splicing that lead to receptors with more promiscuous ligand binding abilities (Reviewed in Knights and Cook Pharmacology & Therapeutics, 2010; Turner and Grose, Nature Reviews Cancer, 2010). Therefore, development of inhibitors targeting FGFR may be useful in the clinical treatment of diseases that have elevated FGF or FGFR activity.

The cancer types in which FGF/FGFRs are implicated include, but are not limited to: carcinomas (e.g., bladder, breast, cervical, colorectal, endometrial, gastric, head and neck, kidney, liver, lung, ovarian, prostate); hematopoietic malignancies (e.g., multiple myeloma, chronic lymphocytic lymphoma, adult T cell leukemia, acute myelogenous leukemia, non-Hodgkin lymphoma, myeloproliferative neoplasms, and Waldenstrom's Macroglubulinemia); and other neoplasms (e.g., glioblastoma, melanoma, and rhabdosarcoma). In addition to a role in oncogenic neoplasms, FGFR activation has also been implicated in skeletal and chondrocyte disorders including, but not limited to, achrondroplasia and craniosynostosis syndromes.

The FGFR4-FGF19 signaling axis, specifically, has been implicated in the pathogenesis of a number of cancers including hepatocellular carcinoma (Heinzle et al., Cur. Pharm. Des. 2014, 20:2881). Ectopic expression of FGF19 in transgenic mice was shown to lead to tumor formation in the liver and a neutralizing antibody to FGF19 was found to inhibit tumor growth in mice. In addition, overexpression of FGFR4 has been observed in a multiple tumor types including hepatocellular carcinoma, colorectal, breast, pancreatic, prostate, lung, and thyroid cancers. Furthermore, activating mutations in FGFR4 have been reported in rhabdomyosarcoma (Taylor et al. JCI 2009, 119:3395).

Inhibitors of FGFR are currently being developed for the treatment of cancer. For example, pemigatinib, or 3-(2,6-difluoro-3,5-dimethoxyphenyl)-1-ethyl-8-(morpholin-4-yl-methyl)-1,3,4,7-tetrahydro-2H-pyrrolo[3',2': 5,6]pyrido[4,3-d]pyrimidin-2-one, and other small molecule inhibitors of FGFR are reported in e.g., U.S. Pat. No. 9,611,267, and US Publication Nos.: 2012/0165305; 2014/0045814; 2013/0338134; 2014/0171405; 2014/0315902; 2016/0115164; 2016/0244448; 2016/0244449; and 2016/0244450; and U.S. Provisional Application Nos. 62/667,166 and 62/667,040 (corresponding to US Publication Nos.: 2019/0337948 and 2020/0002338, respectively).

It has been estimated that 6.5-23% of adverse reactions from exposure to multiple drugs results from drug-drug interactions. Each year, a number of deaths occur as a result of patients adding concomitant prescription pharmaceutical products to their existing medication regimen. Thus, there needs for increased understanding of drug-drug interactions and improved methods for administering cancer therapeutics (e.g., pemigatinib) to individuals who are concomitantly being treated with other active agents.

SUMMARY OF THE INVENTION

Provided herein is a method of treating cancer comprising administering a therapy to a patient in need thereof, wherein the therapy comprises administering a therapeutically effective amount of pemigatinib to the patient while avoiding the concomitant administration of a CYP3A4 perpetrator.

Also provided herein is a method of treating cancer comprising administering a therapy to a patient in need thereof, wherein the therapy comprises:

(a) determining if the patient is receiving administration of a CYP3A4 perpetrator; and (b) administering a therapeutically effective amount of pemigatinib to the patient while avoiding the concomitant administration of the CYP3A4 perpetrator.

Also provided herein is a method of treating cancer comprising administering a therapy to a patient in need thereof, wherein the therapy comprises:

(a) discontinuing administration of a CYP3A4 perpetrator to the patient for a time period of about 5 or more half-lives of the CYP3A4 perpetrator; and (b) administering a therapeutically effective amount of pemigatinib to the patient.

In some embodiments, the CYP3A4 perpetrator is a strong CYP3A4 inhibitor. In some embodiments, the CYP3A4 perpetrator is a moderate to strong CYP3A4 inducer.

Provided herein is a method of treating cancer comprising administering a therapy to a patient in need thereof, wherein the therapy comprises:

(a) determining if the patient is receiving administration of a strong CYP3A4 inhibitor; and (b) administering a therapeutically effective amount of pemigatinib to the patient while avoiding the concomitant administration of a strong CYP3A4 inhibitor.

Provided herein is a method of treating cancer comprising administering a therapy to a patient in need thereof, wherein the therapy comprises:

(a) determining if the patient is receiving administration of a moderate to strong CYP3A4 inducer; and (b) administering a therapeutically effective amount of pemigatinib to the patient while avoiding the concomitant administration of a moderate to strong CYP3A4 inducer.

DETAILED DESCRIPTION

Figure 1:
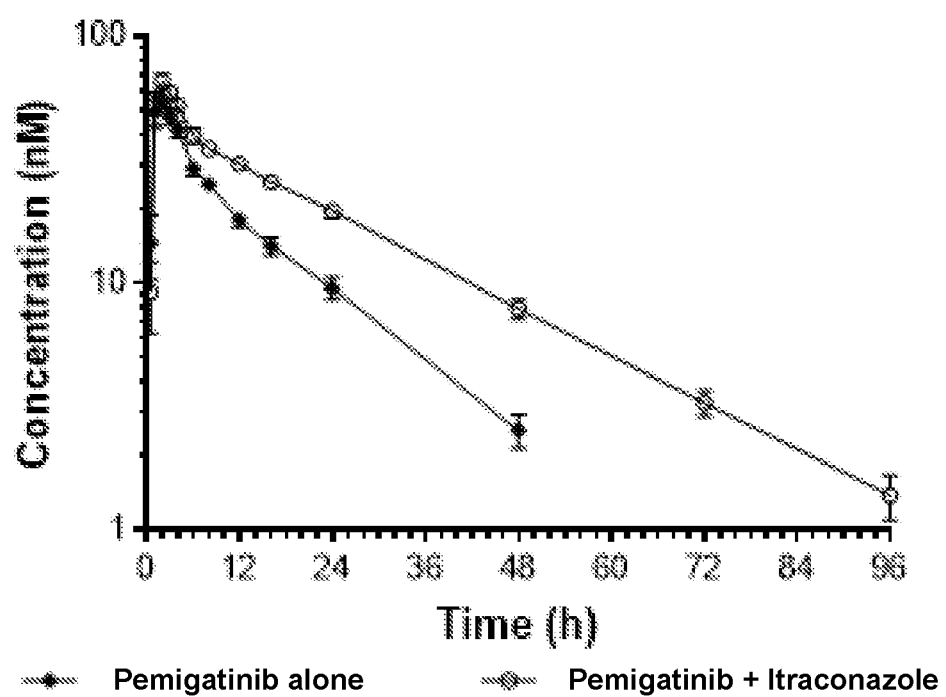
FIG. 1 shows the plasma concentration of pemigatinib in healthy volunteers after administration of pemigatinib with or without coadministration of itraconazole.

The present disclosure is directed to, inter alia, methods of treating cancer in a patient in need thereof, comprising administering pemigatinib, which is 3-(2,6-difluoro-3,5-dimethoxyphenyl)-1-ethyl-8-(morpholin-4-ylmethyl)-1,3,4,7-tetrahydro-2H-pyrrolo[3',2': 5,6]pyrido[4,3-d]pyrimidin-2-one, having the structure shown below:

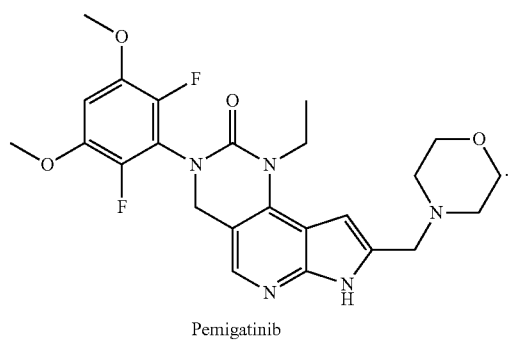 [SMILES: CCN1C(=O)N(c2c(F)c(OC)cc(OC)c2F)Cc2cnc3[nH]c(CN4CCOCC4)cc3c21]

Pemigatinib

Pemigatinib is described in U.S. Pat. No. 9,611,267, the entirety of which is incorporated herein by reference. Pemigatinib is further described in US Publication Nos.: 2019/0337948 and 2020/0002338, the entireties of which are incorporated herein by reference.

Provided herein is a method of treating cancer comprising administering a therapy to a patient in need thereof, wherein the therapy comprises administering a therapeutically effective amount of pemigatinib to the patient while avoiding the concomitant administration of a CYP3A4 perpetrator.

Also provided herein is a method of treating cancer comprising administering a therapy to a patient in need thereof, wherein the therapy comprises:

(a) determining if the patient is receiving administration of a CYP3A4 perpetrator; and
(b) administering a therapeutically effective amount of pemigatinib to the patient while avoiding the concomitant administration of the CYP3A4 perpetrator.

Also provided herein is a method of treating cancer comprising administering a therapy to a patient in need thereof, wherein the therapy comprises:
(a) discontinuing administration of a CYP3A4 perpetrator to the patient for a time period of about 5 or more half-lives of the CYP3A4 perpetrator; and
(b) administering a therapeutically effective amount of pemigatinib to the patient.

Also provided herein is a method of treating cancer comprising administering a therapy to a patient in need thereof, wherein the therapy comprises:
(a) discontinuing administration of a CYP3A4 perpetrator to the patient for a time period, wherein the time period is the shorter of i) about 5 or more half-lives of the CYP3A4 perpetrator and ii) 14 days; and
(b) administering a therapeutically effective amount of pemigatinib to the patient.

In some embodiments, the CYP3A4 perpetrator is a strong CYP3A4 inhibitor. In some embodiments, the CYP3A4 perpetrator is a moderate to strong CYP3A4 inducer.

In some embodiments, provided herein is a method of treating cancer comprising administering a therapy to a patient in need thereof, wherein the therapy comprises administering a therapeutically effective amount of pemigatinib to the patient while avoiding the concomitant administration of a strong CYP3A4 inhibitor.

In some embodiments, provided herein is a method of treating cancer comprising administering a therapy to a patient in need thereof, wherein the therapy comprises administering a therapeutically effective amount of pemigatinib to the patient while avoiding the concomitant administration of itraconazole.

In some embodiments, provided herein is a method of treating cancer comprising administering a therapy to a patient in need thereof, wherein the therapy comprises:
(a) determining if the patient is receiving administration of a strong CYP3A4 inhibitor; and
(b) administering a therapeutically effective amount of pemigatinib to the patient while avoiding the concomitant administration of a strong CYP3A4 inhibitor.

Also provided herein is a method of treating cancer comprising administering a therapy to a patient in need thereof, wherein the therapy comprises:
(a) discontinuing administration of a strong CYP3A4 inhibitor to the patient for a time period of about 5 or more half-lives of the strong CYP3A4 inhibitor; and
(b) administering a therapeutically effective amount of pemigatinib to the patient.

In some embodiments, the time period of discontinuing administration of a strong CYP3A4 inhibitor to the patient is 6 or more half-lives of the strong CYP3A4 inhibitor.

In some embodiments, the time period of discontinuing administration of a strong CYP3A4 inhibitor to the patient is 7 or more half-lives of the strong CYP3A4 inhibitor.

Also provided herein is a method of treating cancer comprising administering a therapy to a patient in need thereof, wherein the therapy comprises:
(a) discontinuing administration of a strong CYP3A4 inhibitor to the patient for a time period of about 5 or more half-lives of the strong CYP3A4 inhibitor; and
(b) administering a therapeutically effective amount of pemigatinib to the patient while avoiding the administration of the strong CYP3A4 inhibitor during treatment.

Also provided herein is a method of treating cancer in a patient in need thereof, comprising orally administering an adjusted daily dosage amount of pemigatinib to the patient who is receiving concomitant administration of a strong CYP3A4 inhibitor, wherein the adjusted daily dosage amount of pemigatinib is about 25% to about 75% of an intended daily dosage amount of pemigatinib, and wherein:
(a) the intended daily dosage amount of pemigatinib is a dosage amount suitable for the patient if the patient is not receiving a concomitant strong CYP3A4 inhibitor; or
(b) the intended daily dosage amount of pemigatinib is about 9 mg to 13.5 mg for an adult patient.

In some embodiments, the administration of pemigatinib comprises:
(a) a continuous daily administration of an intended amount or adjusted amount of pemigatinib to the patient in need thereof; or
(b) a 21-day dosing cycle comprising: 14 days of daily administration of an intended amount or adjusted amount of pemigatinib to the patient in need thereof and 7 days without administration of pemigatinib.

In some embodiments, the adjusted daily dosage amount of pemigatinib is about 40% to about 70% of the intended dosage amount of pemigatinib. In some embodiments, the adjusted daily dosage amount of pemigatinib is about 50% of the intended dosage amount of pemigatinib. In some embodiments, the adjusted daily dosage amount of pemigatinib is about 60% to about 70% of the intended dosage amount of pemigatinib. In some embodiments, the adjusted daily dosage amount of pemigatinib is about 25%, about 30%, about 40%, about 50%, about 60%, about 70%, or about 75% of the intended dosage amount of pemigatinib.

In some embodiments, the intended daily dosage amount of pemigatinib is the dosage amount suitable for the patient if the patient is not receiving administration of a strong CYP3A4 inhibitor. In some embodiments, the intended daily dosage of pemigatinib is about 9 mg to about 13.5 mg. In some embodiments, the adjusted daily dosage amount of pemigatinib is about 9 mg for patients on an intended dose of about 13.5 mg of pemigatinib. In some embodiments, the adjusted daily dosage amount of pemigatinib is about 4.5 mg for patients on an intended dose of about 9 mg of pemigatinib. In some embodiments, the adjusted daily dosage amount of pemigatinib is about 4.5 mg to about 9 mg.

In some embodiments, the concomitant administration of pemigatinib and a strong CYP3A4 inhibitor provides an altered therapeutic effect or adverse reaction profile of pemigatinib.

Also provided herein is a method of treating cancer in a patient in need thereof, wherein the method comprises orally administering a therapeutically effective amount of pemigatinib to the patient and any one or more of the following:
(a) advising the patient that strong CYP3A4 inhibitors should be avoided or discontinued;
(b) advising the patient that use of pemigatinib in patients being treated with strong CYP3A4 inhibitors is contraindicated;
(c) advising the patient that the concomitant administration of pemigatinib and strong CYP3A4 inhibitors can alter the therapeutic effect of pemigatinib;
(d) advising the patient that strong CYP3A4 inhibitors should be used with caution in patients receiving pemigatinib due to the potential for reduced pemigatinib clearance;

(e) advising the patient that the concomitant administration of pemigatinib and strong CYP3A4 inhibitors resulted in about 2-fold decrease in pemigatinib clearance; or (f) advising the patient that the concomitant administration of pemigatinib and strong CYP3A4 inhibitors resulted in about 2-fold increase in exposure to pemigatinib.

In some embodiments, the method comprises advising the patient that strong CYP3A4 inhibitors should be avoided or discontinued. In some embodiments, the method comprises advising the patient that use of pemigatinib in patients being treated with strong CYP3A4 inhibitors is contraindicated. In some embodiments, the method comprises advising the patient that the concomitant administration of pemigatinib and strong CYP3A4 inhibitors can alter the therapeutic effect of pemigatinib. In some embodiments, the method comprises advising the patient that the concomitant administration of pemigatinib and strong CYP3A4 inhibitors resulted in about 2-fold increase in exposure to pemigatinib. In some embodiments, the method comprises advising the patient that strong CYP3A4 inhibitors should be used with caution in patients receiving pemigatinib due to the potential for reduced pemigatinib clearance. In some embodiments, the method comprises advising the patient that the concomitant administration of pemigatinib and strong CYP3A4 inhibitors resulted in about 2-fold decrease in pemigatinib clearance.

In some embodiments, the adjusted daily dosage amount of pemigatinib is the amount that provides $t_{1/2}$ values substantially the same as $t_{1/2}$ values when pemigatinib is administered alone. In some embodiments, the targeted $t_{1/2}$ value for a patient who is also receiving concomitant administration of pemigatinib and a strong CYP3A4 inhibitor is substantially the same as the $t_{1/2}$ value if the patient is receiving administration of pemigatinib alone. In some embodiments, the $t_{1/2}$ when 4.5 mg of pemigatinib is administered alone is about 12 hours. In some embodiments, the $t_{1/2}$ when 4.5 mg of pemigatinib is administered alone is about 11 hours to about 13 hours. In some embodiments, the $t_{1/2}$ when 4.5 mg of pemigatinib is administered alone is about 10 hours to about 14 hours. In some embodiments, the $t_{1/2}$ when 13.5 mg of pemigatinib is administered alone is about 13 hours. In some embodiments, the $t_{1/2}$ when 13.5 mg of pemigatinib is administered alone is about 12 hour to about 14 hours. In some embodiments, the $t_{1/2}$ when 13.5 mg of pemigatinib is administered alone is about 11 hours to about 15 hours. In some embodiments, the $t_{1/2}$ when 13.5 mg of pemigatinib is administered alone is about 10 hours to about 16 hours.

In some embodiments, the adjusted daily dosage amount of pemigatinib is the amount that provides $C_{max}$ values substantially the same as $C_{max}$ values when pemigatinib is administered alone. In some embodiments, the targeted $C_{max}$ value for a patient who is also receiving concomitant administration of pemigatinib and a strong CYP3A4 inhibitor is substantially the same as the $C_{max}$ value if the patient is receiving administration of pemigatinib alone. In some embodiments, the $C_{max}$ when 4.5 mg of pemigatinib is administered alone is about 40 nM to about 80 nM. In some embodiments, the $C_{max}$ when 4.5 mg of pemigatinib is administered alone is about 50 nM to about 70 nM. In some embodiments, the $C_{max}$ when 4.5 mg of pemigatinib is administered alone is about 55 nM to about 65 nM. In some embodiments, the $C_{max}$ when 4.5 mg of pemigatinib is administered alone is about 60 nM. In some embodiments, the $C_{max}$ when 4.5 mg of pemigatinib is administered alone is from about 20 to about 120 nM.

In some embodiments, the $C_{max}$ when 9 mg of pemigatinib is administered alone is from about 50 to about 450 nM.

In some embodiments, the $C_{max}$ when 13.5 mg of pemigatinib is administered alone is about 190 nM to about 210 nM. In some embodiments, the $C_{max}$ when 13.5 mg of pemigatinib is administered alone is about 195 nM to about 205 nM. In some embodiments, the $C_{max}$ when 13.5 mg of pemigatinib is administered alone is about 200 nM. In some embodiments, the $C_{max}$ when 13.5 mg of pemigatinib is administered alone is about 90 nM to about 300 nM. In some embodiments, the $C_{max}$ when 13.5 mg of pemigatinib is administered alone is about 70 nM to about 700 nM.

In some embodiments, the adjusted daily dosage amount of pemigatinib is the amount that provides $AUC_{0-\infty}$ values substantially the same as $AUC_{0-\infty}$ values when pemigatinib is administered alone. In some embodiments, the targeted $AUC_{0-\infty}$ value for a patient who is also receiving concomitant administration of pemigatinib and a strong CYP3A4 inhibitor is substantially the same as the $AUC_{0-\infty}$ value if the patient is receiving administration of pemigatinib alone. In some embodiments, the $AUC_{0-\infty}$ when 4.5 mg of pemigatinib is administered alone is about 500 nM·h to about 900 nM·h. In some embodiments, the $AUC_{0-\infty}$ when 4.5 mg of pemigatinib is administered alone is about 600 nM·h to about 800 nM·h. In some embodiments, the $AUC_{0-\infty}$ when 4.5 mg of pemigatinib is administered alone is about 650 nM·h to about 750 nM·h. In some embodiments, the $AUC_{0-\infty}$ when 4.5 mg of pemigatinib is administered alone is about 700 nM·h. In some embodiments, the $AUC_{0-\infty}$ when 4.5 mg of pemigatinib is administered alone is about 430 nM·h to about 1180 nM·h. In some embodiments, the $AUC_{0-\infty}$ when 4.5 mg of pemigatinib is administered alone is about 1100 nM·h to about 1300 nM h.

In some embodiments, the $AUC_{0-\infty}$ when 9 mg of pemigatinib is administered alone is about 250 nM·h to about 7000 nM·h.

In some embodiments, the $AUC_{0-\infty}$ when 13.5 mg of pemigatinib is administered alone is about 1700 nM·h to about 2100 nM·h. In some embodiments, the $AUC_{0-\infty}$ when 13.5 mg of pemigatinib is administered alone is about 1800 nM·h to about 2000 nM·h. In some embodiments, the $AUC_{0-\infty}$ when 13.5 mg of pemigatinib is administered alone is about 1850 nM·h to about 1950 nM·h. In some embodiments, the $AUC_{0-\infty}$ when 13.5 mg of pemigatinib is administered alone is about 1900 nM·h. In some embodiments, the $AUC_{0-\infty}$ when 13.5 mg of pemigatinib is administered alone is about 900 nM·h to about 13000 nM·h.

Also provided herein is a method of treating cancer comprising administering a therapy to a patient in need thereof, wherein the therapy comprises the concomitant administering of a therapeutically effective amount of pemigatinib and a mild to moderate CYP3A4 inhibitor, and wherein the concomitant administration provides substantially the same therapeutic effect or adverse reaction profile of pemigatinib compared to when pemigatinib is administered alone.

Also provided herein is a method of treating cancer comprising administering a therapy to a patient in need thereof, wherein the therapy comprises the concomitant administering of a therapeutically effective amount of pemigatinib and a mild to moderate CYP3A4 inhibitor, wherein the concomitant administering demonstrated no significant pharmacokinetic interaction.

Provided herein is a method of treating cancer comprising administering a therapy to a patient in need thereof, wherein the therapy comprises administering a therapeutically effective amount of pemigatinib to the patient while avoiding the concomitant administration of a moderate to strong CYP3A4 inducer.

Provided herein is a method of treating cancer comprising administering a therapy to a patient in need thereof, wherein the therapy comprises administering a therapeutically effective amount of pemigatinib to the patient while avoiding the concomitant administration of rifampin.

Provided herein is a method of treating cancer comprising administering a therapy to a patient in need thereof, wherein the therapy comprises:

(a) determining if the patient is receiving administration of a moderate to strong CYP3A4 inducer; and (b) administering a therapeutically effective amount of pemigatinib to the patient while avoiding the concomitant administration of a moderate to strong CYP3A4 inducer.

Also provided herein is a method of treating cancer comprising administering a therapy to a patient in need thereof, wherein the therapy comprises:

(a) discontinuing administration of a moderate to strong CYP3A4 inducer to the patient for a time period of about 5 or more half-lives of the moderate to strong CYP3A4 inducer; and (b) administering a therapeutically effective amount of pemigatinib to the patient.

In some embodiments, the time period of discontinuing administration of a moderate to strong CYP3A4 inducer to the patient is 6 or more half-lives of the moderate to strong CYP3A4 inducer. In some embodiments, the time period of discontinuing administration of a moderate to strong CYP3A4 inducer to the patient is 7 or more half-lives of the moderate to strong CYP3A4 inducer.

Also provided herein is a method of treating cancer comprising administering a therapy to a patient in need thereof, wherein the therapy comprises:

(a) discontinuing administration of a moderate to strong CYP3A4 inducer to the patient for a time period of about 5 or more half-lives of the moderate to strong CYP3A4 inducer; and (b) administering a therapeutically effective amount of pemigatinib to the patient while avoiding the administration of the moderate to strong CYP3A4 inducer during treatment.

In some embodiments, the total daily amount of pemigatinib is about 9 mg to about 13.5 mg.

In some embodiments, the concomitant administration of pemigatinib and a moderate to strong CYP3A4 inducer provides an altered therapeutic effect of pemigatinib.

Also provided herein is a method of treating cancer in a patient in need thereof, wherein the method comprises orally administering a therapeutically effective amount of pemigatinib to the patient and any one or more of the following:

(a) advising the patient that moderate to strong CYP3A4 inducers should be avoided or discontinued;

(b) advising the patient that use of pemigatinib in patients being treated with moderate to strong CYP3A4 inducers is contraindicated;

(c) advising the patient that the concomitant administration of pemigatinib and moderate to strong CYP3A4 inducers can alter the therapeutic effect of pemigatinib;

(d) advising the patient that moderate to strong CYP3A4 inducers should be used with caution in patients receiving pemigatinib due to the potential for increased pemigatinib clearance;

(e) advising the patient that the concomitant administration of pemigatinib and strong CYP3A4 inducers resulted in about 6-fold to about 7-fold increase in pemigatinib clearance; or (f) advising the patient that the concomitant administration of pemigatinib and moderate to strong CYP3A4 inducers resulted in about 6-fold to about 7-fold decrease in exposure to pemigatinib.

In some embodiments, the method further comprises advising the patient that moderate to strong CYP3A4 inducers should be avoided or discontinued. In some embodiments, the method comprises advising the patient that use of pemigatinib in patients being treated with moderate to strong CYP3A4 inducers is contraindicated. In some embodiments, the method comprises advising the patient that the concomitant administration of pemigatinib and moderate to strong CYP3A4 inducers can alter the therapeutic effect of pemigatinib. In some embodiments, the method comprises advising the patient that moderate to strong CYP3A4 inducers should be used with caution in patients receiving pemigatinib due to the potential for increased pemigatinib clearance. In some embodiments, the method comprises advising the patient that the concomitant administration of pemigatinib and strong CYP3A4 inducers resulted in about 6-fold to about 7-fold increase in pemigatinib clearance. In some embodiments, the method comprises advising the patient that the concomitant administration of pemigatinib and moderate to strong CYP3A4 inducers resulted in about 6-fold to about 7-fold decrease in exposure to pemigatinib. In some embodiments, the method comprises advising the patient that the concomitant administration of pemigatinib and moderate to strong CYP3A4 inducers resulted in about 2-fold decrease in exposure to pemigatinib. In some embodiments, the method comprises advising the patient that the concomitant administration of pemigatinib and moderate to strong CYP3A4 inducers resulted in about 7-fold decrease in exposure to pemigatinib.

Also provided herein is a method of treating cancer comprising administering a therapy to a patient in need thereof, wherein the therapy comprises the concomitant administering a therapeutically effective amount of pemigatinib and a mild CYP3A4 inducer, and wherein the concomitant administration provides substantially the same therapeutic effect or adverse reaction profile of pemigatinib compared to when pemigatinib is administered alone.

Also provided herein is a method of treating cancer comprising administering a therapy to a patient in need thereof, wherein the therapy comprises the concomitant administering of a therapeutically effective amount of pemigatinib and a mild CYP3A4 inducer, wherein the concomitant administering demonstrated no significant pharmacokinetic interaction.

Also provided herein is a method of increasing the effectiveness of pemigatinib therapy by avoiding decreased exposure to pemigatinib, in a patient in need of pemigatinib therapy that is receiving a moderate to strong CYP3A4 inducer comprising discontinuing the moderate to strong CYP3A4 inducer to decrease the levels of CYP3A4 induction, and then administering a therapeutically effective amount of pemigatinib.

In some embodiments, the time period of discontinuing administration of a moderate to strong CYP3A4 inducer is 5 or more half-lives of the moderate to strong CYP3A4 inducer. In some embodiments, the time period of discontinuing administration of a moderate to strong CYP3A4 inducer is 6 or more half-lives of the moderate to strong CYP3A4 inducer. In some embodiments, the time period of discontinuing administration of a moderate to strong CYP3A4 inducer is 7 or more half-lives of the moderate to strong CYP3A4 inducer. In some embodiments, the time period of discontinuing administration of a moderate to strong CYP3A4 inducer is two to three weeks prior to pemigatinib administration.

Also provided herein is a method of treating a patient with pemigatinib wherein the patient is coadministering a substance that is a known strong inhibitor of CYP3A4, said method comprising adjusting administration to the patient of the substance to avoid an adverse event associated with a change in the metabolism of pemigatinib.

Also provided herein is a method of treating a patient with pemigatinib wherein the patient is coadministering a substance that is a known strong inhibitor or a known moderate to strong inducer of CYP3A4, said method comprising adjusting administration of pemigatinib or the substance to the patient to avoid an adverse reaction or a subtherapeutic outcome with pemigatinib.

In some embodiments, the adjusting administration of pemigatinib is a dosage amount suitable for the patient if the patient is not receiving a concomitant strong CYP3A4 inhibitor. In some embodiments, the adjusting administration of the substance is avoiding the coadministration of the substance that is a known moderate to strong inducer of CYP3A4.

Also provided herein is a method of avoiding an adverse event when administering pemigatinib, comprising determining that a patient in need of pemigatinib therapy is taking a substance that is a known strong inhibitor or a known moderate to strong inducer of CYP3A4; and adjusting administration to the patient of pemigatinib or the substance to avoid an adverse event associated with a change in the metabolism of pemigatinib, wherein the adjusting administration comprises ceasing to administer the substance if the substance is a moderate to strong inducer of CYP3A4 or decreasing the dosage of pemigatinib if the substance is a strong inhibitor of CYP3A4.

Also provided herein is a method of avoiding an adverse event when administering pemigatinib, comprising avoiding coadministration of pemigatinib with moderate to strong CYP3A4 inducers or strong CYP3A4 inhibitors.

Also provided herein is a method of avoiding an adverse event when administering pemigatinib, comprising avoiding concomitant administration of pemigatinib with moderate to strong CYP3A4 inducers or strong CYP3A4 inhibitors.

Also provided herein is a method of avoiding an adverse event when administering pemigatinib, comprising avoiding concomitant use of pemigatinib with moderate to strong CYP3A4 inducers or strong CYP3A4 inhibitors.

Exemplary CYP3A inhibitors (e.g., strong CYP3A4 inhibitors, moderate CYP3A4 inhibitors, and mild CYP3A4 inhibitors) are shown below in the following table.

TABLE 1

| CYP3A Inhibitors | |
|---|---|
| Inhibitor | Therapeutic Class |
| Strong CYP3A Inhibitors | |
| VIEKIRA PAK | Antivirals |
| Indinavir/RIT | Protease inhibitors |
| Tipranavir/RIT | Protease inhibitors |
| Ritonavir | Protease inhibitors |
| Ketoconazole | Antifungals |
| Indinavir | Protease inhibitors |
| Troleandomycin | Antibiotics |
| Telaprevir | Antivirals |
| Danoprevir/RIT | Antivirals |
| Elvitegravir/RIT | Treatments of AIDS |
| Saquinavir/RIT | Protease inhibitors |
| Lopinavir/RIT | Protease inhibitors |
| Itraconazole | Antifungals |
| Voriconazole | Antifungals |
| Mibefradil | Calcium channel blockers |
| Clarithromycin | Antibiotics |
| Posaconazole | Antifungals |
| Telithromycin | Antibiotics |
| Grapefruit juice DS | Food products |
| Conivaptan | Diuretics |
| Nefazodone | Antidepressants |
| Nelfinavir | Protease inhibitors |
| Saquinavir | Protease inhibitors |
| Ribociclib | Kinase inhibitors |
| Idelalisib | Kinase inhibitors |
| Boceprevir | Antivirals |
| Moderate CYP3A Inhibitors | |
| Erythromycin | Antibiotics |
| Fluconazole | Antifungals |
| Atazanavir/RIT | Protease inhibitors |
| Darunavir | Protease inhibitors |
| Diltiazem | Calcium channel blockers |
| Darunavir/RIT | Protease inhibitors |
| Dronedarone | Antiarrhythmics |
| Crizotinib | Kinase inhibitors |
| Atazanavir | Protease inhibitors |
| Letermovir | Antivirals |
| Aprepitant | Antiemetics |
| Casopitant | Antiemetics |
| Amprenavir | Protease inhibitors |
| Faldaprevir | Antivirals |
| Imatinib | Antineoplastic agents |
| Verapamil | Calcium channel blockers |
| Netupitant | Antiemetics |
| Nilotinib | Kinase inhibitors |
| Grapefruit juice | Food products |
| Tofisopam | Benzodiazepines |
| Cyclosporine | Immunosuppressants |
| ACT-178882 | Renin inhibitors |
| Ciprofloxacin | Antibiotics |
| Magnolia vine (*Schisandra sphenanthera*) | Herbal medications |
| Isavuconazole | Antifungals |
| Cimetidine | H-2 receptor antagonists |
| Mild CYP3A Inhibitors | |
| Tabimorelin | Hormone replacement |
| Amlodipine | Calcium channel blockers |
| Ranolazine | Cardiovascular drugs |
| Breviscapine | Herbal medications |
| Lomitapide | Other antilipemics |
| Fosaprepitant (IV) | Antiemetics |
| Seville orange (*Citrus aurantium*) juice | Food products |
| Amiodarone | Antiarrhythmics |
| Diosmin | Herbal medications |
| Chlorzoxazone | Muscle relaxants |
| Fluvoxamine | Antidepressants |
| Ranitidine | H-2 receptor antagonists |
| Goldenseal | Herbal medications |
| Clotrimazole | Antifungals |
| Tacrolimus | Immunosuppressants |
| Palbociclib | Kinase inhibitors |
| Cilostazol | Antiplatelets |
| Ticagrelor | Antiplatelets |
| Peppermint oil | Food products |
| Ivacaftor | Cystic fibrosis treatments |
| Guan Mai Ning | Herbal medications |
| Osilodrostat | Adrenal steroidogenesis inhibitors |
| Piperine | Food products |
| Resveratrol | Food products |
| Roxithromycin | Antibiotics |
| Suvorexant | Hypnotics - sedatives |
| Propiverine | Anticholinergics |
| Isoniazid | Antibiotics |

TABLE 1-continued

CYP3A Inhibitors

| Inhibitor | Therapeutic Class |
|---|---|
| Berberine | Herbal medications |
| Oral contraceptives | Oral contraceptives |
| Delavirdine | NNRTIs |
| Daclatasvir | Antivirals |
| Simeprevir | Protease inhibitors |
| Atorvastatin | HMG CoA reductase inhibitors (statins) |
| Tolvaptan | Vasopressin antagonists |
| Almorexant | Hypnotics - sedatives |
| Evacetrapid | CETP inhibitors |
| Linagliptin | Dipeptidyl peptidase 4 inhibitors |
| Grazoprevir (ingredient of Zepatier) | Antivirals |
| Lacidipine | Calcium channel blockers |
| Cranberry juice | Food products |
| Pazopanib | Kinase inhibitors |
| Fostamatinib | Other |
| Everolimus | Immunosuppressants |
| Blueberry juice | Food products |
| Flibanserin | Central nervous system agents |
| Lapatinib | Kinase Inhibitors |
| Brodalumab | Immunomodulators biologics |
| Alprazolam | Benzodiazepines |
| Tong Xin Luo | Herbal medications |
| Glecaprevir and pibrentasvir | Antivirals |
| Bicalutamide | Antiandrogens |
| Sitaxentan | Endothelin receptor antagonists |
| Azithromycin | Antibiotics |
| Obeticholic acid | Miscellaneous agents |
| Ginkgo | Herbal medications |
| Teriflunomide | Other immunomodulators |

In some embodiments, the strong CYP3A4 inhibitor is itraconazole, ketoconazole or clarithromycin. In some embodiments, the strong CYP3A4 inhibitor is itraconazole. In some embodiments, the moderate CYP3A4 inhibitor is erythromycin or diltiazem. In some embodiments, the mild CYP3A4 inhibitor is fluvoxamine. In some embodiments, the CYP3A4 inhibitor is erythromycin, diltiazem, or fluvoxamine.

Exemplary CYP3A inducers (e.g., strong CYP3A4 inducers, moderate CYP3A4 inducers, and mild CYP3A4 inducers) are shown below in the following table.

TABLE 2

| Inducers | Therapeutic class |
|---|---|
| Strong CYP3A Inducers | |
| Rifampin | Antibiotics |
| Mitotane | Other Antineoplastics |
| Avasimibe | Other Antilipemics |
| Rifapentine | Antibiotics |
| Apalutamide | Antiandrogens |
| Phenytoin | Anticonvulsants |
| Carbamazepine | Anticonvulsants |
| Enzalutamide | Antiandrogens |
| St John's Wort extract | Herbal medications |
| Lumacaftor | Cystic fibrosis treatments |
| Rifabutin | Antibiotics |
| Phenobarbital | Anticonvulsants |
| Moderate CYP3A Inducers | |
| Ritonavir and St. Johns wort | None |
| Semagacestat | Alzheimer's treatments |
| Efavirenz | NNRTIs |
| Tipranavir and ritonavir | Protease inhibitors |
| Dabrafenib | Kinase inhibitors |
| Lesinurad | Antigout and uricosuric agents |
| Bosentan | Endothelin receptor antagonists |
| Genistein | Food products |

TABLE 2-continued

| Inducers | Therapeutic class |
|---|---|
| Thioridazine | Antipsychotics |
| Nafcillin | Antibiotics |
| Talviraline | NNRTIs |
| Lopinavir | Protease inhibitors |
| Modafinil | Psychostimulants |
| Etravirine | NNRTIs |
| Lersivirine | NNRTIs |
| Telotristat ethyl | Antidiarrheals |
| Mild CYP3A Inducers | |
| Eslicarbazepine | Anticonvulsants |
| Telaprevir | Antivirals |
| Daclatasvir and asunaprevir and beclabuvir | Antivirals |
| Amenamevir | Antivirals |
| Garlic | Food products |
| Bexarotene | Other antineoplastics |
| Sarilumab | Immunomodulators biologics |
| Artesunate and mefloquine | Antimalarials |
| Amprenavir (fosamprenavir) | Protease inhibitors |
| Raltegravir | HIV-integrase strand transfer inhibitors |
| Vemurafenib | Kinase inhibitors |
| Troglitazone | Thiazolidinediones |
| Dicloxacillin | Antibiotics |
| Sorafenib | Kinase inhibitors |
| Rufinamide | Anticonvulsants |
| Sirukumab | Immunomodulators biologics |
| Pleconaril | Antivirals |
| Ginseng | Herbal medications |
| Boceprevir | Antivirals |
| Sulfinpyrazone | Antigout and uricosuric agents |
| Ginkgo | Herbal medications |
| Vinblastine | Vinca alkaloids |
| Nevirapine | NNRTIs |
| Armodafinil (R-modafinil) | Psychostimulants |
| Ticagrelor | Anticoagulants and antiplatelets |
| Vicriviroc and ritonavir | Treatments of AIDS |
| Ritonavir | Protease inhibitors |
| Prednisone | Corticosteroids |
| Oxcarbazepine | Anticonvulsants |
| Danshen | Herbal medications |
| Clobazam | Benzodiazepines |
| Echinacea | Herbal medications |
| Ticlopidine | Anticoagulants and antiplatelets |
| Isavuconazole | Antifungals |
| Brivaracetam | Anticonvulsants |
| Stribild | Treatments of AIDS |
| Pioglitazone | Thiazolidinediones |
| VIEKIRA PAK | Antivirals |
| Dexamethasone | Corticosteroids |
| Terbinafine | Antifungals |
| Quercetin | Food products |
| Glycyrrhizin | Herbal medications |
| Aprepitant | Neurokinin-1 receptor antagonists |
| Pretomanib (PA-824) | Antibiotics |
| Safinamide | MAO-B inhibitors |
| Oritavancin | Antibiotics |
| Methylprednisolone | Corticosteroids |
| Topiramate | Anticonvulsants |

In some embodiments, the strong CYP3A4 inducer is rifampin. In some embodiments, the moderate CYP3A4 inducer is efavirenz. In some embodiments, the mild CYP3A4 inducer is dexamethasone. In some embodiments, the CYP3A4 inducer is rifampin or efavirenz.

Pemigatinib as described herein can inhibit the activity of the FGFR enzyme. For example, pemigatinib can be used to inhibit activity of an FGFR enzyme in a cell or in an individual or patient in need of inhibition of the enzyme by administering an inhibiting amount of pemigatinib to the cell, individual, or patient.

As an FGFR inhibitor, pemigatinib is useful in the treatment of various diseases associated with abnormal expression or activity of the FGFR enzyme or FGFR ligands.

Compounds which inhibit FGFR will be useful in providing a means of preventing the growth or inducing apoptosis in tumors, particularly by inhibiting angiogenesis. It is therefore anticipated that pemigatinib will prove useful in treating or preventing proliferative disorders such as cancers. In particular tumors with activating mutants of receptor tyrosine kinases or upregulation of receptor tyrosine kinases may be particularly sensitive to the inhibitors.

In certain embodiments, the disclosure provides a method for treating a FGFR-mediated disorder in a patient in need thereof, comprising the step of administering to said patient pemigatinib, or a pharmaceutically acceptable composition thereof.

For example, pemigatinib is useful in the treatment of cancer. Example cancers include bladder cancer, breast cancer (e.g., hormone R positive, triple negative), cervical cancer, colorectal cancer, cancer of the small intestine, colon cancer, rectal cancer, cancer of the anus, endometrial cancer, gastric cancer (e.g., gastrointestinal stromal tumors), head and neck cancer (e.g., cancers of the larynx, hypopharynx, nasopharynx, oropharynx, lips, and mouth, squamous head and neck cancers), kidney cancer (e.g., renal cell carcinoma, urothelial carcinoma, sarcoma, Wilms tumor), liver cancer (e.g., hepatocellular carcinoma, cholangiocellular carcinoma, liver angiosarcoma, hepatoblastoma), lung cancer (e.g., adenocarcinoma, small cell lung cancer and non-small cell lung carcinomas, parvicellular and non-parvicellular carcinoma, bronchial carcinoma, bronchial adenoma, pleuropulmonary blastoma), ovarian cancer, prostate cancer, testicular cancer, uterine cancer, vulvar cancer, esophageal cancer, gall bladder cancer, pancreatic cancer (e.g. exocrine pancreatic carcinoma), stomach cancer, thyroid cancer, parathyroid cancer, neuroendocrine cancer (e.g., pheochromocytoma, Merkel cell cancer, neuroendocrine carcinoma), skin cancer (e.g., squamous cell carcinoma, Kaposi sarcoma, Merkel cell skin cancer), and brain cancer (e.g., astrocytoma, medulloblastoma, ependymoma, neuro-ectodermal tumors, pineal tumors).

Further example cancers include hematopoietic malignancies such as leukemia or lymphoma, multiple myeloma, chronic lymphocytic lymphoma, adult T cell leukemia, B-cell lymphoma, cutaneous T-cell lymphoma, acute myelogenous leukemia, Hodgkin's or non-Hodgkin's lymphoma, myeloproliferative neoplasms (e.g., 8p11 myeloproliferative syndrome, polycythemia vera, essential thrombocythemia, and primary myelofibrosis), myelodysplastic syndrome, chronic eosinophilic leukemia, Waldenstrom's Macroglubulinemia, hairy cell lymphoma, chronic myelogenic lymphoma, acute lymphoblastic lymphoma, AIDS-related lymphomas, and Burkitt's lymphoma.

In certain embodiments, provided herein is a method of treating myeloid/lymphoid neoplasms in a patient in need thereof. In certain embodiments, the myeloid/lymphoid neoplasms are 8p11 myeloproliferative syndrome. As used herein, the term "8p11 myeloproliferative syndrome" (EMS) is meant to refer to myeloid/lymphoid neoplasms associated with eosinophilia and abnormalities of FGFR1 or myeloid/lymphoid neoplasms (MLN) with FGFR1 rearrangement. Eight P eleven myeloproliferative syndrome is reviewed in Jackson, Courtney C., et. al. *Human Pathology*, 2010, 41, 461-476. In certain embodiments, the myeloid/lymphoid neoplasm exhibits an 8p11 translocation. In certain embodiments, the 8p11 translocation is associated with activation of FGFR1. In certain embodiments, the patient has failed at least one previous treatment for myeloid/lymphoid neoplasms (e.g., 8p11 myeloproliferative syndrome). In some embodiments, the previous treatment is surgery or radiation therapy. In some embodiments, the patient has a history of hepatitis. In some embodiments, the hepatitis is chronic hepatitis B or hepatitis C. In some embodiments, the patient does not have a history of hepatitis.

In certain embodiments, provided herein is a method of treating cancer comprising administering to a patient in need thereof a therapeutically effect amount of pemigatinib. In certain embodiments, the cancer is selected from bladder cancer, breast cancer, cervical cancer, cancer of the small intestine, colorectal cancer, endometrial cancer, gastric cancer, head and neck cancer, kidney cancer, liver cancer, lung cancer, ovarian cancer, prostate cancer, testicular cancer, uterine cancer, vulvar cancer, esophageal cancer, gall bladder cancer, pancreatic cancer, thyroid cancer, skin cancer, brain cancer, leukemia, multiple myeloma, chronic lymphocytic lymphoma, adult T cell leukemia, B-cell lymphoma, acute myelogenous leukemia, Hodgkin's or non-Hodgkin's lymphoma, Waldenstrom's Macroglubulinemia, myeloproliferative neoplasms, chronic myelogenic lymphoma, acute lymphoblastic lymphoma, hairy cell lymphoma, Burkett's lymphoma, glioblastoma, melanoma, rhabdosarcoma, lymphosarcoma, and osteosarcoma.

In certain embodiments, the cancer is bladder cancer (e.g., urothelial carcinoma, squamous cell carcinoma, adenocarcinoma).

In certain embodiments, the liver cancer is cholangiocellular carcinoma (e.g., intrahepatic, hilar or perihilar, distal extrahepatic). As used herein, cholangiocellular carcinoma is the same as cholangiocarcinoma or bile duct cancer. In certain embodiments, the cholangiocarcinoma is advanced or metastatic cholangiocarcinoma. In certain embodiments, the cholangiocarcinoma is surgically unresectable. In certain embodiments, the cholangiocarcinoma is intrahepatic. In certain embodiments, the cholangiocarcinoma is extrahepatic. In certain embodiments, the cholangiocarcinoma exhibits FGFR2 tyrosine kinase fusions which define a unique molecular subtype as described in Arai, Yasuhito, et. al. *Hepatology*, 2014, 59, 1427-1434. In some embodiments, the cholangiocarcinoma is characterized by FGF/FGFR genetically altered tumors. In some embodiments, the tumors exhibit FGFR2 fusions. The FGFR2 fusion can be a translocation, interstitial deletion, or a chromosomal inversion. In some embodiments, the FGFR2 fusion is an FGFR2 translocation. The FGFR2 translocations can be selected from a group including, but not limited to, FGFR2-BICC1, FGFR2-AHCYL1, FGFR2-MACF1, FGFR2 intron 17 rearrangement. In some embodiments, the tumor exhibits FGF/FGFR alterations other than FGFR2 translocations. In some embodiments, the cholangiocarcinoma does not exhibit FGF/FGFR genetically altered tumors.

Other cancers treatable with the methods provided herein include tumors of the eye, glioblastoma, melanoma, rhabdosarcoma, lymphosarcoma, leiomyosarcoma, urothelial carcinoma (e.g., ureter, urethra, bladder, urachus), and osteosarcoma.

Pemigatinib can also be useful in the inhibition of tumor metastases.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease. In some embodiments, the term "treating" or "treatment" refers to inhibiting or ameliorating the disease.

As used herein, the term "coadministering" or "concomitant administering" refers to administering pemigatinib and one or more additional drugs (e.g., a CYP3A4 perpetrator) at or almost at the same time. For example, pemigatinib may be administered, e.g., on the same day, within a week, or within a month as the one or more additional drugs. In some embodiments, the one or more additional drugs is administered between administrations of pemigatinib.

As used herein, the term "therapy" refers to administration of a compound that is suitable for treating cancer. For example, therapy can refer to the administration of pemigatinib for treating cancer.

As used herein, the term "perpetrator" refers to a drug or compound that causes an effect on the substrate drug by inhibiting or inducing enzymes or transporters (e.g., CYP3A4). In some embodiments, the substrate drug is pemigatinib. A perpetrator can refer to, e.g., a CYP3A4 inhibitor or a CYP3A4 inducer.

As used herein, the term "$C_{max}$" refers to the maximum (or peak) serum concentration that a drug (e.g., pemigatinib) achieves in a specified compartment or test area of the body after the drug has been administered and before the administration of a second dose.

As used herein, the term "AUC" refers to the definite integral in a plot of drug (e.g., pemigatinib) concentration in blood plasma vs. time. The term "$AUC_{0-\infty}$" refers to the area under the concentration vs. time curve extrapolated to infinity. The term "$AUC_{0-t}$" refers to the area under the concentration vs. time curve up to the last measurable concentration.

As used herein, the term "$t_{1/2}$" refers to the time it takes for the serum concentration of a drug (e.g., pemigatinib) to fall to half of its original value. In other words, $t_{1/2}$ refers to the biological half-life of a drug (e.g., pemigatinib).

As used herein, and unless otherwise specified, the term "about", when used in connection with a numeric value or range of values, indicate that the value or range of values may deviate to an extent deemed reasonable by one of ordinary skill in the art. Specifically, the term "about", when used in this context, indicates that the numeric value or range of values may vary by 5%, 4%, 3%, 2%, 1%, 0.9%, 0.8%, 0.7%, 0.6%, 0.5%, 0.4%, 0.3%, 0.2% or 0.1% of the recited value or range of values.

As used herein, and unless otherwise specified, the term "substantial" or "substantially the same," when used in connection with a numeric value or range of values, indicate that the value or range of values may deviate to an extended deemed reasonable by one of ordinary skill in the art. Specifically, the term "substantially the same," when used in this context, indicates that the numeric value or range of values may vary by 20%, 10%, 15%, 5%, or 1% of the recited value or range of values. In some embodiments, the phrase "substantially the same" indicates that the numeric value or range of values may vary by 10%.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the FGFR enzyme with pemigatinib includes the administration of a compound described herein to an individual or patient, such as a human, having FGFR, as well as, for example, introducing pemigatinib into a sample containing a cellular or purified preparation containing the FGFR enzyme.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, immunogenicity or other problem or complication, commensurate with a reasonable benefit/risk ratio.

As used herein, the phrase "pharmaceutically acceptable carrier or excipient" refers to a pharmaceutically-acceptable material, composition, or vehicle, such as a liquid or solid filler, diluent, solvent, or encapsulating material. Excipients or carriers are generally safe, non-toxic and neither biologically nor otherwise undesirable and include excipients or carriers that are acceptable for veterinary use as well as human pharmaceutical use. In one embodiment, each component is "pharmaceutically acceptable" as defined herein. See, e.g., *Remington: The Science and Practice of Pharmacy,* 21st ed.; Lippincott Williams & Wilkins: Philadelphia, Pa., 2005; *Handbook of Pharmaceutical Excipients,* 6th ed.; Rowe et al., Eds.; The Pharmaceutical Press and the American Pharmaceutical Association: 2009; *Handbook of Pharmaceutical Additives,* 3rd ed.; Ash and Ash Eds.; Gower Publishing Company: 2007; *Pharmaceutical Preformulation and Formulation, 2nd ed.*; Gibson Ed.; CRC Press LLC: Boca Raton, Fla., 2009.

In some embodiments, a pharmaceutically acceptable salt of pemigatinib is used in the methods and combination therapies described herein. Salt forms of pemigatinib are described in U.S. Provisional Application No. 62/667,040.

Solid forms (e.g., crystalline forms) of pemigatinib can also be used in the methods and combination therapies described herein. Solid forms of pemigatinib, and methods of preparing solid forms of pemigatinib, are described in U.S. Provisional Application No. 62/667,166.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

Combination Therapy

One or more additional pharmaceutical agents or treatment methods such as, for example, anti-viral agents, chemotherapeutics or other anti-cancer agents, immune enhancers, immunosuppressants, radiation, anti-tumor and antiviral vaccines, cytokine therapy (e.g., IL2, GM-CSF, etc.), and/or tyrosine kinase inhibitors can be used in combination with pemigatinib for treatment of FGFR-associated diseases, disorders or conditions, or diseases or conditions as described herein. The agents can be combined with the present compounds in a single dosage form, or the agents can be administered simultaneously or sequentially as separate dosage forms.

Pemigatinib can be used in combination with one or more other kinase inhibitors for the treatment of diseases, such as cancer, that are impacted by multiple signaling pathways. For example, a combination can include one or more inhibitors of the following kinases for the treatment of cancer: Akt1, Akt2, Akt3, TGF-βR, Pim, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, fit-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf Additionally, pemigatinib can be combined with inhibitors of kinases associated with the PIK3/Akt/mTOR signaling pathway, such as PI3K, Akt (including Akt1, Akt2 and Akt3) and mTOR kinases.

In some embodiments, pemigatinib can be used in combination with one or more inhibitors of the enzyme or protein receptors such as HPK1, SBLB, TUT4, A2A/A2B, CD47, CDK2, STING, ALK2, LIN28, ADAR1, MAT2a, RIOK1, HDAC8, WDR5, SMARCA2, and DCLK1 for the treatment of diseases and disorders. Exemplary diseases and disorders include cancer, infection, inflammation and neurodegenerative disorders.

In some embodiments, pemigatinib can be used in combination with a therapeutic agent that targets an epigenetic regulator. Examples of epigenetic regulators include bromodomain inhibitors, the histone lysine methyltransferases, histone arginine methyl transferases, histone demethylases, histone deacetylases, histone acetylases, and DNA methyltransferases. Histone deacetylase inhibitors include, e.g., vorinostat.

For treating cancer and other proliferative diseases, pemigatinib can be used in combination with targeted therapies, including JAK kinase inhibitors (Ruxolitinib, additional JAK1/2 and JAK1-selective, baricitinib or INCB39110), Pim kinase inhibitors (e.g., INCB53914), PI3 kinase inhibitors including PI3K-delta selective and broad spectrum PI3K inhibitors (e.g., INCB50465 and INCB54707), PI3K-gamma inhibitors such as PI3K-gamma selective inhibitors, MEK inhibitors, CSF1R inhibitors, TAM receptor tyrosine kinases inhibitors (Tyro-3, Axl, and Mer; e.g., INCB81776), angiogenesis inhibitors, interleukin receptor inhibitors, Cyclin Dependent kinase inhibitors, BRAF inhibitors, mTOR inhibitors, proteasome inhibitors (Bortezomib, Carfilzomib), HDAC-inhibitors (panobinostat, vorinostat), DNA methyl transferase inhibitors, dexamethasone, bromo and extra terminal family members inhibitors (for example, bromodomain inhibitors or BET inhibitors, such as INCB54329 or INCB57643), LSD1 inhibitors (e.g., INCB59872 or INCB60003), arginase inhibitors (e.g., INCB1158), indoleamine 2,3-dioxygenase inhibitors (e.g., epacadostat, NLG919 or BMS-986205), and PARP inhibitors (e.g., olaparib or rucaparib).

For treating cancer and other proliferative diseases, pemigatinib can be used in combination with chemotherapeutic agents, agonists or antagonists of nuclear receptors, or other anti-proliferative agents. Pemigatinib can also be used in combination with a medical therapy such as surgery or radiotherapy, e.g., gamma-radiation, neutron beam radiotherapy, electron beam radiotherapy, proton therapy, brachytherapy, and systemic radioactive isotopes. Examples of suitable chemotherapeutic agents include any of: abarelix, aldesleukin, alemtuzumab, alitretinoin, allopurinol, altretamine, anastrozole, arsenic trioxide, asparaginase, azacitidine, baricitinib, bendamustine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, niraparib, nofetumomab, olaparib, oxaliplatin, paclitaxel, pamidronate, panobinostat, panitumumab, pegaspargase, pegfilgrastim, pemetrexed disodium, pentostatin, pipobroman, plicamycin, procarbazine, quinacrine, rasburicase, rituximab, rucaparib, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, veliparib, talazoparib and zoledronate.

In some embodiments, pemigatinib can be used in combination with immune checkpoint inhibitors. Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3 (e.g., INCAGN2385), TIM3 (e.g., INCB2390), VISTA, PD-1, PD-L1 and PD-L2. In some embodiments, the immune checkpoint molecule is a stimulatory checkpoint molecule selected from CD27, CD28, CD40, ICOS, OX40 (e.g., INCAGN1949), GITR (e.g., INCAGN1876) and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is a small molecule PD-L1 inhibitor. In some embodiments, the small molecule PD-L1 inhibitor has an IC50 less than 1 µM, less than 100 nM, less than 10 nM or less than 1 nM in a PD-L1 assay described in US Patent Publication Nos. US 20170107216, US 20170145025, US 20170174671, US 20170174679, US 20170320875, US 20170342060, US 20170362253, and US 20180016260, each of which is incorporated by reference in its entirety for all purposes.

In some embodiments, the inhibitor of an immune checkpoint molecule is an inhibitor of PD-1, e.g., an anti-PD-1 monoclonal antibody. In some embodiments, the anti-PD-1 monoclonal antibody is MGA012, nivolumab, pembrolizumab (also known as MK-3475), pidilizumab, SHR-1210, PDR001, ipilumimab or AMP-224. In some embodiments, the anti-PD-1 monoclonal antibody is nivolumab or pembrolizumab. In some embodiments, the anti-PD1 antibody is nivolumab. In some embodiments, the anti-PD1 antibody is pembrolizumab. In some embodiments, the anti-PD-1 monoclonal antibody is MGA012. In some embodiments, the anti-PD1 antibody is SHR-1210. Other anti-cancer agent(s) include antibody therapeutics such as 4-1BB (e.g. urelumab, utomilumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736. In some embodiments, the PD-L1 inhibitor is INCB086550.

In some embodiments, the inhibitor of an immune checkpoint molecule is an inhibitor of CTLA-4, e.g., an anti-CTLA-4 antibody. In some embodiments, the anti-CTLA-4 antibody is ipilimumab.

In some embodiments, the inhibitor of an immune checkpoint molecule is an inhibitor of LAG3, e.g., an anti-LAG3 antibody. In some embodiments, the anti-LAG3 antibody is BMS-986016 or LAG525.

In some embodiments, the inhibitor of an immune checkpoint molecule is an inhibitor of GITR, e.g., an anti-GITR antibody. In some embodiments, the anti-GITR antibody is TRX518 or MK-4166.

In some embodiments, the inhibitor of an immune checkpoint molecule is an inhibitor of OX40, e.g., an anti-OX40 antibody or OX40L fusion protein. In some embodiments, the anti-OX40 antibody is MEDI0562. In some embodiments, the OX40L fusion protein is MEDI6383.

In some embodiments, pemigatinib can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

Suitable antiviral agents contemplated for use in combination with pemigatinib can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

Suitable agents for use in combination with pemigatinib for the treatment of cancer include chemotherapeutic agents, targeted cancer therapies, immunotherapies or radiation therapy. Pemigatinib may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with pemigatinib. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

Pemigatinib may be combined with or in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with FGFR inhibitors. These include onartumzumab, tivantnib, and INC-280. Agents against Abl (or Bcr-Abl) include imatinib, dasatinib, nilotinib, and ponatinib and those against Alk (or EML4-ALK) include crizotinib.

Angiogenesis inhibitors may be efficacious in some tumors in combination with FGFR inhibitors. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with pemigatinib include inhibitors of the PI3K-AKT-mTOR pathway, inhibitors of the Raf-MAPK pathway, inhibitors of JAK-STAT pathway, and inhibitors of protein chaperones and cell cycle progression.

Agents against the PI3 kinase include but are not limited to topilaralisib, idelalisib, buparlisib. Inhibitors of mTOR such as rapamycin, sirolimus, temsirolimus, and everolimus may be combined with FGFR inhibitors. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, tofacitinib), Hsp90 (e.g., tanespimycin), cyclin dependent kinases (e.g., palbociclib), HDACs (e.g., panobinostat), PARP (e.g., olaparib), and proteasomes (e.g., bortezomib, carfilzomib) can also be combined with pemigatinib. In some embodiments, the JAK inhibitor is selective for JAK1 over JAK2 and JAK3.

Other suitable agents for use in combination with pemigatinib include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles (Abraxane®).

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with pemigatinib include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Pemigatinib may also be combined with immunotherapy drugs, including cytokines such as interferon alpha, interleukin 2, and tumor necrosis factor (TNF) in.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, *vinca* alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-α), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB, PD-L1 and PD-1 antibodies, or antibodies to cytokines (IL-10, TGF-β, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, pemigatinib as described herein can be administered in the form of pharmaceutical compositions which refers to a combination of pemigatinib as described herein, and at least one pharmaceutically acceptable carrier. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal, or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, pemigatinib in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the patient by employing procedures known in the art.

The compositions can be formulated in a unit dosage form, each dosage containing from about 4 to about 5 mg, or about 4.5 mg, of the active ingredient. In some embodiments, the unit dosage form contains about 9 mg of the active ingredient. In some embodiments, the unity dosage form contains about 13.5 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of pemigatinib. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present disclosure.

In some embodiments, pemigatinib is administered orally. In some embodiments, pemigatinib is administered once daily. In some embodiments, pemigatinib is administered in a daily dose of about 5 mg to about 20 mg. In some embodiments, pemigatinib is administered in a daily dose of about 10 mg to about 15 mg. In some embodiments, pemigatinib is administered in a daily dose of about 13.5 mg. In some embodiments, pemigatinib is administered as a tablet. In some embodiments, the tablet comprises about 0.5 mg to about 10 mg of pemigatinib. In some embodiments, the tablet comprises about 0.5 mg to about 5 mg pemigatinib. In some embodiments, the tablet comprises about 2 mg, about 4.5 mg, about 9 mg, about 13.5 mg, or about 18 mg of pemigatinib. In some embodiments, the tablet comprises about 0.5 mg of pemigatinib. In some embodiments, the tablet comprises about 2 mg of pemigatinib. In some embodiments, the tablet comprises about 4.5 mg of pemigatinib. In some embodiments, the tablet comprises about 9 mg of pemigatinib. In some embodiments, the tablet comprises about 13.5 mg of pemigatinib. In some embodiments, the tablet comprises about 18 mg of pemigatinib.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the pemigatinib, or compositions as described herein can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of pemigatinib can vary according to, for example, the particular use for which the treatment is made, the manner of administration of the compound, the health and condition of the patient, and the judgment of the prescribing physician. The proportion or concentration of pemigatinib in a pharmaceutical composition can vary depending upon a number of factors including dosage, chemical characteristics (e.g., hydrophobicity), and the route of administration. For example, pemigatinib can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Pemigatinib can also be formulated in combination with one or more additional active ingredients which can include any pharmaceutical agent such as anti-viral agents, vaccines, antibodies, immune enhancers, immune suppressants, anti-inflammatory agents and the like.

Kits

The present disclosure also includes pharmaceutical kits useful, e.g., in the treatment of cancer, which include one or more containers containing a pharmaceutical composition comprising a therapeutically effective amount of pemigatinib, or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. In some embodiments, the kit further comprises a CYP3A4 inhibitor. Instructions, either as inserts or as labels, indicating quantities of the components to be administered, guidelines for administration, and/or guidelines for mixing the components, can also be included in the kit.

EXAMPLES

Example 1. Synthesis of Pemigatinib

Step 1: 4-(ethylamino)-1H-pyrrolo[2,3-b]pyridine-5-carbaldehyde

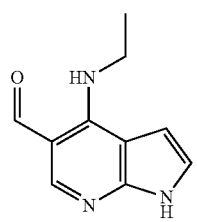

A mixture of 4-chloro-1H-pyrrolo[2,3-b]pyridine-5-carbaldehyde (CAS #958230-19-8, Lakestar Tech, Lot: 124-132-29: 3.0 g, 17 mmol) and ethylamine (10M in water, 8.3 mL, 83 mmol) in 2-methoxyethanol (20 mL, 200 mmol) was heated to 130° C. and stirred overnight. The mixture was cooled to room temperature then concentrated under reduced pressure. The residue was treated with 1N HCl (30 mL) and stirred at room temperature for 1 h then neutralized with saturated $NaHCO_3$ aqueous solution. The precipitate was collected via filtration then washed with water and dried to provide the desired product (2.9 g, 92%). LC-MS calculated for $C_{10}H_{12}N_3O$ $[M+H]^+$ m/z: 190.1; found: 190.1.

Step 2: 5-{[(2,6-difluoro-3,5-dimethoxyphenyl)amino]methyl}-N-ethyl-1H-pyrrolo[2,3-b]pyridin-4-amine

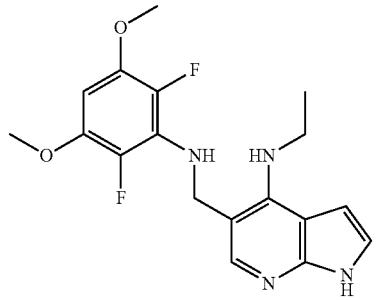 [SMILES: CCNc1c(CNc2c(F)c(OC)cc(OC)c2F)cnc2[nH]ccc12]

A mixture of 4-(ethylamino)-1H-pyrrolo[2,3-b]pyridine-5-carbaldehyde (7.0 g, 37 mmol), 2,6-difluoro-3,5-dimethoxyaniline (9.1 g, 48 mmol) and [(1S)-7,7-dimethyl-2-oxobicyclo[2.2.1]hept-1-yl]methanesulfonic acid (Aldrich, cat #21360: 2 g, 7 mmol) in xylenes (250 mL) was heated to reflux with azeotropic removal of water using Dean-Stark for 2 days at which time LC-MS showed the reaction was complete. The mixture was cooled to room temperature and the solvent was removed under reduced pressure. The residue was dissolved in tetrahydrofuran (500 mL) and then 2.0 M lithium tetrahydroaluminate in THF (37 mL, 74 mmol) was added slowly and the resulting mixture was stirred at 50° C. for 3 h then cooled to room temperature. The reaction was quenched by addition of water, 15% aqueous NaOH and water. The mixture was filtered and washed with THF. The filtrate was concentrated and the residue was washed with $CH_2Cl_2$ and then filtered to get the pure product (11 g, 82%). LC-MS calculated for $C_{18}H_{21}F_2N_4O_2[M+H]^+$ m/z: 363.2; found: 363.1.

Step 3: 3-(2,6-Difluoro-3,5-dimethoxyphenyl)-1-ethyl-1,3,4,7-tetrahydro-2H-pyrrolo[3',2':5,6]pyrido[4,3-d]pyrimidin-2-one

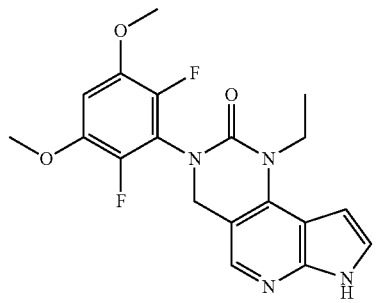 [SMILES: CCN1C(=O)N(c2c(F)c(OC)cc(OC)c2F)Cc2cnc3[nH]ccc3c21]

A solution of triphosgene (5.5 g, 18 mmol) in tetrahydrofuran (30 mL) was added slowly to a mixture of 5-{[(2,6-difluoro-3,5-dimethoxyphenyl)amino]methyl}-N-ethyl-1H-pyrrolo[2,3-b]pyridin-4-amine (5.6 g, 15 mmol) in tetrahydrofuran (100 mL) at 0° C. and then the mixture was stirred at room temperature for 6 h. The mixture was cooled to 0° C. and then 1.0 M sodium hydroxide in water (100 mL, 100 mmol) was added slowly. The reaction mixture was stirred at room temperature overnight and the formed precipitate was collected via filtration, washed with water, and then dried to provide the first batch of the purified desired product. The organic layer in the filtrate was separated and the aqueous layer was extracted with methylene chloride. The combined organic layer was concentrated and the residue was triturated with methylene chloride then filtered and dried to provide another batch of the product (total 5.5 g, 92%). LC-MS calculated for $C_{19}H_{19}F_2N_4O_3[M+H]^+$ m/z: 389.1; found: 389.1.

Step 4: 3-(2,6-difluoro-3,5-dimethoxyphenyl)-1-ethyl-7-(phenylsulfonyl)-1,3,4,7-tetrahydro-2H-pyrrolo[3',2':5,6]pyrido[4,3-d]pyrimidin-2-one

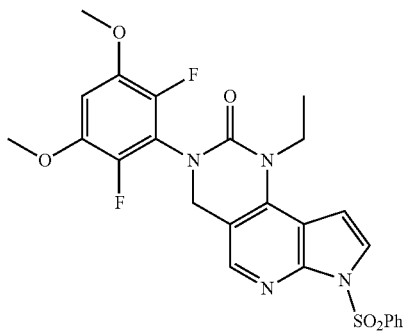

To a solution of 3-(2,6-difluoro-3,5-dimethoxyphenyl)-1-ethyl-1,3,4,7-tetrahydro-2H-pyrrolo[3',2':5,6]pyrido[4,3-d]pyrimidin-2-one (900 mg, 2.32 mmol) in N,N-dimethylformamide (20 mL) cooled to 0° C. was added sodium hydride (185 mg, 4.63 mmol, 60 wt % in mineral oil). The resulting mixture was stirred at 0° C. for 30 min then benzenesulfonyl chloride (0.444 mL, 3.48 mmol) was added. The reaction mixture was stirred at 0° C. for 1.5 h at which time LC-MS showed the reaction completed to the desired product. The reaction was quenched with saturated NH$_4$Cl solution and diluted with water. The white precipitate was collected via filtration then washed with water and hexanes, dried to afford the desired product (1.2 g, 98%) as a white solid which was used in the next step without further purification. LC-MS calculated for $C_{25}H_{23}F_2N_4O_5S$ $[M+H]^+$ m/z: 529.1; found: 529.1.

Step 5: 3-(2,6-difluoro-3,5-dimethoxyphenyl)-1-ethyl-2-oxo-7-(phenylsulfonyl)-2,3,4,7-tetrahydro-1H-pyrrolo[3',2':5,6]pyrido[4,3-d]pyrimidine-8-carbaldehyde

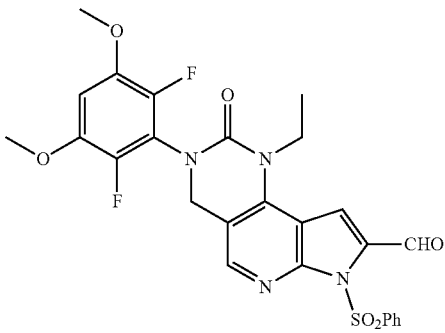

To a solution of 3-(2,6-difluoro-3,5-dimethoxyphenyl)-1-ethyl-7-(phenylsulfonyl)-1,3,4,7-tetrahydro2H-pyrrolo[3', 2': 5,6]pyrido[4,3-d]pyrimidin-2-one (1.75 g, 3.31 mmol) in tetrahydrofuran (80 mL) at −78° C. was added freshly prepared lithium diisopropylamide (1M in tetrahydrofuran (THF), 3.48 mL, 3.48 mmol). The resulting mixture was stirred at −78° C. for 30 min then N,N-dimethylformamide (1.4 mL, 18 mmol) was added slowly. The reaction mixture was stirred at −78° C. for 30 min then quenched with water and extracted with EtOAc. The organic extracts were combined then washed with water and brine. The organic layer was dried over Na$_2$SO$_4$ and concentrated. The residue was purified by flash chromatography eluted with 0 to 20% EtOAc in DCM to give the desired product as a white solid (1.68 g, 91%). LC-MS calculated for $C_{26}H_{23}F_2N_4O_6S$ $(M+H)^+$ m/z: 557.1; found: 556.9.

Step 6: 3-(2,6-difluoro-3,5-dimethoxyphenyl)-1-ethyl-8-(morpholin-4-ylmethyl)-7-(phenylsulfonyl)-1,3,4,7-tetrahydro-2H-pyrrolo[3',2':5,6]pyrido[4,3-d]pyrimidin-2-one

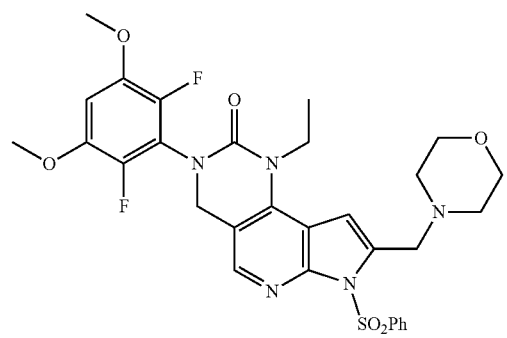

To a solution 3-(2,6-difluoro-3,5-dimethoxyphenyl)-1-ethyl-2-oxo-7-(phenylsulfonyl)-2,3,4,7-tetrahydro-1H-pyrrolo[3',2': 5,6]pyrido[4,3-d]pyrimidine-8-carbaldehyde (1.73 g, 3.11 mmol) in dichloromethane (50 mL) was added morpholine (0.95 mL, 11 mmol), followed by acetic acid (2 mL, 30 mmol). The resulting yellow solution was stirred at room temperature overnight then sodium triacetoxyborohydride (2.3 g, 11 mmol) was added. The mixture was stirred at room temperature for 3 h at which time LC-MS showed the reaction went to completion to the desired product. The reaction was quenched with saturated NaHCO$_3$ then extracted with ethyl acetate (EtOAc). The organic extracts were combined then washed with water and brine. The organic layer was dried over Na$_2$SO$_4$ and concentrated. The residue was purified by flash chromatography eluted with 0 to 40% EtOAc in DCM to give the desired product as a yellow solid (1.85 g, 95%). LC-MS calculated for C$_{30}$H$_{32}$F$_2$N$_5$O$_6$S (M+H)$^+$ m/z: 628.2; found: 628.0.

Step 7: 3-(2,6-difluoro-3,5-dimethoxyphenyl)-1-ethyl-8-(morpholin-4-ylmethyl)-1,3,4,7-tetrahydro-2H-pyrrolo[3',2': 5,6]pyrido[4,3-d]pyrimidin-2-one (pemigatinib)

To a solution of 3-(2,6-difluoro-3,5-dimethoxyphenyl)-1-ethyl-8-(morpholin-4-ylmethyl)-7-(phenylsulfonyl)-1,3,4,7-tetrahydro-2H-pyrrolo[3',2': 5,6]pyrido[4,3-d]pyrimidin-2-one (1.5 g, 2.4 mmol) in tetrahydrofuran (40 mL) was added tetra-n-butylammonium fluoride (1M in THF, 7.2 mL, 7.2 mmol). The resulting solution was stirred at 50° C. for 1.5 h then cooled to room temperature and quenched with water. The mixture was extracted with dichloromethane (DCM) and the organic extracts were combined then washed with water and brine. The organic layer was dried over Na$_2$SO$_4$ and concentrated. The residue was purified by flash chromatography eluted with 0 to 10% MeOH in DCM to give the desired product as a white solid, which was further purified by prep HPLC (pH=2, acetonitrile/H$_2$O). LC-MS calculated for C$_{24}$H$_{28}$F$_2$N$_5$O$_4$ (M+H)$^+$ m/z: 488.2; found: 488.0. $^1$H NMR (500 MHz, DMSO) δ 12.09 (s, 1H), 8.06 (s, 1H), 7.05 (t, J=8.1 Hz, 1H), 6.87 (s, 1H), 4.78 (s, 2H), 4.50 (s, 2H), 4.17 (q, J=6.8 Hz, 2H), 3.97 (br, 2H), 3.89 (s, 6H), 3.65 (br, 2H), 3.37 (br, 2H), 3.15 (br, 2H), 1.37 (t, J=6.8 Hz, 3H).

Example A. Study to Assess the Effect of Itraconazole and Rifampin on Pemigatinib Pharmacokinetics when Administered Orally in Healthy Patients This Example describes an ongoing Phase 1 clinical study to assess the effect of multiple doses of itraconazole, a potent CYP3A4 inhibitor, or rifampin, a potent CYP3A4 inducer, on the single-dose pharmacokinetics (e.g., C$_{max}$, AUC$_{0-t}$ and AUC$_{0-\infty}$) of pemigatinib.

In addition, this study also evaluates the safety and tolerability of pemigatinib when administered alone or in combination with itraconazole or rifampin. Safety and tolerability is assessed by monitoring adverse events, vital signs, physical examinations, 12-lead ECGs, and clinical laboratory blood and urine sample assessments. Pharmacokinetic endpoints include t$_{max}$, AUC$_{0-t}$, AUC$_{0-\infty}$, t$_{1/2}$, CL/F, and V$_z$/F.

The study is an open-label, fixed sequence, drug-drug interaction (DDI) study to assess the effect of multiple doses of itraconazole or rifampin on the single-dose PK of pemigatinib. Thirty-six healthy participants are divided into 2 cohorts of 18 participants. The study enrolls healthy adult participants aged 18 to 55 years.

In the first cohort, Cohort 1, participants receive each of the following treatments in succession:
Day 1: pemigatinib 4.5 mg (4.5 mg×1) single dose administered orally in the fasted state;
Days 4 through 7: Itraconazole 200 mg (100 mg×2) QD in the fed state (4 doses);
Day 8: pemigatinib 4.5 mg (4.5 mg x1) single dose and itraconazole 200 mg (100 mg×2) single dose in the fasted state; and
Day 9 through 11: Itraconazole 200 mg (100 mg×2) single dose in the fed state.

Vital signs (oral temperature; respiratory rate; automated, seated blood pressure; and pulse) are obtained at screening, check-in, and follow-up; at 0 hour (predose) on Days 1 and 8; and at approximately 1, 2, 3, 6, and 24 hours after the morning dose on Day 4 and Day 9. Clinical safety laboratory assessments are performed at screening; on Days −1, 2, 5, 9, 10, and 11; and at follow-up. A serum pregnancy is obtained at screening and follow-up. A urine pregnancy test is obtained at check-in for each visit for all women. On Day 8, a 12-lead ECG is performed predose, 2 hours postdose, and approximately 24 hours postdose. On other days, 12-lead ECGs are performed only at predose.

Pemigatinib is administered as follows: Participants enter the CRU on Day −1 and remain in the clinic until discharged on Day 12. They receive a single oral dose of pemigatinib 4.5 mg under fasted conditions on Day 1. On Days 4 through 7, they receive itraconazole 200 mg QD under fed conditions. On Day 8, participants receive single doses of pemigatinib 4.5 mg and itraconazole 200 mg under fasted conditions. On Days 9 through 11, participants will receive itraconazole 200 mg QD dose under fed conditions. Participants are discharged from the unit on Day 12.

In the second cohort, Cohort 2, participants receive each of the following treatments in succession:
Day 1: pemigatinib 13.5 mg (4.5 mg×3) single dose administered orally in the fasted state;
Days 4 through 10: Rifampin 600 mg (300 mg×2) QD in the fasted state (7 doses);
Day 11: pemigatinib 13.5 mg (4.5 mg×3) single dose and rifampin 600 mg (300 mg×2) single dose in the fasted state;
Day 12: Rifampin 600 mg (300 mg×2) QD in the fasted state.

Vital signs (oral temperature; respiratory rate; automated, seated blood pressure; and pulse) are obtained at screening, check-in and follow-up; at 0 hour (predose) on Days 1 and 11; and at approximately 1, 2, 3, 6, and 24 hours after the morning dose on Days 4, 10, and 12. Clinical safety laboratory assessments are performed at screening; on Days −1, 2, 8, and 13; and at follow-up. A serum pregnancy test is obtained at screening and follow-up. A urine pregnancy test is obtained at check-in for each visit for all women. On Day 11, a 12-lead ECG is performed predose, 2 hours postdose, and approximately 24 hours postdose. On other days, 12-lead ECGs is performed only at predose.

Pemigatinib is administered as follows: Participants enter the CRU on Day −1 and remain in the clinic until discharged on Day 13. They receive a single oral dose of pemigatinib 13.5 mg under fasted conditions on Day 1. On Days 4 through 10, they will receive rifampin 600 mg QD under fasted conditions. On Day 11, participants receive single doses of pemigatinib 13.5 mg and rifampin 600 mg under fasted conditions. On Day 12, participants receive rifampin 600 mg QD under fasted conditions. Participants are discharged from the unit on Day 12. Blood samples for PK analysis are collected at 0 hour (predose) and at 0.5, 1, 2, 3, 4, 6, 8, 12, and 16 hours postdose on Day 1; at 24 hours postdose on Day 2; at 48 hours postdose on Day 3; at 72 hours postdose on Day 4; at 0 hour (predose) and at 0.5, 1, 2, 3, 4, 6, 8, 12, and 16 hours postdose on Day 11; at 24 hours postdose on Day 12; and at 48 hours postdose on Day 13.

In both cohorts, each participant undergoes a screening period, a treatment period, and a post-treatment period. During the screening period (up to 28 days), participants sign an informed consent form and are assessed for eligibility. In the treatment period, PK blood samples are collected at scheduled times after each pemigatinib administration to determine plasma concentrations of pemigatinib. The post-treatment period will include a follow-up visit 30+3 days after the final dose of pemigatinib.

Screening lasts up to 28 days. The planned length of treatment is 12 days for Cohort 1 and 13 days for Cohort 2. Follow-up is 30+3 days after the last dose of the study drug. Total duration is up to 66+3 days for Cohort 1 and 69+3 days for Cohort 2.

The key inclusion criteria is male or female healthy adult participants aged 18 to 55 years, with a body mass index between 18 and 32 kg/m$^2$ inclusive. In addition, the participants should exhibit no clinically significant findings on screening evaluations (e.g., no current or recent history of a clinically significant bacterial, fungal, parasitic, mycobacterial, or viral infection, and not receiving systemic antibiotics). The participants must be willing to avoid pregnancy or fathering children.

The key exclusion criteria include the following:

History or clinical manifestations of significant metabolic, hepatic, renal (eGFR≤90 mL/min/1.73 m2), hematological, pulmonary, cardiovascular, GI, urological, neurological, or psychiatric disorders;

History of clinically significant corneal and retinal disorders;

History of a calcium/phosphate homeostasis disorder and/or extensive ectopic mineralization/calcification;

Serum calcium and phosphorus outside of the institutional normal range;

Current or recent history (<30 days before screening) of a clinically significant bacterial, fungal, parasitic, or mycobacterial infection, or currently receiving systemic antibiotics. Current clinically significant viral infection at screening or check-in;

Clinically meaningful findings on screening assessments (clinical, laboratory, and ECG);

Inability or unwillingness to comply with study procedures;

History of malignancy, with the exception of cured basal cell or squamous cell carcinoma of the skin;

History or presence of an abnormal ECG before dose administration that, in the investigator's opinion, is clinically significant (QTcF interval >450 milliseconds);

Resting pulse <45 bpm or >100 bpm, confirmed by repeat testing at screening;

History of unstable ischemic heart disease or uncontrolled hypertension (blood pressure >140/90 mm Hg at screening, confirmed by repeat testing);

History of stomach, cholecystectomy, or intestinal surgery, except that appendectomy will be allowed;

Presence of a malabsorption syndrome possibly affecting drug absorption (eg, Crohn's disease or chronic pancreatitis);

Use of any tobacco-containing or nicotine-containing products (including cigarette, pipe, cigar, chewing tobacco, nicotine patch, or nicotine gum) within 1-month of screening;

Hemoglobin, white blood cell, or platelet count below the lower reference limit of the testing laboratory at screening or check-in, confirmed by repeat testing. Absolute neutrophil count <laboratory lower limit of normal at screening or check-in, confirmed by repeat testing;

Hepatic transaminases (ALT and AST), alkaline phosphatase, or total bilirubin (except volunteers with Gilbert's disease, for which total bilirubin must be ≤2.0× ULN) >1.25 above the laboratory-defined ULN at screening or check-in, confirmed by repeat testing;

Evidence of hepatitis B virus or hepatitis C virus infection or risk of reactivation or HIV: positive result for hepatitis B surface antigen, hepatitis B core antibody, hepatitis C antibody, or positive HIV antibody screening tests;

Current treatment or treatment within 30 days or 5 half-lives (whichever is longer) before the first dose of study medication with another investigational medication or current enrollment in another investigational drug protocol;

Use of any medications (including prescription and over-the-counter) or nonprescription preparations (including vitamins, minerals, and phytotherapeutic/herbal/plant-derived preparations) within 7 days before study entry, unless deemed acceptable by the investigator;

Any condition that would, in the investigator's judgment, interfere with full participation in the study, including administration of study drug and attending required study visits, pose a significant risk to the participant, or interfere with interpretation of study data; and Known hypersensitivity or severe reaction to pemigatinib or excipients of pemigatinib.

In Cohort 1, pemigatinib is administered orally as a tablet with a unit dose strength of 4.5 mg and a dosage level of 4.5 mg. Itraconazole is administered orally as a capsule with a unit dose strength of 100 mg and a dosage level of 200 mg.

In Cohort 2, pemigatinib is administered orally as a tablet with a unit dosage strength of 4.5 mg and a dosage level of 13.5 mg. Rifampin is administered orally as a capsule with a unit dose strength of 300 mg and a dosage level of 600 mg.

Plasma concentrations of pemigatinib are quantified by LC-MS. Pemigatinib was assayed with a linear range of 1 nM to 1000 nM. PK parameters of pemigatinib are derived by non-compartmental analysis. The log-transformed PK parameters are compared by treatment using ANOVA. The geometric mean ratios and two-sided 90% confidence intervals of $C_{max}$, AUC0-t, and $AUC_{0-\infty}$ for pemigatinib are calculated by ANOVA.

Preliminary Results

Of the 36 volunteers enrolled (cohort 1, n=18; cohort 2, n=18), all completed the study. Demographics and baseline characteristics are shown below in Table 3.

TABLE 3

| Patient Demographics and Baseline Characteristics | | |
|---|---|---|
| | Clinical Trial (n = 36) | |
| Characteristic | Cohort 1 (n = 18) | Cohort 2 (n = 18) |
| Median (range) age, y | 34.5 (24-50) | 30 (19-49) |
| Women, n (%) | 8 (44) | 11 (61) |
| Race, n (%) | | |
| White | 15 (83) | 13 (72) |
| Black | 1 (6) | 4 (22) |
| Asian | 0 | 0 |
| American Indian/Alaska Native | 0 | 1 (6) |
| Other | 2 (11) | 0 |

TABLE 3-continued

Patient Demographics and Baseline Characteristics

| Characteristic | Clinical Trial (n = 36) | |
|---|---|---|
| | Cohort 1 (n = 18) | Cohort 2 (n = 18) |
| Mean (SD) weight, kg | 74.2 (11.2) | 73.5 (15.8) |
| Mean (SD) body mass index, kg/m² | 26.8 (3.1) | 26.4 (4.0) |

FIG. 1 shows the PK of pemigatinib in healthy volunteers after administration of pemigatinib with or without coadministration of itraconazole. Pemigatinib was absorbed quickly with or without itraconazole coadministration (median $T_{max}$=2.0 h in each case). Pemigatinib plasma concentrations subsequently declined in a biphasic manner. The estimated geometric mean $t_{1/2}$ was significantly shorter for pemigatinib alone versus pemigatinib coadministered with itraconazole (11.8 vs. 18.8 h, respectively; P<0.0001). The $C_{max}$ and $AUC_{0-\infty}$ of pemigatinib increased by 17% and 88%, respectively, upon coadministration with itraconazole; both increases were significant (P<0.0001).

Figure 2:
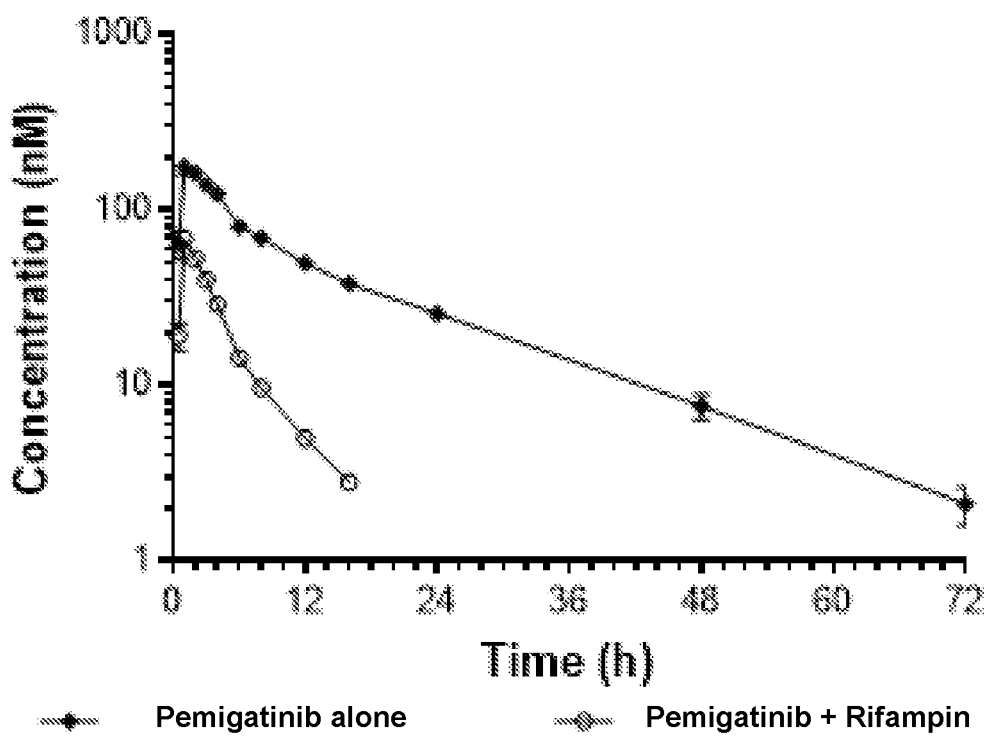
FIG. 2 shows the plasma concentration of pemigatinib in healthy volunteers after administration of pemigatinib with or without coadministration of rifampin.

FIG. 2 shows the PK of pemigatinib in healthy volunteers after administration of pemigatinib with or without coadministration of rifampin. Pemigatinib was absorbed quickly with or without rifampin coadministration (median $T_{max}$=1.5 h vs. 1.0 h for pemigatinib with vs. without rifampin coadministration, respectively). Pemigatinib plasma concentrations subsequently declined in a biphasic manner. The estimated geometric mean $t_{1/2}$ was significantly longer for pemigatinib alone versus pemigatinib coadministered with rifampin (12.7 vs. 4.7 h, respectively; P<0.0001). The $C_{max}$ and $AUC_0$, of pemigatinib decreased by 62% and 88%, respectively, upon coadministration with rifampin; both decreases were significant (P<0.0001).

Table 4 shows the PK parameters of Cohort 1 and Cohort 2.

Safety and Tolerability

Treatment-emergent adverse events (TEAEs) were reported n 7 (39%) volunteers in Cohort 1 and 6 (33%) volunteers in Cohort 2 with headache reported as the most common TEAE in both cohorts. There were no TEAEs of grade 3 or high, no treatment discontinuations or dose interruptions due to TEAEs, and no serious TEAEs or deaths.

A safety summary of the study is provided in Table 5.

TABLE 5

Safety Summary

| | TEAE, n (%) | |
|---|---|---|
| | Cohort 1 (n = 18) | Cohort 2 (n = 18) |
| Any TEAE | 7 (38.9) | 6 (33.3) |
| Headache | 3 (16.7) | 4 (22.2) |
| Nausea | 1 (5.6) | 3 (16.7) |
| Rash papular | 2 (11.1) | 1 (5.6) |
| Somnolence | 2 (11.1) | 1 (5.6) |
| Dry mouth | 2 (11.1) | 0 (0) |
| Dry skin | 2 (11.1) | 0 (0) |
| Paraesthesia | 0 (0) | 2 (11.1) |
| Vision blurred | 2 (11.1) | 0 (0) |

CONCLUSION

Coadministration of pemigatinib with itraconzole, a potent CYP3A4 inhibitor, resulted in a clinically significant increase in pemigatinib exposure. Coadministration of pemigatinib with rifampin, a potent CYP3A4 inducer, resulted in a clinically significant decrease in pemigatinib exposure. Based on these results, it is recommended that the dose of pemigatinib be reduced by approximately 50% when a

TABLE 4

PK parameters

| | $C_{max}$, nM | $T_{max}$, h | $t_{1/2}$, h | $AUC_{0-t}$, nM·h | $AUC_{0-\infty}$, nM·h | CL/F, L/h | Vz/F, L |
|---|---|---|---|---|---|---|---|
| Cohort 1 | | | | | | | |
| Pemigatinib alone (n = 18) | 60.1 ± 25.3 55.2 | 2.00 (1.00, 4.00) | 12.1 ± 2.74 11.8 | 674 ± 246 634 | 712 ± 252 672 | 14.5 ± 4.55 13.7 | 244 ± 75.8 233 |
| Pemigatinib + itraconazole (n = 18) | 68.2 ± 22.1 64.7 | 2.00 (1.00, 3.00) | 19.2 ± 4.30 18.8 | 1270 ± 381 1210 | 1320 ± 397 1270 | 7.63 ± 2.34 7.29 | 206 ± 63.2 198 |
| P value | 0.0098 | 0.262 | <0.0001 | <0.0001 | <0.0001 | <0.0001 | 0.0001 |
| Geometric mean ratio,* % (90% CI) | 117 (107-129) | — | — | 191 (177-206) | 188 (175-203) | — | — |
| Cohort 2 | | | | | | | |
| Pemigatinib alone (n = 18) | 187 ± 63.3 176 | 1.50 (0.50, 3.00) | 12.9 ± 2.90 12.7 | 1980 ± 526 1900 | 2040 ± 556 1960 | 14.8 ± 4.86 14.1 | 267 ± 73.1 258 |
| Pemigatinib + rifampin (n = 18) | 69.7 ± 20.0 66.9 | 1.00 (1.00, 3.00) | 5.05 ± 2.76 4.69 | 289 ± 74.9 280 | 301 ± 75.5 292 | 97.5 ± 23.8 94.7 | 673 ± 259 640 |
| P value | <0.0001 | 0.141 | <0.0001 | <0.0001 | <0.0001 | <0.0001 | <0.0001 |
| Geometric mean ratio,* % (90% CI) | 38.0 (33.2-43.5) | — | — | 14.7 (13.7-15.8) | 14.9 (13.9-16.1) | — | — |

Values are presented in the format of "Mean ± SD and Geometric Mean except that $T_{max}$ is reported as median (range)

strong CYP3A4 inhibitor is coadministered, and that coadministration of pemigatinib with a strong CYP3A4 inducer should be avoided.

Pemigatinib, when administered alone or in combination with itraconazole or rifampin, was safe and generally well tolerated in this group of healthy male and female volunteers.

Example B. In Vitro Metabolism of Pemigatinib by Individual Recombinant Human Cytochrome P450 Isozymes In vitro metabolism studies were conducted to determine the human cytochrome P450 (CYP) isozyme(s) capable of metabolizing pemigatinib. Experiments using individual recombinant human CYPs showed that pemigatinib was predominantly metabolized by CYP3A4. In agreement, experiments using human liver microsomes and selective chemical inhibitors of CYPs showed the metabolism of pemigatinib was only inhibited by ketoconazole, a potent CYP3A4 inhibitor. The in vitro metabolism of pemigatinib by CYP1A2, CYP2B6, CYP2C8, CYP2C9, CYP2C19, and CYP2D6 was negligible. Thus, it is concluded that pemigatinib is predominately metabolized by CYP3A4.

Pemigatinib was incubated with human liver microsomes in the absence and presence of selective chemical inhibitors of CYP1A2, CYP2B6, CYP2C8, CYP2C9, CYP2C19, CYP2D6, and CYP3A4. Pemigatinib (1 µM) was incubated (N=3) with human liver microsomes (1 mg/mL of protein), NADPH (2 mM), and 100 mM potassium phosphate buffer (pH 7.4) at 37° C. Parallel incubations using the same conditions included either furafylline (10 µM), ticlopidine (2 M), quercetin (10 µM), sulfaphenazole (10 µM), tranylcypromine (20 µM), quinidine (1 µM), or ketoconazole (1 µM) to selectively inhibit CYP1A2, CYP2B6, CYP2C8, CYP2C9, CYP2C19, CYP2D6, and CYP3A, respectively (Walsky and Obach 2004, Walsky et al 2006, Khojasteh et al 2011). Aliquots were taken at 0, 10, 20, and 30 minutes and denatured with methanol. After centrifugation to remove the denatured proteins, the resulting supernatants were analyzed by LC/MS.

To measure pemigatinib levels from in vitro incubations, samples were injected onto an Agilent Zorbax 5 µm SB-C18 column (2.1×50 mm) coupled to a ThermoFinnigan LCQ Fleet Ion-Trap mass spectrometer (Thermo-Fisher Scientific, Waltham, Mass.) operated in positive ionization mode. The mass spectrometer was coupled to a Shimadzu Sil HT-C combined autosampler/controller combined with a Shimadzu LC-10A binary gradient pump system (Shimadzu Scientific Instruments, Columbia, Md.). The chromatographic separation was achieved using a gradient elution consisting of mobile phase A: 5 mM ammonium formate in deionized water (Millipore Inc., Billerica, Mass.) that had been pH adjusted to pH 3.4 with formic acid (approximately 0.1%), and mobile phase B: 100% methanol (recombinant isozyme study) or 100% acetonitrile (chemical inhibitor study).

In vitro metabolism studies were conducted to determine the individual human recombinant CYP isozymes capable of metabolizing pemigatinib (1 µM) and included CYP1A2, CYP2B6, CYP2C8, CYP2C9, CYP2C19, CYP2D6, or CYP3A4. The percent of pemigatinib remaining after a 30-minute incubation with individual CYPs is shown in Table 6. Of the CYP isozymes evaluated, pemigatinib was metabolized to the greatest extent by CYP3A4. The metabolism of pemigatinib by CYP1A2, CYP2B6, CYP2C8, CYP2C9, CYP2C19, and CYP2D6, was negligible.

TABLE 6

The In Vitro Metabolism of Pemigatinib by Individual Human Recombinant CYP Isozymes

| CYP Isozyme | Average Percent (N = 2) of Pemigatinib Remaining vs Control (30 mins) |
|---|---|
| CYP1A2 | 92 |
| CYP2B6 | 96 |
| CYP2C8 | 94 |
| CYP2C9 | 88 |
| CYP2C19 | 95 |
| CYP2D6 | 94 |
| CYP3A4 | 14 |

To determine the relative contributions of CYP isozymes to the metabolism of pemigatinib in the liver, this compound was incubated in triplicate with human liver microsomes and selective chemical inhibitors of CYP1A2, CYP2B6, CYP2C8, CYP2C9, CYP2C19, CYP2D6, and CYP3A4.

When pemigatinib was incubated with human liver microsomes in the absence of chemical inhibitors, 72% of parent remained after 30 minutes, but when co-incubated with ketoconazole (2 M), a selective inhibitor of CYP3A4, the metabolism of pemigatinib was inhibited (97% of the parent compound remained). Other selective inhibitors had marginal effects on the metabolism of pemigatinib; therefore these data are supportive of the conclusion that pemigatinib is predominantly metabolized by CYP3A4.

TABLE 7

Effects of Chemical Inhibitors on the Matebolism of Pemigatinib in Human Liver Microsomes.

| Chemical Inhibitor | Concentration (µM) | Inhibitor of Isozyme | Mean Percent of Pemigatinib Remaining After 30-Minute Incubation (N = 3) |
|---|---|---|---|
| Pemigatinib (1 µM) | | No Inhibitor | 72 ± 1 |
| Furafylline | 10 | CYP1A2 | 67 ± 1 |
| Ticlopidine | 2 | CYP2B6 | 67 ± 3 |
| Quercetin | 10 | CYP2C8 | 77 ± 1 |
| Sulfaphenazole | 10 | CYP2C9 | 70 ± 3 |
| Tranylcypromine | 20 | CYP2C19 | 73 ± 2 |
| Quinidine | 1 | CYP2D6 | 71 ± 1 |
| Ketoconazole | 2 | CYP3A4 | 97 ± 2 |

Example C. Model Development for Pemigatinib and Evaluation of Drug-Drug Interactions A minimal physiologically based pharmacokinetic (PBPK) with advanced dissolution absorption and metabolism (ADAM) absorption model for pemigatinib that incorporates CYP3A4-mediated metabolism derived from in vitro data, mass balance data, and clinical PK data (Example A) was developed. Data from in vitro studies have indicated that CYP3A4 is the major isozyme responsible for the metabolism of pemigatinib (Example B). Based on mass balance and metabolite identification data, the oral absorption of pemigatinib is nearly complete and renal excretion is low (~1.0%), and liver metabolism is inferred to be the major clearance pathway for pemigatinib.

PBPK models that have been validated with clinical pharmacokinetic and DDI data can be used to predict other unknown DDI scenarios. The simulation results can also be used to support dose adjustment and label statements. The aims of this modeling and simulation study were to develop a PBPK model for pemigatinib, using in silico, in vitro, and clinical data to predict the drug-drug interaction.

Model Development

The initial PBPK model for pemigatinib was built using in vitro and in silico data. Data from in vitro studies (Example B) have indicated that CYP3A4 is the major isozyme responsible for the metabolism of pemigatinib. Based on mass balance and metabolite identification data, the oral absorption of pemigatinib is nearly complete (1.3% of the administered radioactive dose was recovered as unchanged pemigatinib in feces) and renal excretion is low (~1.0% of the dose is excreted in urine as unchanged pemigatinib), and liver metabolism is inferred to be the major clearance pathway for pemigatinib. Therefore, a minimal PBPK with ADAM absorption model for pemigatinib that incorporates CYP3A4-mediated metabolism derived from in vitro data and human ADME data was then further developed and model was used to describe the clinical PK data from pemigatinib alone cohorts in Example A. The sensitivity analysis of pemigatinib $f_{mCYP3\_A4}$ on drug interaction with itraconazole suggested that CYP3A4 contributes~55% of the metabolic clearance for pemigatinib. The verified pemigatinib model was then used to simulate the observed effect of itraconazole on pemigatib pharmacokinetics, and to confirm the contribution of CYP3A4 ($f_{mCYP3\_A4}$) to pemigatinib metabolic clearance. Finally, the pemigatinib PBPK model was applied to simulate the effect of other inhibitors and inducers on pemigatinib pharmacokinetics.

Simulations were performed using pemigatinib PBPK model and compared with the observations in the clinical studies available. The pemigatinib PBPK model was validated by simulation of DDIs between pemigatinib and itraconazole or rifampin using a Simcyp virtual population, with the study design matching the corresponding clinical DDI study in healthy volunteers. The itraconazole capsule (200 mg) was administered daily from Day 1 to Day 6 and a single 4.5-mg dose of pemigatinib tablet was administered orally with itraconazole on Day 5. The rifampin capsule (600 mg) was administered daily from Day 1 to Day 8 and a single 13.5-mg dose of pemigatinib tablet was administered orally with rifampin on Day 8. The simulations were performed using an age range of 18-55 years (proportion of female volunteers: 0.5).

The verified Pemigatinib PBPK model was used to predict the effect of other strong (clarithromycin), moderate (diltiazem, erythromycin, and cyclosporine), and mild (fluvoxamine) CYP3A4 inhibitors and moderate (efavirenz) and mild (dexamethasone) CYP3A4 inducers on pemigatinib PK. The Simcyp default PBPK models for clarithromycin, erythromycin, diltiazem, cyclosporine, fluvoxamine, and efavirenz were used in these simulations. Dexamethasone PBPK models are not available in the Simcyp model library. Therefore, a literature reported dexamethasone PBPK model was used for simulation. For CYP3A4-mediated inhibition/induction simulation, the inhibitors/inducers were administered daily from Day 1 to Day 12 and a single 13.5-mg dose of pemigatinib tablet was administered orally on Day 8. The simulations were performed using an age range of 18-55 years (proportion of female volunteers: 0.5).

Results

Figure 3A:
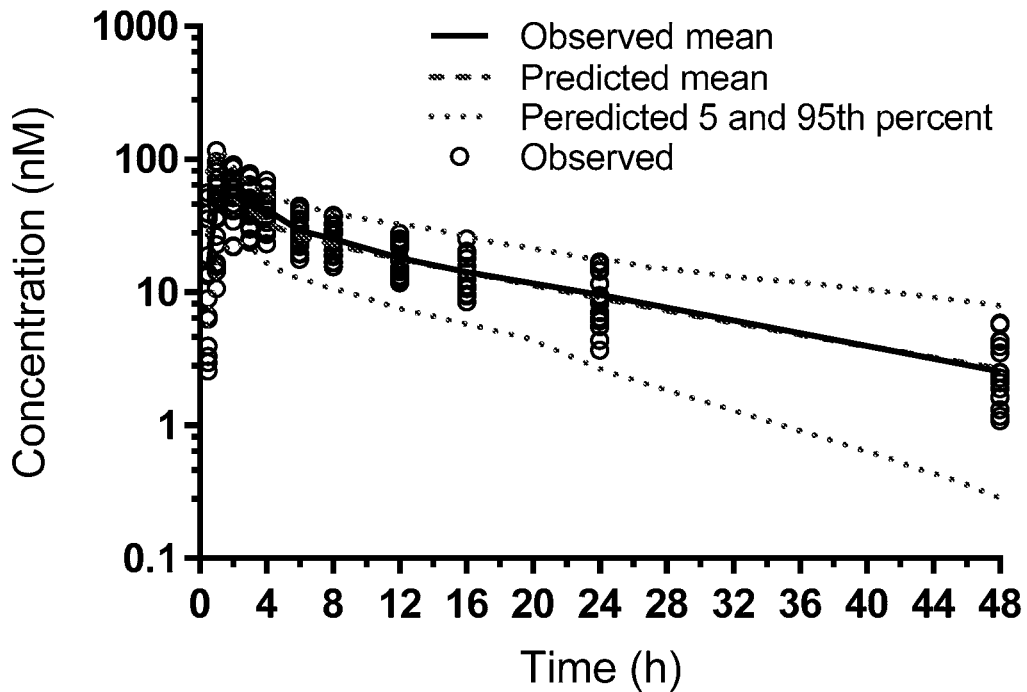
FIG. 3A shows the observed and simulated mean plasma concentration-time profiles for pemigatinib following a single oral dose of 4.5 mg pemigatinib tablet alone.
Figure 3B:
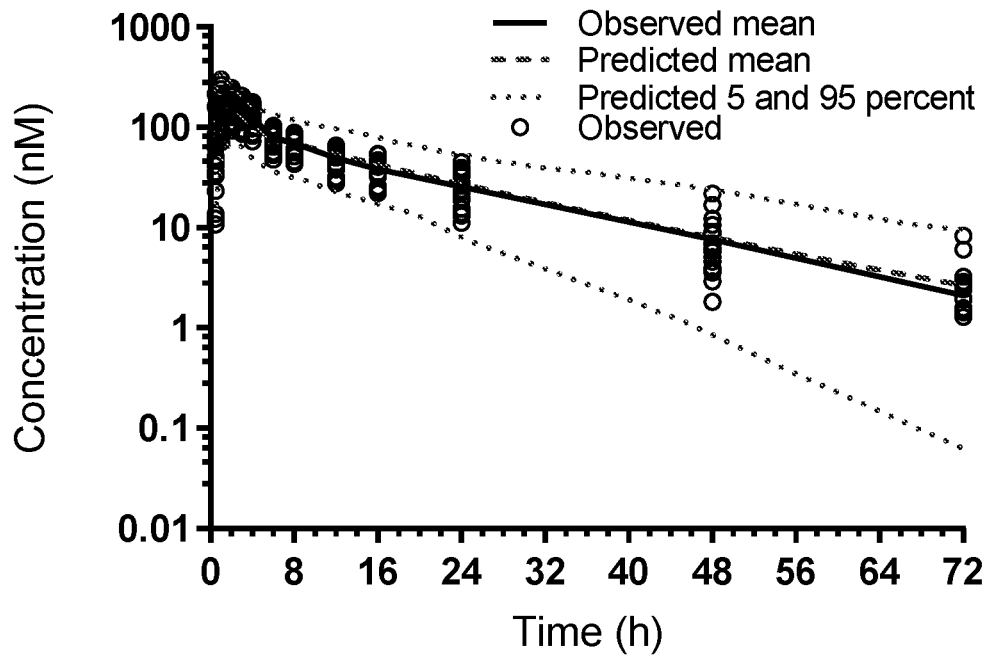
FIG. 3B shows the observed and simulated mean plasma concentration-time profiles for pemigatinib following a single oral dose of 13.5 mg pemigatinib tablet alone.
Figure 4A:
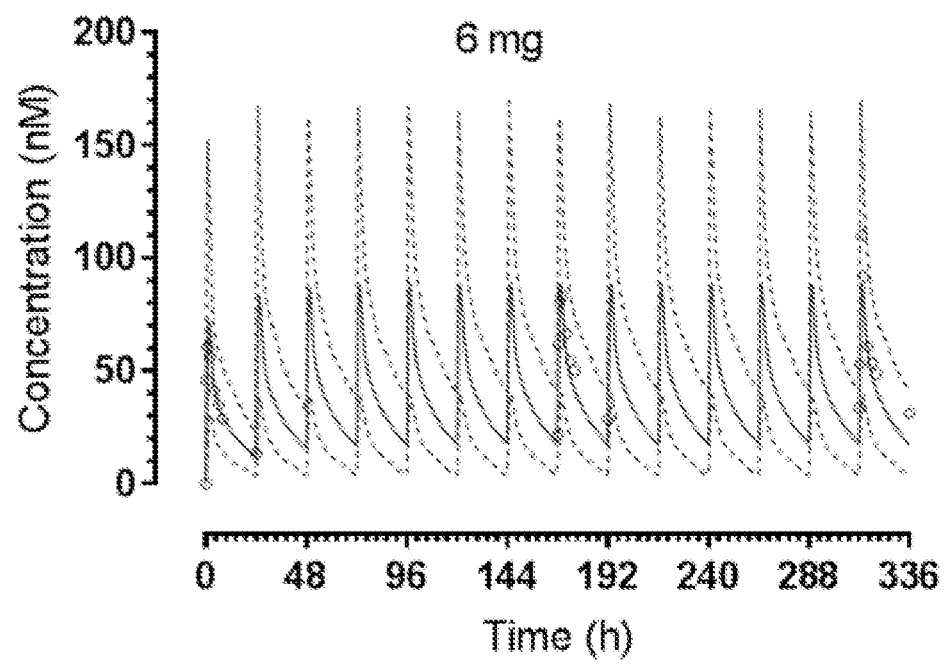
FIG. 4A shows the simulated and observed mean plasma concentration-time profiles of pemigatinib following a multiple oral dose of pemigatinib tablets at 6 mg in cancer patients. The solid line shows the simulated mean. The dashed line shows the simulated 5% and 95%. The circles show the observed data.
Figure 4B:
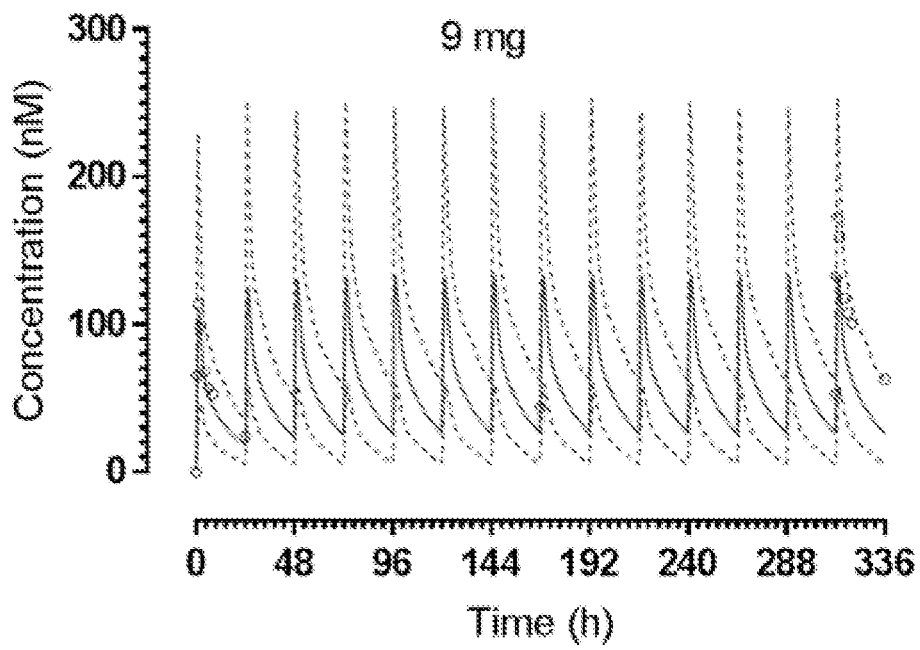
FIG. 4B shows the simulated and observed mean plasma concentration-time profiles of pemigatinib following a multiple oral dose of pemigatinib tablets at 9 mg in cancer patients. The solid line shows the simulated mean. The dashed line shows the simulated 5% and 95%. The circles show the observed data.
Figure 4C:
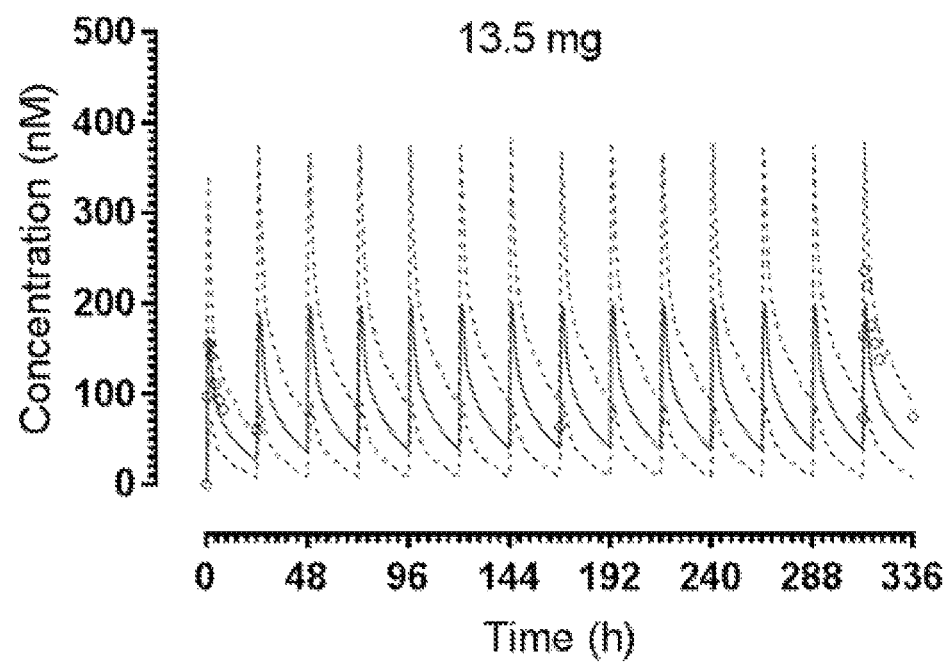
FIG. 4C shows the simulated and observed mean plasma concentration-time profiles of pemigatinib following a multiple oral dose of pemigatinib tablets at 13.5 mg in cancer patients. The solid line shows the simulated mean. The dashed line shows the simulated 5% and 95%. The circles show the observed data.
Figure 4D:
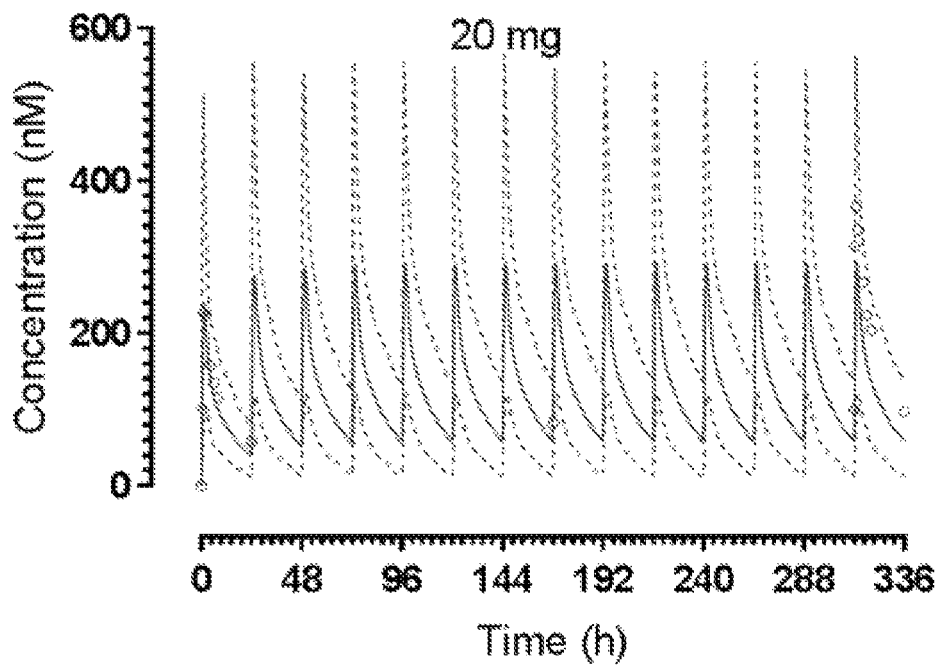
FIG. 4D shows the simulated and observed mean plasma concentration-time profiles of pemigatinib following a multiple oral dose of pemigatinib tablets at 20 mg in cancer patients. The solid line shows the simulated mean. The dashed line shows the simulated 5% and 95%. The circles show the observed data.
Figure 5A:
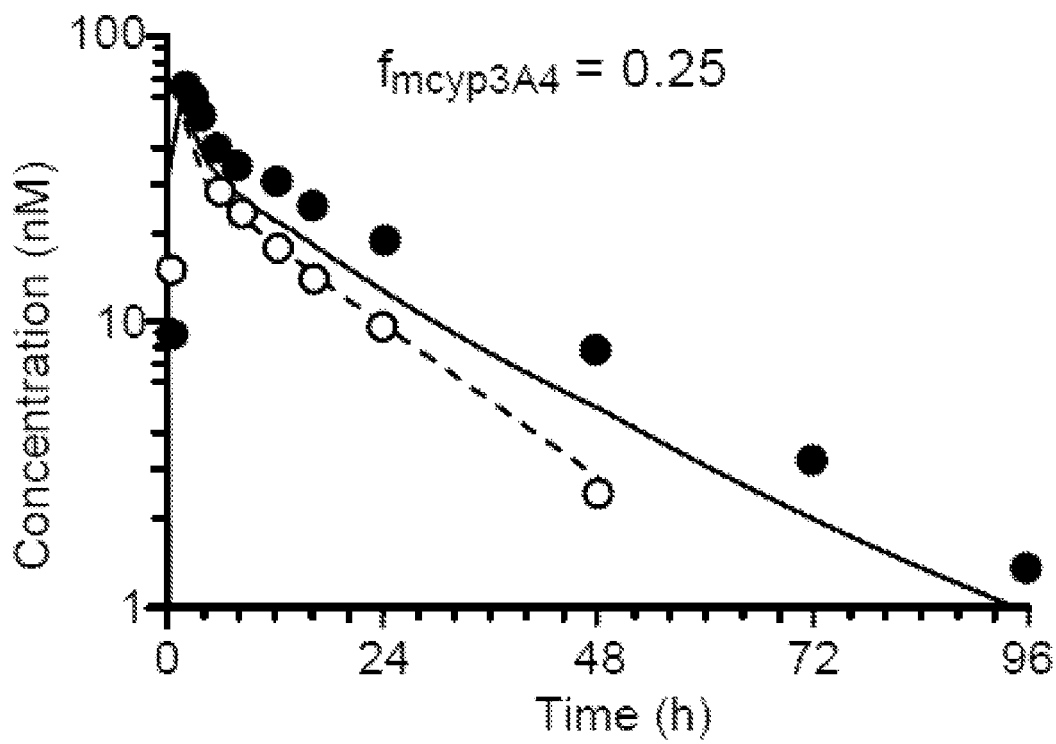
FIG. 5A shows the Sensitivity analysis of pemigatinib $f_{mCYP3\_A4}$ on drug interaction with itraconazole, at $f_{mCYP3\_A4}=0.25$. The dashed line shows the simulated mean for pemigatinib alone; the solid line shows the simulated mean for pemigatinib when co-administered with itraconazole; the open circle shows the observed mean for pemigatinib alone; the closed circle shows the observed mean for pemigatinib when co-administered with itraconazole.
Figure 5B:
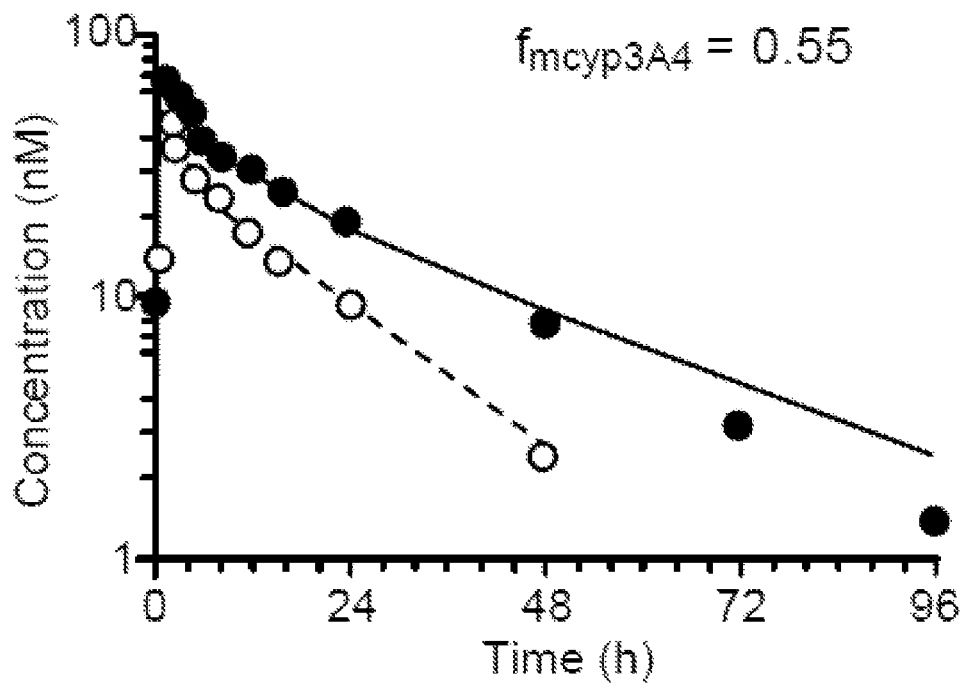
FIG. 5B shows the Sensitivity analysis of pemigatinib $f_{mCYP3\_A4}$ on drug interaction with itraconazole, at $f_{mCYP3\_A4}=0.55$. The dashed line shows the simulated mean for pemigatinib alone; the solid line shows the simulated mean for pemigatinib when co-administered with itraconazole; the open circle shows the observed mean for pemigatinib alone; the closed circle shows the observed mean for pemigatinib when co-administered with itraconazole.
Figure 5C:
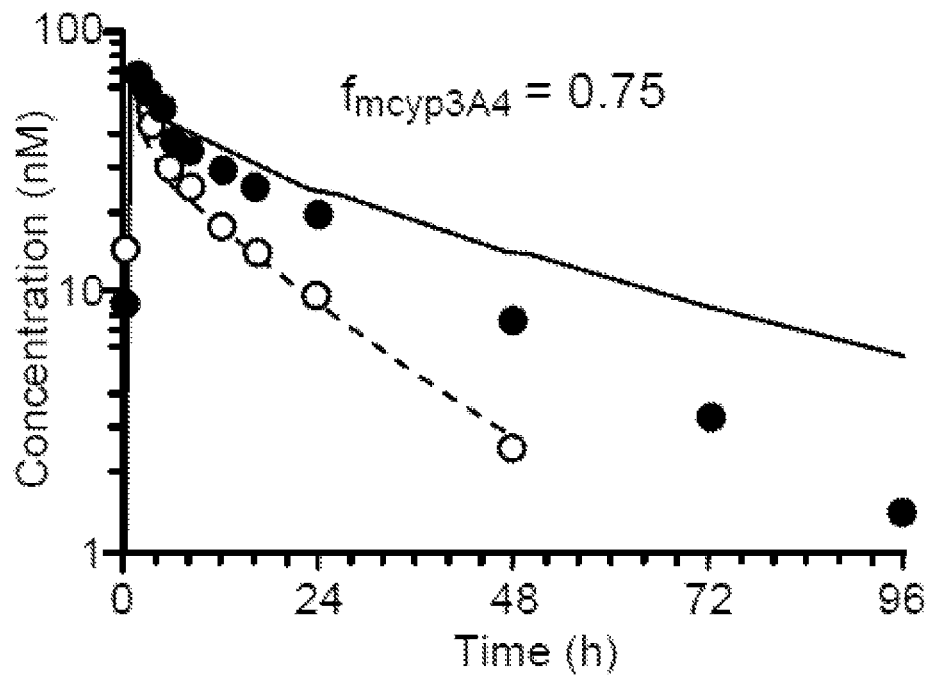
FIG. 5C shows the Sensitivity analysis of pemigatinib $f_{mCYP3\_A4}$ on drug interaction with itraconazole, at $f_{mCYP3\_A4}=0.75$. The dashed line shows the simulated mean for pemigatinib alone; the solid line shows the simulated mean for pemigatinib when co-administered with itraconazole; the open circle shows the observed mean for pemigatinib alone; the closed circle shows the observed mean for pemigatinib when co-administered with itraconazole.
Figure 5D:
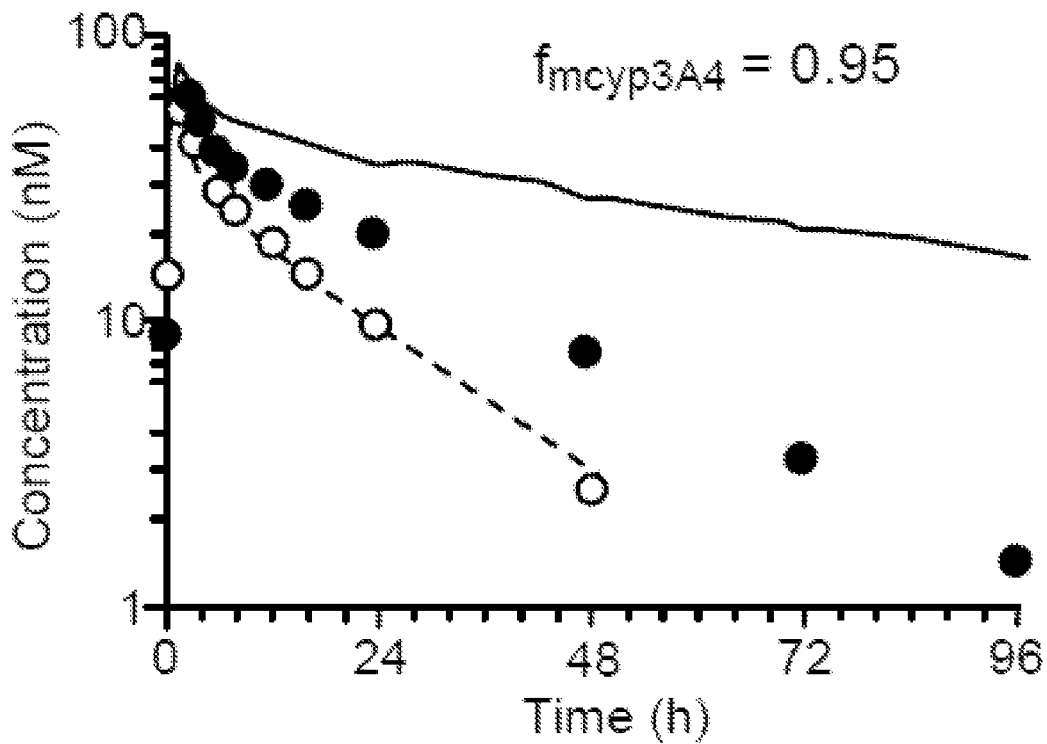
FIG. 5D shows the Sensitivity analysis of pemigatinib $f_{mCYP3\_A4}$ on drug interaction with itraconazole, at $f_{mCYP3\_A4}=0.95$. The dashed line shows the simulated mean for pemigatinib alone; the solid line shows the simulated mean for pemigatinib when co-administered with itraconazole; the open circle shows the observed mean for pemigatinib alone; the closed circle shows the observed mean for pemigatinib when co-administered with itraconazole.

A minimal PBPK with ADAM absorption model for pemigatinib that incorporates CYP3A4-mediated metabolism derived from in vitro data and in vivo clinical data was developed. FIG. 3 shows the observed and simulated mean plasma concentration-time profiles for pemigatinib following a single oral dose of 4.5 mg (FIG. 3A) and 13.5 (FIG. 3B) mg pemigatinib tablet alone. Predicted and observed geometric mean plasma $C_{max}$ and $AUC_{0-\infty}$ values for pemigatinib tablets are shown in Table 8. The simulated profiles of pemigatinib are comparable to the clinical data and the predicted geometric mean $C_{max}$ and $AUC_{0-\infty}$ values are within 0.93- to 1.11-fold of the observed data.

TABLE 8

Predicted and Observed Exposures (Geometric Mean) Following a Single Oral Dose of 4.5 mg or 13.5 mg Pemigatinib Tablets

| Dose | Predicted $C_{max}$ (nM) | Observed $C_{max}$ (nM) | Predicted AUC (h * nM) | Observed AUC (h * nM) | $C_{max}$ (pred/obs) | AUC (pred/obs) |
|---|---|---|---|---|---|---|
| 4.5 mg | 52.6 | 55.2 | 627 | 672 | 0.95 | 0.93 |
| 13.5 mg | 176 | 158 | 1878 | 1960 | 1.11 | 0.95 |

The pemigatinib PBPK model was developed from healthy volunteer was used to describe cancer patients PK data from phase I dose escalation and dose expansion study (6-20 mg). The model was used to predict pemigatinib plasma concentration-time curves in cancer patients after multiple oral dose of 6, 9, 13.5 and 20 mg pemigatinib because only one patient was dosed for 1, 2 and 4 mg, respectively. FIG. 4 shows the observed (circles) and simulated (lines) mean plasma concentration-time profiles for pemigatinib following a multiple oral dose administration. Predicted and observed geometric mean plasma $C_{max}$ and AUC values for pemigatinib tablets are shown in Table 9. The simulated PK profiles of pemigatinib are comparable to the clinical data and the predicted geometric mean $C_{max}$ and AUC values are within 0.676- to 1.18-fold of the observed data.

TABLE 9

Predicted and Observed Exposures (Geometric Mean) Following a Multiple Dose of Pemigatinib Tablets

| Dose | Predicted Cmax, ss (nM) | Observed Cmax, ss (nM) | Predicted AUCss (h * nM) | Observed AUCss (h * nM) | Cmax, ss (pred/obs) | AUCss (pred/obs) |
|---|---|---|---|---|---|---|
| 6 mg | 77.4 | 101 | 1002 | 1110 | 0.766 | 0.902 |
| 9 mg | 116 | 161 | 1259 | 1508 | 0.720 | 0.834 |
| 13.5 mg | 193 | 175 | 3073 | 2600 | 1.10 | 1.18 |
| 20 mg | 257 | 380 | 3345 | 4180 | 0.676 | 0.800 |

The sensitivity analysis of pemigatinib $f_{mCYP3\_A4}$ on drug interaction with itraconazole were used to determine CYP3A4 contribution of metabolic clearance for pemigatinib. The input of CYP3A4 $CL_{int}$ was varied to obtain a range of $f_{mCYP3A}$ from 0.25 to 0.95 (using the Simcyp retrograde calculator). The simulations of itraconazole-pemigatinib DDIs with different $f_{mCYP3A}$ values for pemigatinib were compared with the observed DDI data. When $f_{mCYP3\_A4}$ was assigned to be 55%, the best prediction was achieved by PBPK model for the effect of DDI between pemigatinib and itraconazole (FIG. 5 and Table 10).

TABLE 10

Simulated Pemigatinib Geometric Mean $C_{max}$ and AUC Ratios using PBPK Model with Various $f_{mCYP3A4}$ Values

| $f_{mCYP3A4}$ (%) | $C_{max}$ Ratio | | AUC Ratio | |
|---|---|---|---|---|
| | Predicted | Observed | Predicted | Observed |
| 25 | 1.09 | 1.17 | 1.31 | 1.88 |
| 55 | 1.22 | | 1.98 | |
| 75 | 1.32 | | 2.88 | |
| 95 | 1.44 | | 5.02 | |

Figure 6A:
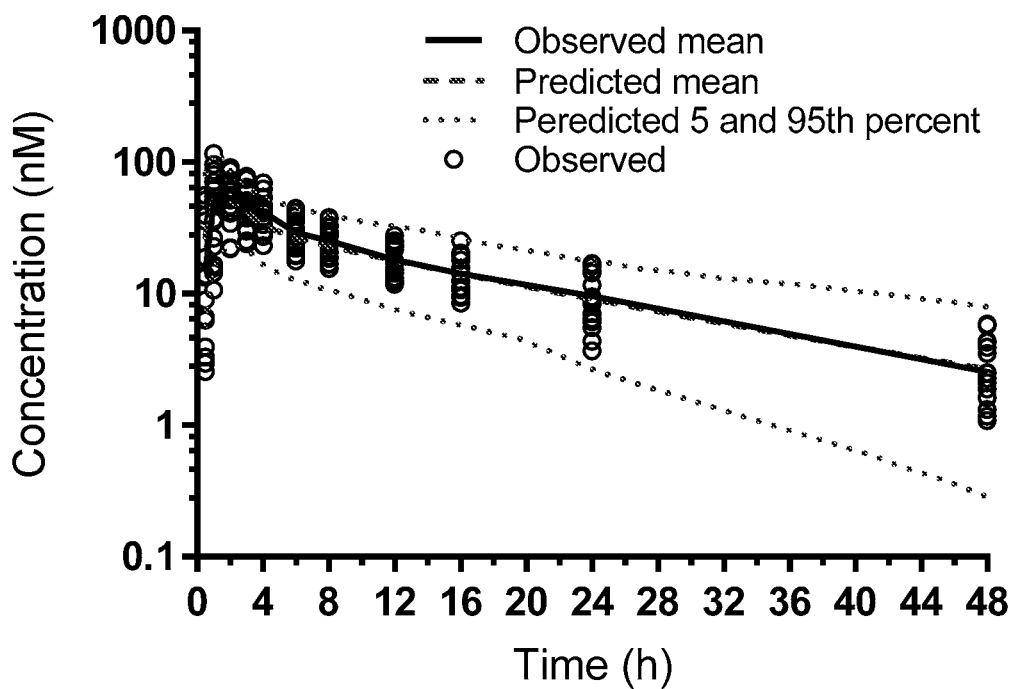
FIG. 6A shows the simulated and observed plasma concentration-time profiles of pemigatinib following a single oral dose of 4.5 mg pemigatinib tablets alone (without itraconazole administration).
Figure 6B:
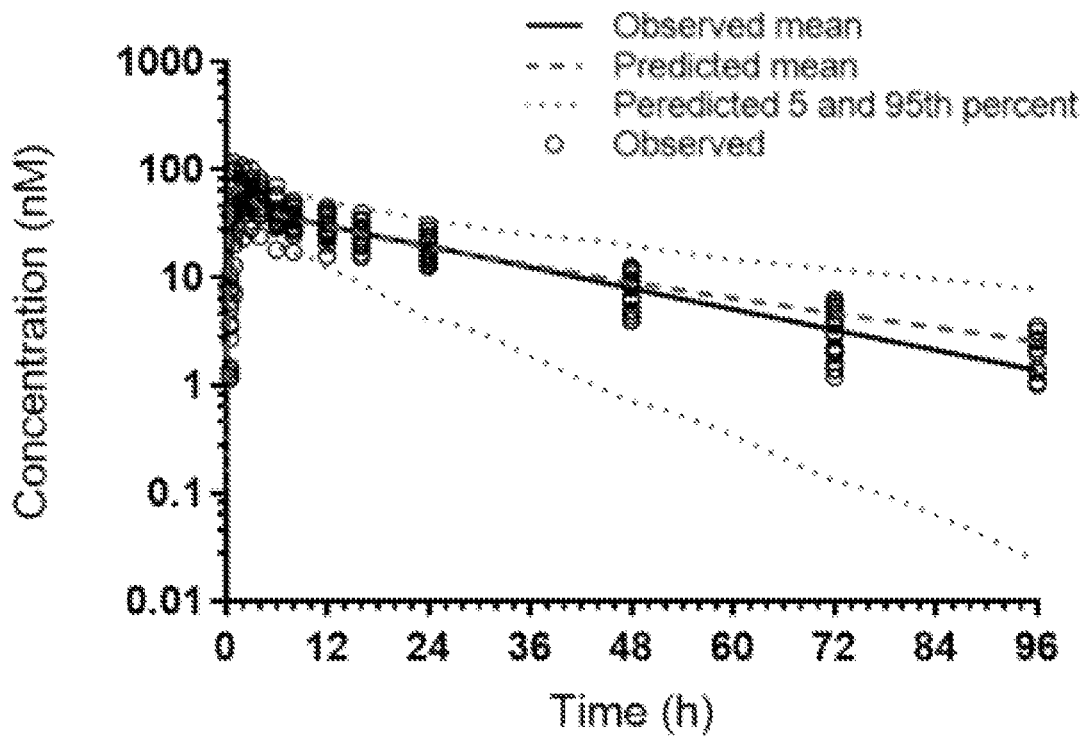
FIG. 6B shows the simulated and observed plasma concentration-time profiles of pemigatinib following a single oral dose of 4.5 mg pemigatinib tablets coadministered with itraconazole.
Figure 7A:
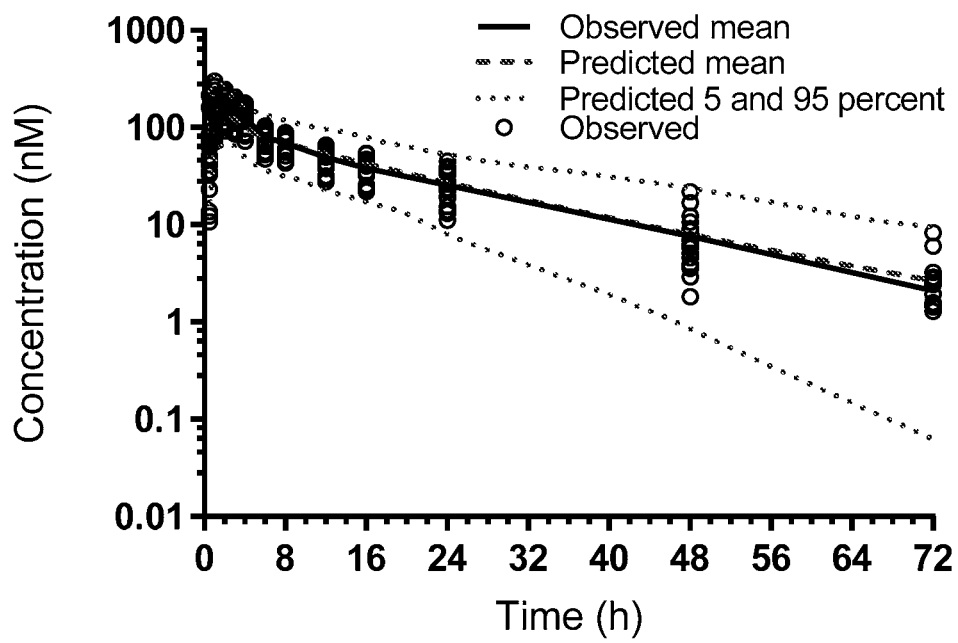
FIG. 7A shows the simulated and observed plasma concentration-time profiles of pemigatinib following a single oral dose of 13.5 mg pemigatinib tablets alone (without rifampin administration).
Figure 7B:
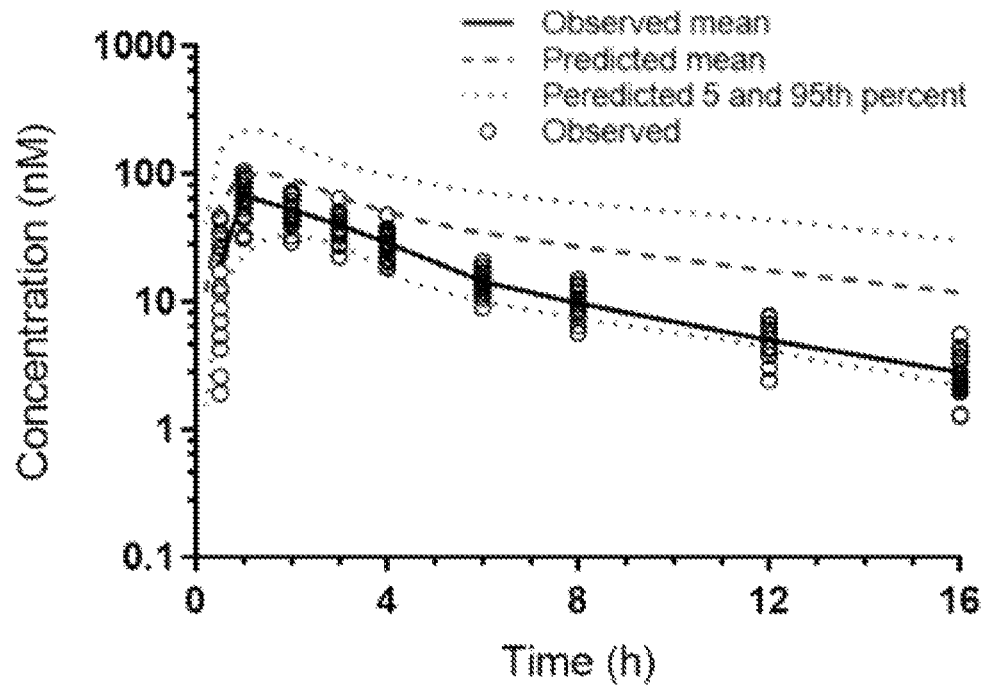
FIG. 7B shows the simulated and observed plasma concentration-time profiles of pemigatinib following a single oral dose of 13.5 mg pemigatinib tablets coadministered with rifampin.

The comparison between simulated and observed pemigatinib PK in the presence and absence of itraconazole or rifampin are presented in FIG. 6 and FIG. 7, respectively. The predicted and observed geometric mean plasma $C_{max}$ and AUC values for pemigatinib tablets are shown in Table 11.

TABLE 11

Predicted and Observed Pemigatinib $C_{max}$ and AUC Ratios Following a Single Oral Dose of Pemigatinib Tablets With and Without Itraconazole or Rifampin Administration

| CYP3A4 Perpetrator | $C_{max}$ Ratio | | AUC Ratio | |
|---|---|---|---|---|
| | Predicted | Observed | Predicted | Observed |
| Itraconazole | 1.22 (1.20, 1.24) | 1.17 (1.07, 1.29) | 1.98 (1.91, 2.05) | 1.88 (1.75, 2.03) |
| Rifampin | 0.604 (0.572, 0.638) | 0.380 (0.332, 0.425) | 0.323 (0.299, 0.349) | 0.149 (0.139, 0.161) |

Values are presented in the format of geometric mean (90% confidence intervals)

The model-predicted pemigatinib AUC ratio of 1.98 (90% CI:1.91, 2.05) and $C_{max}$ ratio of 1.22 (90% CI:1.20, 1.24) are similar to the observed AUC ratio of 1.88 (90% CI:1.75, 2.03) and $C_{max}$ ratio of 1.17 (90% CI:1.07, 1.29) for itraconazole DDI. The predicted geometric mean AUC ratios and $C_{max}$ ratios are within the 90% CI of the observed data.

However, underprediction is observed for rifampin DDI. Model-predicted pemigatinib AUC ratio of 0.323 (90% CI:0.299, 0.349) and $C_{max}$ ratio of 0.604 (90% CI:0.572, 0.638) are approximately 1.5 to 2-fold higher comparing to the observed AUC ratio of 0.149 (90% CI:0.139, 0.161) and $C_{max}$ ratio of 0.380 (90% CI:0.332, 0.425) for rifampin DDI. In Example A, the observation of an 85% reduction in AUC and 63% decrease in half-life of pemigatinib following rifampin coadministration. In addition, the first pass gut and liver metabolism is expected to be low due to high permeability and low oral clearance of pemigatinib. All of these suggest that a decrease in bioavailability of pemigatinib occurred with rifampin coadministration, in addition to an increase in systemic clearance (eg, reduced absorption).

Figure 8:
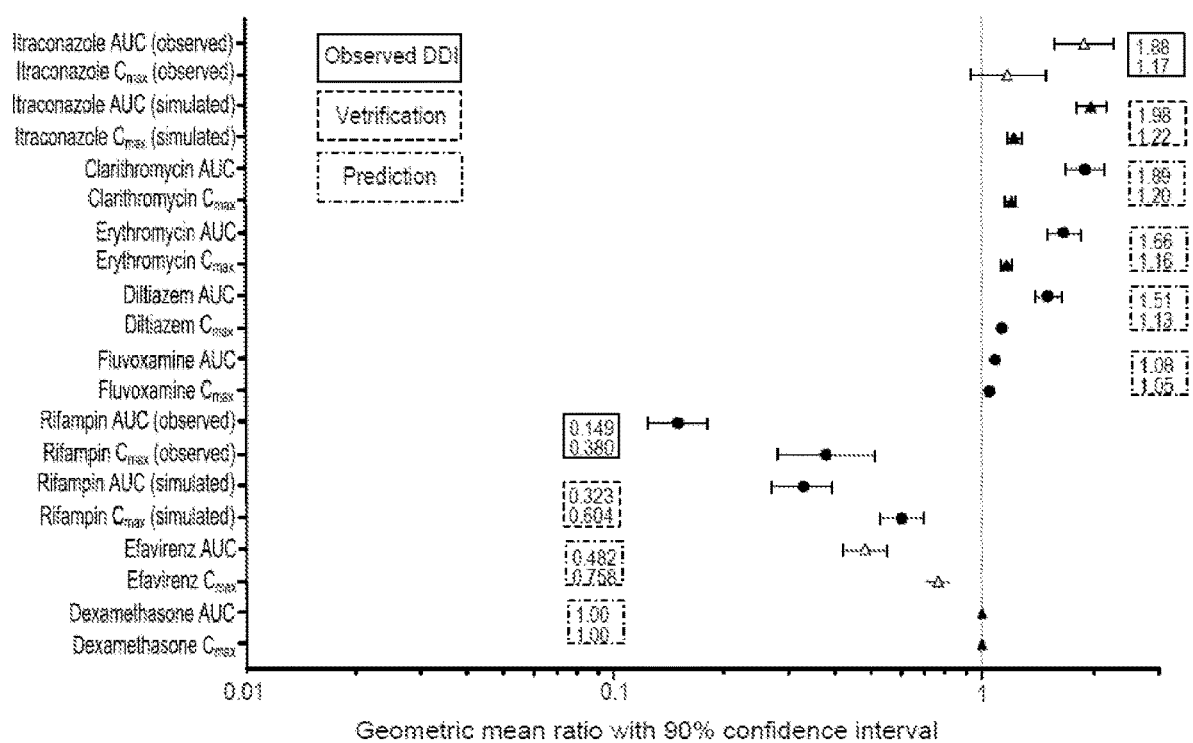
FIG. 8 shows the observed and simulated pemigatinib AUC and $C_{max}$ ratios with various CYP3A4 inhibitors and inducers.

The final pemigatinib PBPK model was not able to accurately predict drug-drug interaction between pemigatinib and rifampin which could be due to additional DDI effect on absorption of pemigatinib. The model with 55% $f_{mCYP3\_A4}$ was used to predict DDI effect on pemigatinib PK when co-administration with moderate and mild CYP3A4 inducers. Results of the simulated effect of strong, moderate, and mild CYP3A inhibitors/inducers on pemigatinib pharmacokinetics are summarized in Table 12 and illustrated in FIG. 8.

TABLE 12

Simulated Pemigatinib Drug-Drug Interactions With Various CYP3A4 Inhibitors or Inducers

| CYP3A4 Perpetrators and Dose Regimen | Inhibition/Induction Mechanism | AUC Ratio | $C_{max}$ Ratio |
|---|---|---|---|
| Itraconazole 200 mg QD | Strong, reversible inhibition | 1.98 (1.91, 2.05) | 1.22 (1.20, 1.24) |
| Clarithromycin 500 mg BID | Strong, time dependent inhibition | 1.89 (1.80, 1.98) | 1.20 (1.18, 1.21) |
| Erythromycin 500 mg BID | Moderate, time dependent inhibition | 1.66 (1.59, 1.73) | 1.16 (1.14, 1.17) |
| Diltiazem 60 mg TID | Moderate, time dependent inhibition | 1.51 (1.46, 1.56) | 1.13 (1.12, 1.14) |

TABLE 12-continued

Simulated Pemigatinib Drug-Drug Interactions With Various CYP3A4 Inhibitors or Inducers

| CYP3A4 Perpetrators and Dose Regimen | Inhibition/Induction Mechanism | AUC Ratio | $C_{max}$ Ratio |
|---|---|---|---|
| Fluvoxamine 50 mg QD | Mild, reversible inhibition | 1.082 (1.075, 1.089) | 1.048 (1.044, 1.053) |
| Rifampin 600 mg QD | Strong, inducer | 0.323 (0.299, 0.349) | 0.604 (0.572, 0.638) |
| Efavirenz 600 mg QD | Moderate, inducer | 0.482 (0.455, 0.512) | 0.758 (0.736, 0.781) |
| Dexamethasone 8 mg QD | Mild, inducer | 0.995 (0.994, 0.996) | 0.996 (0.996, 0.997) |

Values are presented in the format of geometric mean (90% confidence intervals).

The simulated DDI results for co-administration with various CYP3A4 inhibitors or inducers were used for pemigatinib dose recommendation. The model-simulated pemigatinib geometric mean $C_{max}$ and AUC ratios are 1.20 and 1.89, 1.16 and 1.66, 1.13 and 1.51, 1.05 and 1.08, 0.758 and 0.482, and 1.00 and 1.00, respectively, when coadministration with strong inhibitors clarithromycin, moderate inhibitors erythromycin and diltiazem, a mild inhibitor fluvoxamine, a moderate inducer efavirenz and a mild inducer dexamethasone. The recommendation based on this simulation and clinical DDI result is to reduce pemigatinib dose by approximately 50% for coadministration with strong CYP3A4 inhibitors. For coadministration with moderate CYP3A4 inhibitors, the model-simulated pemigatinib AUCs are increased by approximately 50% and it is covered by safety margin. Therefore, no dose adjustment is required with coadministration of pemigatinib and moderate and mild CYP3A4 inhibitors. The simulation and clinical DDI result also suggest that co-administration of a strong and moderate CYP3A4 inducers should be avoided due to larger than 50% of pemigatinib AUC decrease and no dose adjustment is required with coadministration of pemigatinib and mild CYP3A4 inducers. with clinical data. The estimated $f_{mCYP3A4}$ (55%) for pemigatinib was verified using the observed clinical DDI study with itraconazole.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of treating cancer comprising administering a therapy to a patient in need thereof, wherein the therapy comprises administering a therapeutically effective amount of pemigatinib to the patient while avoiding the concomitant administration of a CYP3A4 perpetrator.

2. A method of treating cancer comprising administering a therapy to a patient in need thereof, wherein the therapy comprises administering a therapeutically effective amount of pemigatinib to the patient while avoiding the concomitant administration of a strong CYP3A4 inhibitor.

3. The method of claim 1, A method of treating cancer comprising administering a therapy to a patient in need thereof, wherein the therapy comprises administering a therapeutically effective amount of pemigatinib to the patient while avoiding the concomitant administration of a moderate to strong CYP3A4 inducer.

4. A method of treating cancer comprising administering a therapy to a patient in need thereof, wherein the therapy comprises administering a therapeutically effective amount of pemigatinib to the patient while avoiding the concomitant administration of itraconazole.

5. A method of treating cancer comprising administering a therapy to a patient in need thereof, wherein the therapy comprises administering a therapeutically effective amount of pemigatinib to the patient while avoiding the concomitant administration of rifampin.

6. The method of claim 1, wherein the cancer is bladder cancer, breast cancer, cervical cancer, cancer of the small intestine, colorectal cancer, endometrial cancer, gastric cancer, head and neck cancer, kidney cancer, liver cancer, lung cancer, ovarian cancer, prostate cancer, testicular cancer, uterine cancer, vulvar cancer, esophageal cancer, gall bladder cancer, pancreatic cancer, thyroid cancer, skin cancer, brain cancer, leukemia, multiple myeloma, chronic lymphocytic lymphoma, adult T cell leukemia, B-cell lymphoma, acute myelogenous leukemia, Hodgkin's or non-Hodgkin's lymphoma, Waldenstrom's Macroglubulinemia, myeloproliferative neoplasms, chronic myelogenic lymphoma, acute lymphoblastic lymphoma, hairy cell lymphoma, Burkett's lymphoma, glioblastoma, melanoma, rhabdosarcoma, lymphosarcoma, osteosarcoma, solid tumor, cholangiocellular carcinoma, and myeloid/lymphoid neoplasms.

7. The method of claim 6, wherein the myeloid/lymphoid neoplasm is 8p11 myeloproliferative syndrome.

8. The method of claim 6, wherein the cancer is cholangiocellular carcinoma.

9. The method of claim 6, wherein the cancer is bladder cancer.

10. The method of claim 1, wherein the administration of pemigatinib comprises:
 (a) a continuous daily administration of an intended amount or adjusted amount of pemigatinib to the patient in need thereof; or
 (b) a 21-day dosing cycle comprising:14 days of daily administration of an intended amount or adjusted amount of pemigatinib to the patient in need thereof and 7 days without administration of pemigatinib.

11. The method of claim 1, wherein the cancer is liver cancer.

* * * * *